(12) United States Patent
Akeda et al.

(10) Patent No.: US 9,938,326 B2
(45) Date of Patent: Apr. 10, 2018

(54) PNEUMOCOCCAL VACCINE CONTAINING PNEUMOCOCCAL SURFACE PROTEIN A

(71) Applicant: Osaka University, Osaka (JP)

(72) Inventors: Yukihiro Akeda, Osaka (JP); Zhenyu Piao, Osaka (JP); Kazunori Oishi, Tokyo (JP)

(73) Assignee: Osaka University, Osaka (JP)

( * ) Notice: Subject to any disclaimer, the term of this patent is extended or adjusted under 35 U.S.C. 154(b) by 22 days.

(21) Appl. No.: 14/429,547

(22) PCT Filed: Mar. 22, 2013

(86) PCT No.: PCT/JP2013/058401
§ 371 (c)(1),
(2) Date: Jul. 1, 2015

(87) PCT Pub. No.: WO2014/045621
PCT Pub. Date: Mar. 27, 2014

(65) Prior Publication Data
US 2015/0320851 A1 Nov. 12, 2015

(30) Foreign Application Priority Data

Sep. 19, 2012 (JP) .................................. 2012-206039

(51) Int. Cl.
A61K 45/00 (2006.01)
C07K 14/315 (2006.01)
A61K 39/09 (2006.01)
A61K 39/00 (2006.01)
A61K 38/00 (2006.01)

(52) U.S. Cl.
CPC ........ *C07K 14/3156* (2013.01); *A61K 39/092* (2013.01); *A61K 38/00* (2013.01); *A61K 2039/54* (2013.01); *A61K 2039/55505* (2013.01); *A61K 2039/55561* (2013.01); *A61K 2039/70* (2013.01); *C07K 2319/00* (2013.01); *C07K 2319/705* (2013.01)

(58) Field of Classification Search
CPC ............................... A61K 39/00; A61K 39/02
USPC .................. 424/9.1, 9.2, 184.1, 234.1, 278.1
See application file for complete search history.

(56) References Cited

U.S. PATENT DOCUMENTS

| | | |
|---|---|---|
| 5,476,929 A | 12/1995 | Briles et al. |
| 5,586,225 A | 12/1996 | Onizuka et al. |
| 5,679,768 A | 10/1997 | Briles et al. |
| 5,728,387 A | 3/1998 | Briles et al. |
| 5,753,463 A | 5/1998 | Briles et al. |
| 5,804,193 A | 9/1998 | Briles et al. |
| 5,856,170 A | 1/1999 | Briles et al. |
| 5,871,943 A | 2/1999 | Briles et al. |
| 5,955,089 A | 9/1999 | Briles et al. |
| 5,965,141 A | 10/1999 | Briles et al. |
| 5,965,400 A | 10/1999 | Briles et al. |
| 5,980,909 A | 11/1999 | Briles et al. |
| 5,995,312 A | 11/1999 | Macleod |
| 5,997,882 A | 12/1999 | Briles et al. |
| 6,004,802 A | 12/1999 | Briles et al. |
| 6,027,734 A | 2/2000 | Briles et al. |
| 6,042,838 A | 3/2000 | Briles et al. |
| 6,231,870 B1 | 5/2001 | Briles et al. |
| 6,232,116 B1 | 5/2001 | Briles et al. |
| 6,500,613 B1 | 12/2002 | Briles et al. |
| 6,592,876 B1 | 7/2003 | Briles et al. |
| 6,638,516 B1 | 10/2003 | Becker et al. |
| 7,049,419 B2 | 5/2006 | Briles et al. |
| 7,078,042 B2 | 7/2006 | Briles et al. |
| 7,189,404 B2 | 3/2007 | Becker et al. |
| 2001/0016200 A1 | 8/2001 | Briles et al. |
| 2003/0059438 A1 | 3/2003 | Briles et al. |
| 2004/0067237 A1 | 4/2004 | Becker et al. |
| 2004/0077847 A1 | 4/2004 | Briles et al. |
| 2005/0196405 A1 | 9/2005 | Briles et al. |
| 2007/0026010 A1 | 2/2007 | Biemans et al. |

(Continued)

FOREIGN PATENT DOCUMENTS

| | | |
|---|---|---|
| JP | H06-504446 A | 5/1994 |
| JP | 2000-503676 A | 3/2000 |

(Continued)

OTHER PUBLICATIONS

Croney, C.M., et al. 2012, PspA family distribution, unlike capsular serotype, remains unaltered following introduction of the heptavalent pneumococcal conjugate vaccine. Clin Vaccine Immunol. 19: 891-896.

Shibayama, K.. et al., "Atarashiku Kaihatsu sareta Hib, Haien Kyukin, Rotavirus, HPV nado no Kaku Wakuchin no Yukosei, Anzensei narabini sono Touyouhou ni kansuru Kisoteki Rinshoteki Kenkyu" Pharmaceutrical and Medical Device Regulatory Science Project supported by Health and Labour Sciences Research Grant, 46-53 Mar. 2012.

McDaniel LS, Ralph BA, McDaniel DO et al. 1994. Localization of protection-eliciting epitopes on PspA of *Streptococcus pneumoniae* between amino acid residues 192 and 260. Microb Pathog. 17: 323-37.

(Continued)

*Primary Examiner* — Rodney P Swartz
(74) *Attorney, Agent, or Firm* — Mintz Levin Cohn Ferris Glovsky and Popeo, P.C.

(57) ABSTRACT

A pneumococcal vaccine comprising a fusion protein at least comprising a full-length family 1 pneumococcal surface protein A (PspA) or a fragment thereof, and a full-length family 2 PspA or a fragment thereof, in particular any one of the following fusion proteins (1) to (3):
(1) a fusion protein at least comprising a family 1, clade 2 PspA and a family 2, clade 3 PspA,
(2) a fusion protein at least comprising a family 1, clade 2 PspA and a family 2, clade 4 PspA, and
(3) a fusion protein at least comprising a family 1, clade 2 PspA and a family 2, clade 5 PspA,
is useful as a pneumococcal vaccine comprising a single protein antigen that has broadly cross-reactive immunogenicity and can induce immune response against a wide range of pneumococcal clinical isolates.

17 Claims, 9 Drawing Sheets

(56) References Cited

U.S. PATENT DOCUMENTS

| | | |
|---|---|---|
| 2011/0311577 A1 | 12/2011 | Biemans et al. |
| 2012/0237536 A1 | 9/2012 | Rappuoli et al. |

FOREIGN PATENT DOCUMENTS

| | | |
|---|---|---|
| JP | 2003-525208 A | 8/2003 |
| JP | 2006-520205 A | 9/2006 |
| JP | 2013/058401 A1 | 3/2013 |
| WO | 2000/076587 A1 | 12/2000 |
| WO | 2011/030218 A1 | 3/2011 |

OTHER PUBLICATIONS

Daniels CC, Coan P, King J et al. 2010. The proline-rich region of pneumococcal surface proteins A and C contains surface-accessible epitopes common to all pneumococci and elicits antibody-mediated protection against sepsis. Infect Immun. 78: 2163-2172.

Hollingshead SK, Becker R, Briles DE. 2000. Diversity of PspA: mosaic genes and evidence for past recombination in *Streptococcus pneumoniae*. Infect Immun. 68: 5889-5900.

Anh-Hue, Tu, Fulgham RL, McCrory MA et al. 1999. Pneumococcal surface protein A inhibits complement activation by *Streptococcus pneumoniae*. Infect Immun. 67: 4720-4724.

Ezoe H, Akeda Y, Piao Z, Aoshi T, Koyama S, Tanimoto T, Ken J. Ishii KJ, Oishi K. 2011. Intranasal vaccination with pneumococcal surface protein A plus poly(I:C) protects against secondary pneumococcal pneumonia in mice. Vaccine 29: 1754-1761.

Piao Z, Oma K, Ezoe H, Akeda Y, Tomono K, Oishi K. 2011. Comparative effects of toll-like receptor agonists on a low dose PspA intranasal vaccine against fatal pneumococcal pneumonia in mice. J Vaccines Vaccine 2:1, http://dx.doi.org/10.4172/2157-7560.1000113.

Ren B, Szalai AJ, Hollingshead SK et al. 2004. Effects of PspA and antibodies to PspA on activation and deposition of complement on the pneumococcal surface. Infect Immun. 72: 114-122.

Darrieux M, Moreno AT, Ferreira DM et al. 2008. Recognition of pneumococcal isolates by antisera raised against PspA fragments different clades. J Med Microbiol. 57: 273-278.

Moreno AT, Oliveira ML, Ferreira DM et al. 2010. Immunization of mice with single PspA Fragments induces Antibodies capable of mediating complement deposition on different pneumococcal strains and cross-protection. Clin Vaccine Immunol. 17: 439-446.

M. Darrieux, E. N. Miyaji, D. M. Ferreira, L. M. Lopes, A. P. Y. Lopes, B. Ren, D. E. Briles, S. K. Hollingshead, and L. C. C. Leite. 2007. Fusion Proteins Containing Family 1 and Family 2 PspA Fragments Elicit Protection against *Streptococcus pneumoniae* That Correlates with Antibody-Mediated Enhancement of Complement Deposition. Infect Immun. 75: 5930-5938.

Wei Xin, Yuhua Li, Hua Mo, Kenneth L. Roland, and Roy Curtiss III. 2009. PspA Family Fusion Proteins Delivered by Attenuated *Salmonella enterica* Serovar Typhimurium Extend and Enhance Protection against *Streptococcus pneumoniae*. Infect Immun. 77: 4518-4528.

Zhenyu Piao et al., "Hito-gata CpG ODN o Nanmaku Adjuvant to shi PspA no Yugo Tanpakushitsu (family1-family2) o hyoteki to shita Haien Kyukin Keibi Nenmaku Vaccine", Journal of the Japanese Association for Infectious Diseases, 2011, vol. 85, No. 6, pp. 734-735.

Zhenyu Piao et al., "Pneumococcal surface protein A(PspA) o Base to suru Haien Kyukin Vaccine", Journal of the Japanese Association for Infectious Diseases, 2012.3, vol. 86, special extra issue, p. 524, p.2-151.

Miyaji, Elaine N., et al., Analysis of Serum Cross-Reactivity and Cross-Protection Elicited by Immunization with DNA Vaccines against *Streptococcus pneumoniae* Expressing PspA Fragments from Different Clades; Infection & Immunity, Sep. 2002, pp. 5086-5090.

Database GenBank, Accession No. ABJ54172.

Database GenBank, Accession No. AAK74303.

Zhenyu Piao et al., "Pneumococcal surface protein A (PspA) o Base to suru Haien Kyukin Vaccine", Journal of the Japanese Association for Infectious Diseases, 2012. 11, vol. 86, No. 6, p. 876.

English translation of International Preliminary Report on Patentability (chapter II) issued in connection with the corresponding PCT application No. PCT/JP2013/058401.

Piao et al., "Pneumococcal surface protein (PspA)-based pneumococcal vaccine", The 86th general assembly of Japanese Association for Infectious Diseases, presentation No. P2-151, Apr. 26, 2012.

Briles, David E. et al., "Immunization of humans with recombinant pneumococcal surface protein A (rPspA) elicits antibodies that passively protect mice from fatal infection with *Streptococcus pneumoniae* bearing heterologous PspA"; The Journal of Infectious Diseases 2000; 182: 1694-1701.

Ochs, Martina M., et al., "Vaccine-Induced Human Antibodies to PspA Augment Complement C3 Deposition on *Streptococcus pneumoniae*"; Microbial Pathogenesis Mar. 2008; 44(3), pp. 204-214.

Extended European Search Report dated Apr. 28, 2016 in corresponding European Application No. 13840065.0, 11 pages.

Silva, Marcelo, et al., "Optimizing Expression of *Streptococcus pneumoniae* Surface Protein A, PspA: Serocross-Reactivity within Families of Antisera Induced Against Clades 1 and 3", Molecular Biotechnology, vol. 37, No. 2, Jun. 26, 2007, pp. 146-154.

Ochs, Bartlett, Briles et al. 2008 Vaccine-induced antibodies to PspA augment complement C3 deposition on *S. pneumoniae*.Microbial Pathogenesis 48 (Mar. 3): pp. 204-212. (available: http://www.sciencedirect.com/science/article/pii/S0882401007001325).†

Briles, Hollingshead, King et al. 2000. Immunization of Humans with recombinant pneumococcal surface protein A (rPspA) elicits antibodies that passively protect mice from fatal infection with *Streptococcus pneumoniae* bearing heterologous PspA. J of Infectious Diseases 182 (6): pp. 1694-1701. (available: https://jid.oxfordjournals.org/content/182/6/1694.short).†

Hollingshead, Becker, Briles 2000 Diversity of PspA: Mosaic genes and evidence of past recombination in *S. pneumoniae*. Infection and Immunity 68 (Oct. 10): pp. 5889-5900. (available: http://iai.asm.org/content/68/10/5889.short)†

† cited by third party

[FIG. 1]
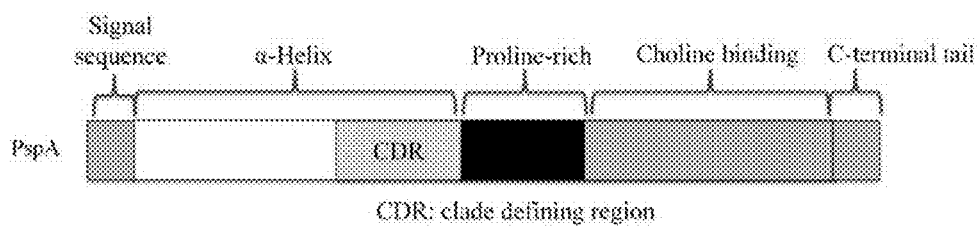
[FIG. 2]
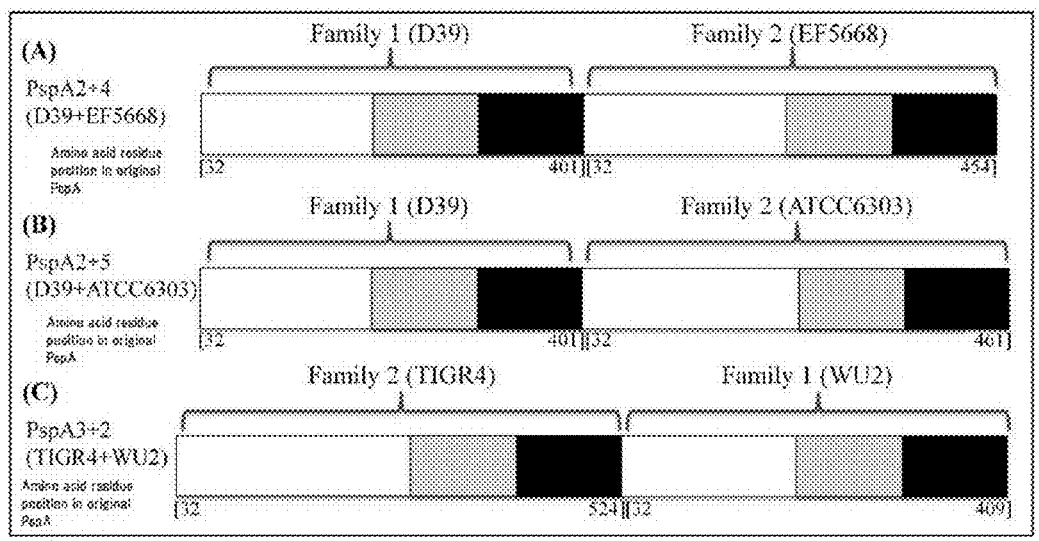
[FIG. 3]
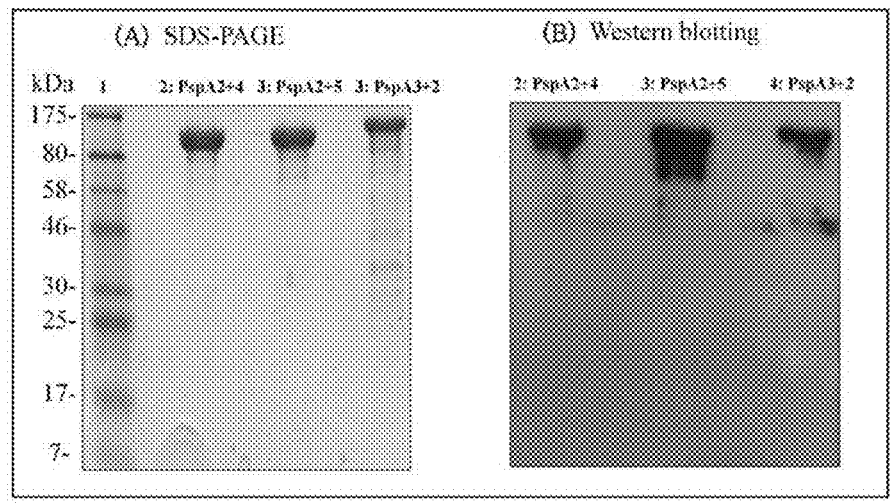

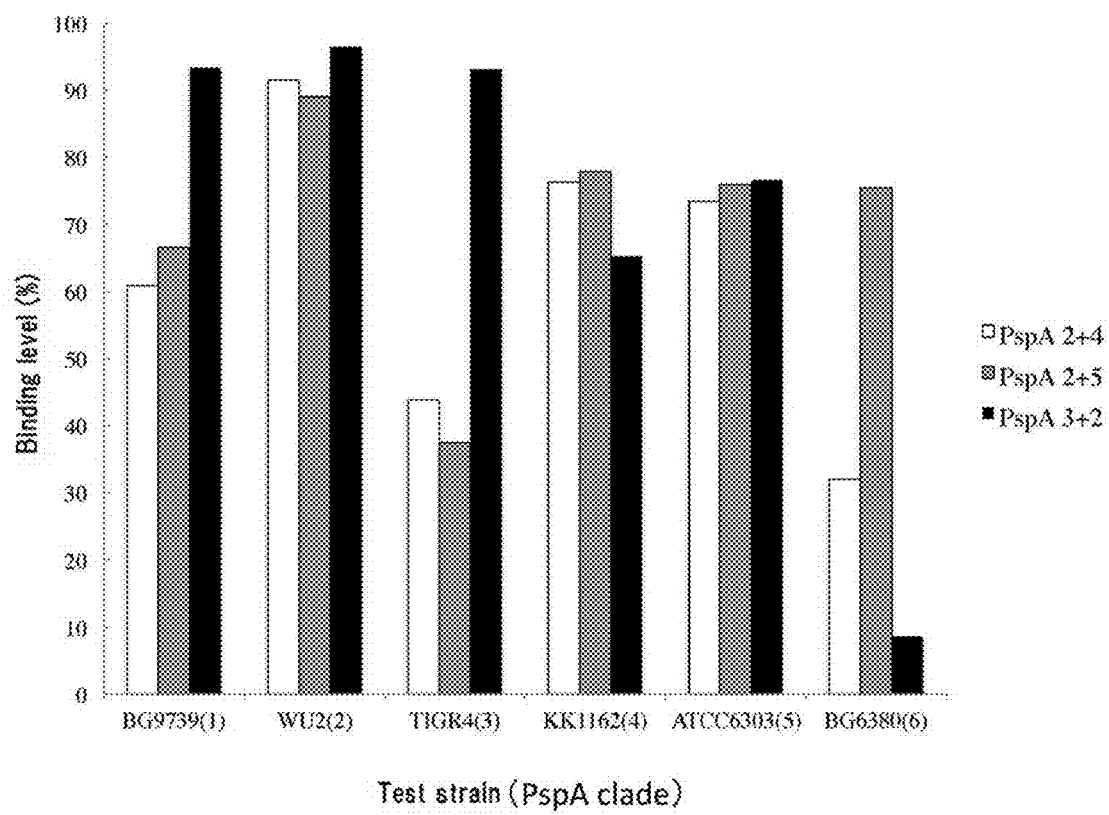
[FIG. 4]

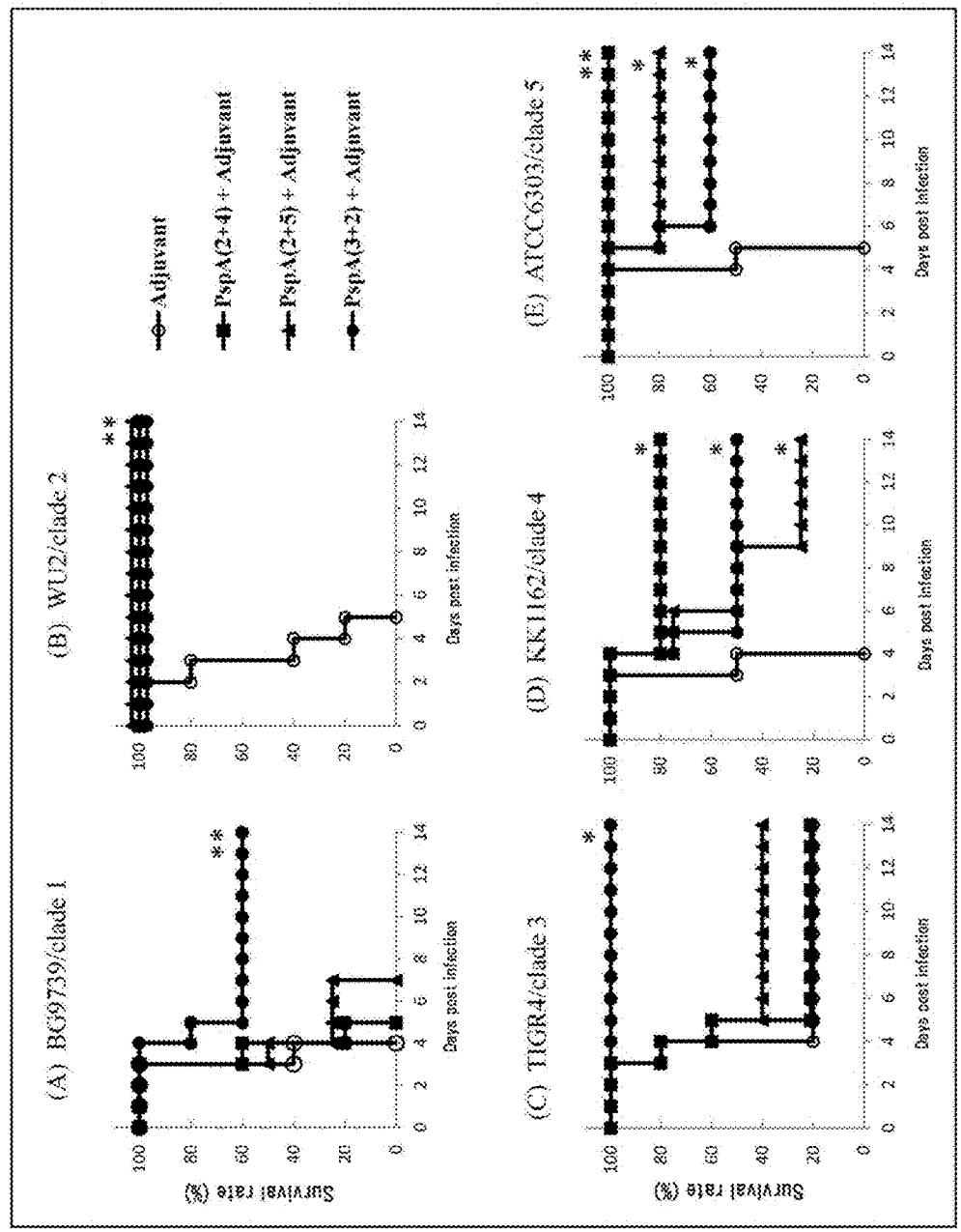
[FIG. 5]

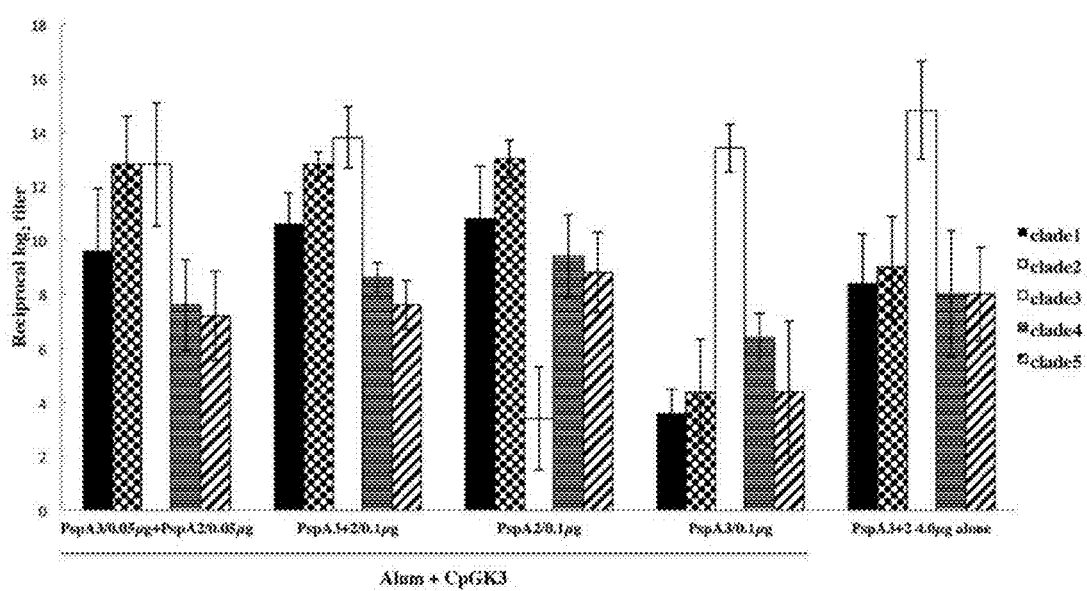
[FIG. 7]

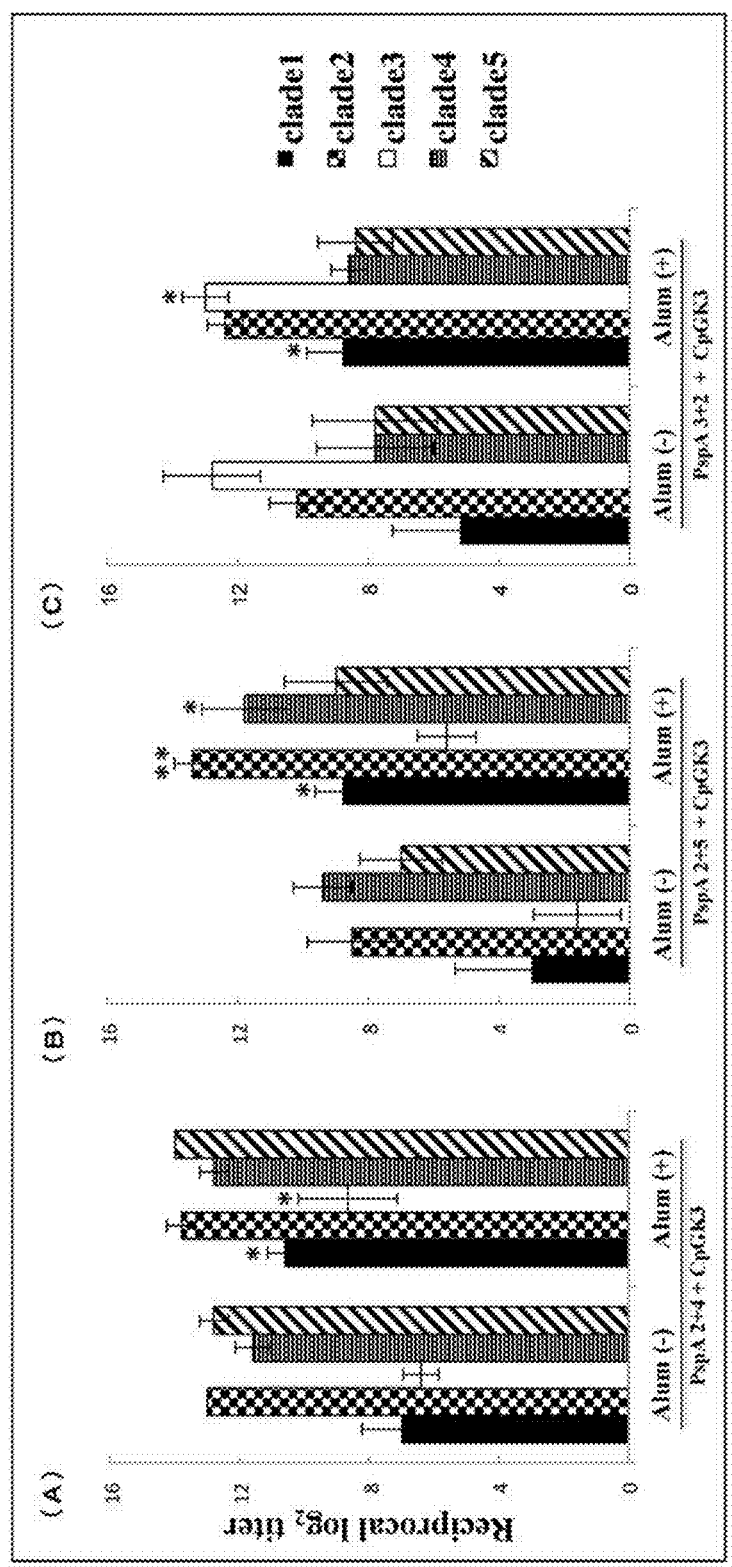
[FIG. 8]

[FIG. 9]
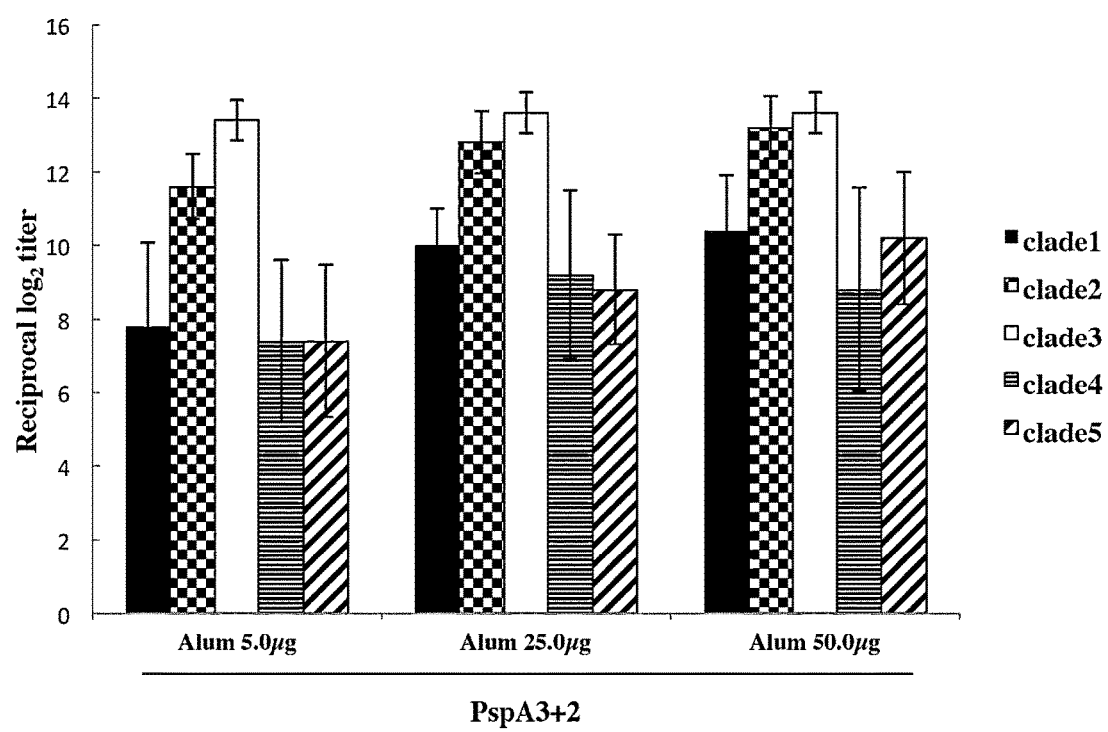

PNEUMOCOCCAL VACCINE CONTAINING PNEUMOCOCCAL SURFACE PROTEIN A

RELATED APPLICATIONS

This application is the U.S. national stage pursuant to 35 U.S.C. § 371, of U.S. international application Ser. No. PCT/JP2013/058401, filed Mar. 22, 2013, designating the United States and published in English on Mar. 27, 2014 as publication WO 2014/045621 A1, which claims the benefit of Japanese application Ser. No. 2012-206039, filed Sep. 19, 2012. The entire contents of the aforementioned patent applications are incorporated herein by this reference.

TECHNICAL FIELD

The present invention relates to a pneumococcal surface protein A-containing pneumococcal vaccine.

BACKGROUND ART

Pneumococcus is a major respiratory tract pathogen and causes infections in children and adults, such as invasive pneumococcal disease (IPD) including meningitis and sepsis, and community-acquired pneumonia. The antigens of the current pneumococcal vaccines are capsular polysaccharides, which determine the serotypes of pneumococci, and so far as known, there are at least 93 serotypes.

A heptavalent pneumococcal conjugate vaccine (PCV7), which is composed of a non-toxic diphtheria toxin ($CRM_{197}$) bound to polysaccharide antigens, was introduced as a pediatric vaccine in the U.S.A. in 2000. After the introduction of PCV7, the incidence of IPD caused by the seven serotypes covered by this vaccine was clearly reduced, but an increase in the incidence of pediatric and adult IPD caused by nonvaccine serotypes such as 19A became a problem. For this reason, a 13-valent pneumococcal conjugate vaccine (PCV13), which is composed of PCV7 and additional capsular polysaccharide antigens of six other serotypes, was introduced in 2010 and already approved for children and adults in the U.S.A.

However, according to a large-scale survey by Non Patent Literature 1, only 60% of pediatric invasive pneumococcal isolates collected in Alabama, U.S.A. between 2002 and 2010 (before the introduction of PCV13) had serotypes covered by PCV13. The remaining 40% of these isolates included 17 serotypes that were not covered by PCV13 (Non Patent Literature 1). In Japan, publicly-aided pediatric PCV7 vaccination was started in 2011, but it was reported in 2012 that the incidence of IPD caused by nonvaccine serotypes was increased as is the case in the U.S.A. (Non Patent Literature 2). Thus, it is unreal to continue complementing the current vaccines with capsular polysaccharide antigens of nonvaccine serotypes, and this implies the limitations of the current pneumococcal vaccines based on capsular polysaccharides.

Recently, pneumococcal surface protein A (hereinafter referred to as "PspA"), which is a pneumococcal surface protein antigen, has drawn attention as a novel pneumococcal vaccine antigen to compensate for the above-described drawback of the current pneumococcal vaccines. PspA has a structure composed of several domains shown in FIG. 1, and the α-helical region and the proline-rich region of PspA are known to have antigen epitopes for recognition by protective antibodies against pneumococcal infection (Non Patent Literature 3 and 4). According to the gene sequences of the antigen epitope regions, PspA is roughly grouped into three families including six subgroups called clades. Regarding the PspA family distribution, families 1 and 2 account for 98% or more of pneumococcal clinical isolates (Non Patent Literature 5). PspA is known to serve as a virulence factor to inhibit the deposition of complement C3 onto pneumococcal cells (Non Patent Literature 6), and in contrast, an anti-PspA specific antibody is known to exert protective effect against pneumococcal infection by antagonizing the inhibitory action of PspA against complement deposition (Non Patent Literature 7 and 8). This infection protective effect is reportedly exerted also by antibodies that cross-recognize different families of PspAs (Non Patent Literature 9). Due to the diversity of the cross-reactive immunogenicity among different PspAs (Non Patent Literature 10 and 11), appropriate selection of a combination of clades belonging to families 1 and 2 for broader cross-reactive immunogenicity is important in the development of PspA-based vaccines.

The usefulness of PspA proteins as an immunogenic component of vaccines against pneumococcal infection is described, for example, in Patent Literature 1 and 2.

Non Patent Literature 12 describes the examination on the vaccine effects of a fusion protein of a family 1, clade 1 PspA and a family 2, clade 4 PspA and a fusion protein of a family 1, clade 1 PspA and a family 2, clade 3 PspA. Non Patent Literature 13 describes the examination on the vaccine effect of a fusion protein of a family 1, clade 2 PspA and a family 2, clade 4 PspA. However, these PspA-based fusion proteins described in the two cited references have not been evaluated for the vaccine effects on pneumococcal stains expressing PspAs of clades 5 and 6, or for the vaccine effects against a wide range of pneumococcal clinical isolates, and also there has been no report that these fusion proteins are already in practical use.

CITATION LIST

Patent Literature

Patent Literature 1: JP 6-504446 B2
Patent Literature 2: JP 2000-503676 W

Non Patent Literature

Non Patent Literature 1:
Croney C M, Coats M T, Nahm M H et al. 2012. PspA family distribution, unlike capsular serotype, remains unaltered following introduction of the heptavalent pneumococcal conjugate vaccine. Clin Vaccine Immunol. 19: 891-896.
Non Patent Literature 2:
Pharmaceutical and Medical Device Regulatory Science Project supported by Health and Labour Sciences Research Grant "Atarashiku Kaihatsu sareta Hib, Haien Kyukin, Rotavirus, HPV nado no Kaku Wakuchin no Yukosei, Anzensei narabini sono Touyohouhou ni kansuru Kisoteki Rinshoteki Kenkyu", Shoni Shinshusei Kansensho Yurai Haien Kyukin no Ekigakuteki Kaiseki. Keigo Shibayama, 46-53 March 2012
Non Patent Literature 3:
McDaniel L S, Ralph B A, McDaniel D O et al. 1994. Localization of protection-eliciting epitopes on PspA of *Streptococcus pneumoniae* between amino acid residues 192 and 260. Microb Pathog. 17: 323-37.
Non Patent Literature 4:
Daniels C C, Coan P, King J et al. 2010. The proline-rich region of pneumococcal surface proteins A and C contains surface-accessible epitopes common to all pneumococci and elicits antibody-mediated protection against sepsis. Infect Immun. 78: 2163-2172.

Non Patent Literature 5:
Hollingshead S K, Becker R, Briles D E. 2000. Diversity of PspA: mosaic genes and evidence for past recombination in *Streptococcus pneumoniae*. Infect Immun. 68: 5889-5900.

Non Patent Literature 6:
Tu A H, Fulgham R L, McCrory M A et al. 1999. Pneumococcal surface protein A inhibits complement activation by *Streptococcus pneumoniae*. Infect Immun. 67: 4720-4724.

Non Patent Literature 7:
Ezoe H, Akeda Y, Piao Z, Aoshi T, Koyama S, Tanimoto T, Ken J. Ishii K J, Oishi K. 2011. Intranasal vaccination with pneumococcal surface protein A plus poly(I:C) protects against secondary pneumococcal pneumonia in mice. Vaccine 29: 1754-1761.

Non Patent Literature 8:
Piao Z, Oma K, Ezoe H, Akeda Y, Tomono K, Oishi K. 2011. Comparative effects of toll-like receptor agonists on a low dose PspA intranasal vaccine against fatal pneumococcal pneumonia in mice. J Vaccines Vaccin 2:1, www.omicsonline.org/comparative-effects-of-toll-like-receptor-agonists-on-a-low-dose-pspa-intranasal-vaccine-against-fatal-pneumococcal-pneumonia-in-mice-2157-7560.1000113.pdf Non Patent Literature 9:
Ren B, Szalai A J, Hollingshead S K et al. 2004. Effects of PspA and antibodies to PspA on activation and deposition of complement on the pneumococcal surface. Infect Immun. 72: 114-122.

Non Patent Literature 10:
Darrieux M, Moreno A T, Ferreira D M et al. 2008. Recognition of pneumococcal isolates by antisera raised against PspA fragments different clades. J Med Microbial. 57: 273-278. Non Patent Literature 11:
Moreno A T, Oliveira M L, Ferreira D M et al. 2010. Immunization of mice with single PspA Fragments induces Antibodies capable of mediating complement deposition on different pneumococcal strains and cross-protection. Clin Vaccine Immunol. 17: 439-446.

Non Patent Literature 12:
M. Darrieux, E. N. Miyaji, D. M. Ferreira, L. M. Lopes, A. P. Y. Lopes, B. Ren, D. E. Briles, S. K. Hollingshead, and L. C. C. Leite. 2007. Fusion Proteins Containing Family 1 and Family 2 PspA Fragments Elicit Protection against *Streptococcus pneumoniae* That Correlates with Antibody-Mediated Enhancement of Complement Deposition. Infect Immun. 75: 5930-5938.

Non Patent Literature 13:
Wei Xin, Yuhua Li, Hua Mo, Kenneth L. Roland, and Roy Curtiss III. 2009. PspA Family Fusion Proteins Delivered by Attenuated *Salmonella enterica* Serovar *Typhimurium* Extend and Enhance Protection against *Streptococcus pneumoniae*. Infect Immun. 77: 4518-4528.

SUMMARY OF INVENTION

Technical Problem

An object of the present invention is to identify a specific combination of pneumococcal surface protein antigens PspAs of different clades or strains, the combination having broadly cross-reactive immunogenicity and being capable of inducing immune response against a wide range of pneumococcal clinical isolates, and to provide a novel pneumococcal vaccine based on such a combination of PspAs. In particular, an object of the present invention is to identify a single protein antigen in the form of a fusion protein of a plurality of PspAs, the single protein antigen having broadly cross-reactive immunogenicity and being capable of inducing immune response against a wide range of pneumococcal clinical isolates, and to provide a novel pneumococcal vaccine based on such a single protein antigen.

Solution to Problem

The present invention includes the following to achieve the above-mentioned object.

[1] A pneumococcal vaccine comprising a fusion protein at least comprising a full-length family 1 pneumococcal surface protein A (PspA) (with the exception of PspAs of pneumococcal strains Rx1 and St435/96) or a fragment thereof, and a full-length family 2 PspA or a fragment thereof.

[2] The pneumococcal vaccine according to the above [1], wherein the family 1 PspA is a clade 2 PspA.

[3] The pneumococcal vaccine according to the above [2], wherein the fusion protein is any one of the following (1) to (3):

(1) a fusion protein at least comprising a family 1, clade 2 PspA and a family 2, clade 3 PspA, (2) a fusion protein at least comprising a family 1, clade 2 PspA and a family 2, clade 4 PspA, and (3) a fusion protein at least comprising a family 1, clade 2 PspA and a family 2, clade 5 PspA.

[4] The pneumococcal vaccine according to the above [3], wherein the fusion protein is any one of the following (4) to (6):

(4) a fusion protein consisting of a family 1, clade 2 PspA and a family 2, clade 3 PspA, (5) a fusion protein consisting of a family 1, clade 2 PspA and a family 2, clade 4 PspA, and (6) a fusion protein consisting of a family 1, clade 2 PspA and a family 2, clade 5 PspA.

[5] The pneumococcal vaccine according to any one of the above [1] to [4], wherein the PspA fragment at least contains the whole or part of a proline-rich region.

[6] The pneumococcal vaccine according to the above [5], wherein the PspA fragment consists of the whole or part of the proline-rich region, and the whole or part of an α-helical region adjacent thereto.

[7] The pneumococcal vaccine according to the above [2], wherein the family 1, clade 2 PspA is from a pneumococcal strain selected from the group consisting of D39, WU2, E134, EF10197, EF6796, BG9163 and DBL5.

[8] The pneumococcal vaccine according to the above [3], wherein the family 2, clade 3 PspA is from a pneumococcal strain TIGR4, BG8090 or AC122, the family 2, clade 4 PspA is from a pneumococcal strain EF5668, BG7561, BG7817 or BG11703, and the family 2, clade 5 PspA is from a pneumococcal strain ATCC6303 or KK910.

[9] The pneumococcal vaccine according to the above [1], wherein the fusion protein consists of an amino acid sequence which is identical or essentially identical to that represented by SEQ ID NO: 1, 3 or 5.

[10] A pneumococcal vaccine at least comprising a full-length family 1, clade 2 PspA or a fragment thereof, and a full-length family 2 PspA selected from the group consisting of clade 3, 4 and 5 PspAs, or a fragment thereof.

[11] The pneumococcal vaccine according to the above [10], wherein the PspAs are any one of the following (i) to (iii):

(i) a combination of only a family 1, clade 2 PspA and a family 2, clade 3 PspA,
(ii) a combination of only a family 1, clade 2 PspA and a family 2, clade 4 PspA, and
(iii) a combination of only a family 1, clade 2 PspA and a family 2, clade 5 PspA.
[12] The pneumococcal vaccine according to any one of the above [1] to [11], further comprising an adjuvant.
[13] The pneumococcal vaccine according to any one of the above [1] to [12], further comprising a vaccine component against a pathogen other than pneumococci.

Advantageous Effects of Invention

The present invention can provide a pneumococcal vaccine that has broadly cross-reactive immunogenicity and can induce immune response against a wide range of pneumococcal clinical isolates. The inoculation of the pneumococcal vaccine of the present invention can induce protective immunity against pneumococcal infections in children and adults.

BRIEF DESCRIPTION OF DRAWINGS

FIG. 1 shows the structure of a PspA protein.
FIG. 2 shows the structures of three kinds of PspA-based fusion proteins prepared in Example 1. (A) shows the structure of PspA2+4, (B) shows the structure of PspA2+5, and (C) shows the structure of PspA3+2.
FIG. 3(A) shows the results of SDS-PAGE of the indicated PspA-based fusion proteins,
and FIG. 3(B) shows the results of western blotting of the indicated PspA-based fusion proteins.
FIG. 4 shows the results of the measurement of the capacities of antiserum IgG to bind to the surface of pneumococcal cells of different PspA clades (the X-axis shows test strains). The antisera were obtained by immunization of mice with the indicated PspA-based fusion proteins.
FIG. 5 shows the results on the survival rates of PspA-based fusion protein-immunized mice during 2 weeks after infection with various pneumococci of different PspA clades. Immunization was performed using the indicated PspA-based fusion proteins. (A) shows the results of infection with $2 \times 10^7$ CFU of BG9739, (B) shows the results of infection with $2 \times 10^7$ CFU of WU2, (C) shows the results of infection with $5 \times 10^6$ CFU of TIGR4, (D) shows the results of infection with $1 \times 10^8$ CFU of KK1162, and (E) shows the results of infection with $5 \times 10^5$ CFU of ATCC6303.
FIG. 6A shows the results for PspA2+4-induced antiserum,
FIG. 6B shows the results for PspA2+5-induced antiserum,
and FIG. 6C shows the results for PspA3+2-induced antiserum.
FIG. 7 shows the results of the measurement of anti-PspA antibody titers of the antisera obtained by immunization of mice with PspA2 alone, PspA3 alone, a combination of PspA2 and PspA3, and PspA3+2 fusion protein.
FIG. 8 shows the results of the measurement of anti-PspA antibody titers of the antisera obtained by immunization of mice with three kinds of PspA-based fusion proteins (PspA2+4, PspA2+5, PspA3+2) together with CpG alone or a combination of CpG and Alum as an adjuvant.
FIG. 9 shows the results of the measurement of anti-PspA antibody titers of the antisera obtained by immunization of mice with PspA3+2 fusion protein together with various concentrations of Alum alone as an adjuvant.

DESCRIPTION OF EMBODIMENTS

<Pneumococcal Vaccine>

Figure 6A:
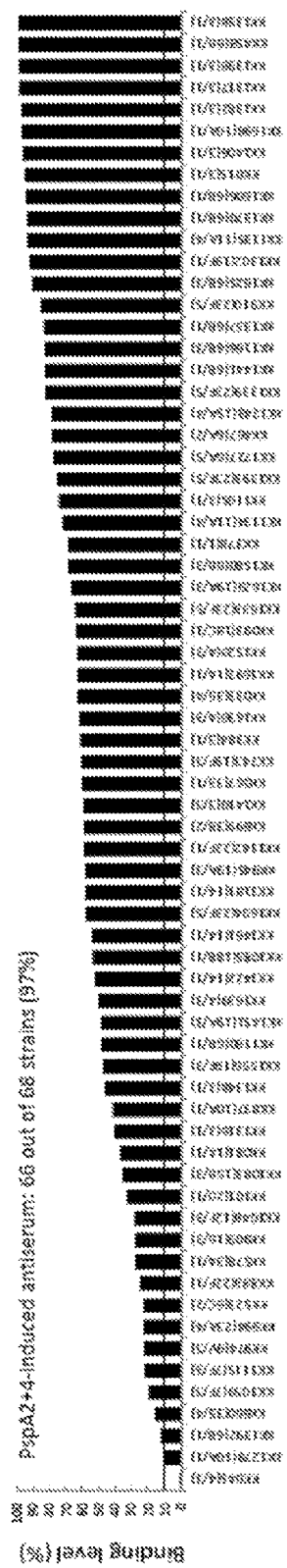
FIGS. 6A to 6C show the results of the measurement of the binding capacities of antiserum IgG for pneumococcal clinical isolates. The antisera were obtained by immunization of mice with the indicated PspA-based fusion proteins.

The present invention provides a pneumococcal vaccine comprising a fusion protein at least comprising a full-length family 1 PspA or a fragment thereof, and a full-length family 2 PspA or a fragment thereof. However, the present invention does not include a fusion protein comprising a pneumococcal strain Rx1 PspA (family 1, clade 2), which is used for fusion proteins of a family 1, clade 2 PspA and a family 2, clade 4 PspA described in Non Patent Literature 13. Moreover, the present invention does not include a fusion protein comprising a pneumococcal strain St435/96 PspA (family 1, clade 1) (for information on the strain, see Non Patent Literature 12 and TABLE 1 of Miyaji E N et al., Infect Immun. 70: 5086-5090, 2002), which is used as a family 1, clade 1 PspA for fusion proteins described in Non Patent Literature 12. A partial sequence of the gene encoding the pneumococcal strain St435/96 PspA, and the amino acid sequence thereof are registered with a database such as GenBank under accession number AY082387. Hereinafter, it should be noted that the "family 1 PspA" does not include the Rx1 PspA or the St435/96 PspA.

In the pneumococcal vaccine of the present invention (hereinafter sometimes referred to as "the vaccine of the present invention"), the fusion protein (hereinafter sometimes referred to as "the fusion protein of the present invention") at least comprises a family 1 PspA and a family 2 PspA. The fusion protein of the present invention may comprise three or more kinds of PspAs, or comprise PspAs together with another protein and/or a capsular polysaccharide (for example, a carrier protein, a capsular antigen for vaccines, etc.). Preferably, the fusion protein consists of two kinds of PspAs, i.e., a family 1 PspA and a family 2 PspA. The fusion protein may comprise, in addition to the amino acid sequences of PspAs, another amino acid sequence such as a tag sequence, a vector-derived sequence and a restriction enzyme sequence.

The order of the constituent proteins fused in the fusion protein of the present invention is not limited, and for example, in the case where the fusion protein is composed of two kinds of PspAs, i.e., family 1 and family 2 PspAs, the fusion protein may comprise the family 1 PspA at the N-terminal side and the family 2 PspA at the C-terminal side, or alternatively comprise the family 2 PspA at the N-terminal side and the family 1 PspA at the C-terminal side. Similarly, in the case where the fusion protein comprises three or more kinds of PspAs or comprises PspAs together with another protein, the order of the constituent proteins in the fusion protein is not limited.

For the fusion protein of the present invention, a PspA of a pneumococcus of which the PspA family and clade are already identified can preferably be used. In the case where a PspA of a pneumococcus of which the PspA family and clade are unidentified is used, the PspA family and clade identification of the pneumococcus preferably precedes the use. For the PspA family and clade identification, a PspA gene sequence putatively containing an α-helical region and a proline-rich region is subjected to PCR amplification followed by gene sequencing, and an about 400-bp nucleotide sequence upstream of the proline-rich region in the sequenced gene is compared with the corresponding sequences in the PspA genes of which the clades are already identified. Specifically, when the about 400-bp nucleotide sequence has 97 to 100% homology to the corresponding sequence of any of the PspA genes shown in Tables 1 and 2, both clades are regarded as the same. A PspA identified as clade 1 or 2 is defined as belonging to family 1, a PspA identified as clade 3, 4 or 5 is defined as belonging to family 2, and a PspA identified as clade 6 is defined as belonging to family 3 (Reference: Non Patent Literature 5 and Swiatlo E, Brooks-Walter A, Briles D E, McDaniel L S. Oligonucleotides identity conserved and variable regions of pspA and pspA-like sequences of Streptococcus pneumoniae. Gene 1997, 188: 279-284). In an alternative identification method, a PspA gene of interest is amplified with a set of primers specific to family 1 or 2, and the length of the PCR product determines the family of the PspA. Specifically, when the length of the PCR product is about 1000 bp, the PspA is defined as belonging to family 1, and when the length of the PCR product is about 1200 bp, the PspA is defined as belonging to family 2 (Reference: Vela Coral M C, Fonseca N, Castaneda E, Di Fabio J L, Hollingshead S K, Briles D E. Pneumococcal surface protein A of invasive Streptococcus pneumoniae isolates from Colombian children. Emerg Infect Dis 2001, 7: 832-6).

Exemplary pneumococci of which the PspA families and clades are identified include pneumococcal strains shown in Tables 1 and 2, and PspAs of these pneumococcal strains (Rx1 excluded) can preferably be used for the fusion protein of the present invention.

TABLE 1

Family 1

| Strain | Serotype | Clade | GenBank Accession No. |
| --- | --- | --- | --- |
| BG9739 | 4 | 1 | AF071804 |
| DBL6A | 6A | 1 | AF071805 |
| L81905 | 4 | 1 | AF071809 |
| BG8743 | 23 | 1 | AF071803 |
| AC94 | 9L | 1 | AF071802 |
| BG6692 | 33 | 1 | AF071808 |
| BG8838 | 6 | 1 | AF071807 |
| DBL1 | 6B | 1 | AF071806 |
| Rx1 | Rough | 2 | M74122 |
| E134 | 23 | 2 | AF071811 |
| EF10197 | 3 | 2 | AF071812 |
| EF6796 | 6A | 2 | AF071813 |
| BG9163 | 6B | 2 | AF071815 |
| DBL5 | 5 | 2 | AF071810 |
| WU2 | 3 | 2 | AF071814 |

TABLE 2

Family 2

| Strain | Serotype | Clade | GenBank Accession No. |
| --- | --- | --- | --- |
| EF3296 | 4 | 3 | AF071816 |
| BG8090 | 19 | 3 | AF071817 |
| AC122 | 9V | 3 | AF071818 |
| EF5668 | 4 | 4 | U89711 |
| BG7561 | 15 | 4 | AF071824 |
| BG7817 | 12 | 4 | AF071826 |
| BG11703 | 18 | 4 | AF071821 |
| ATCC6303 | 3 | 5 | AF071820 |

In the fusion protein of the present invention, the family 1 PspA is preferably a clade 2 PspA. The fusion protein is more preferably any of the following (1) to (3):
(1) a fusion protein at least comprising a family 1, clade 2 PspA and a family 2, clade 3 PspA,
(2) a fusion protein at least comprising a family 1, clade 2 PspA and a family 2, clade 4 PspA, and
(3) a fusion protein at least comprising a family 1, clade 2 PspA and a family 2, clade 5 PspA.

The fusion protein is still more preferably any of the following (4) to (6):
(4) a fusion protein consisting of a family 1, clade 2 PspA and a family 2, clade 3 PspA,
(5) a fusion protein consisting of a family 1, clade 2 PspA and a family 2, clade 4 PspA, and
(6) a fusion protein consisting of a family 1, clade 2 PspA and a family 2, clade 5 PspA.

The family 2 PspA is preferably a clade 3 PspA. Therefore, the vaccine of the present invention preferably comprises the above fusion protein (1) or (4).

The PspA used for the fusion protein may be a full-length PspA or a fragment thereof. The two or more kinds of PspAs as the constituents of the fusion protein may be all full-length PspAs, a combination of a full-length PspA(s) and a PspA fragment(s), or all PspA fragments. A PspA is first expressed as a protein (precursor) consisting of a signal sequence, an α-helical region, a proline-rich region, a choline-binding region and a C-terminal tail as shown in FIG. 1, and then the signal sequence is cleaved off, resulting in a mature PspA. That is, the full-length PspA means a PspA having the same structure as FIG. 1 but lacking the signal sequence. The PspA fragment used for the fusion protein of the present invention is not particularly limited as long as the fragment consists of part of the full-length PspA and can induce protective immunity against pneumococcal infections in a living body. Preferably, the PspA fragment contains the whole or part of the proline-rich region. In addition, the PspA fragment may further contain the whole or part of the α-helical region adjacent to the proline-rich region. Furthermore, it is preferable that the PspA fragment does not contain the C-terminal tail, and it is more preferable that the PspA fragment does not contain the choline-binding region or the C-terminal tail. That is, the PspA fragment used for the fusion protein of the present invention is preferably a PspA fragment consisting of part of the proline-rich region; a PspA fragment consisting of the whole of the proline-rich region; a PspA fragment consisting of part of the proline-rich region and part of the α-helical region adjacent thereto; a PspA fragment consisting of part of the proline-rich region and the whole of the α-helical region adjacent thereto; a PspA fragment consisting of the whole of the proline-rich region and part of the α-helical region adjacent thereto; or a PspA fragment consisting of the whole of the proline-rich region and the whole of the α-helical region. More preferred is a PspA fragment consisting of the whole of the proline-rich region and the whole of the α-helical region.

The location of each region of a PspA can be determined according to the report of Yother et al. (Yother J, Briles D E. 1992. Structural properties and evolutionary relationships of PspA, a surface protein of Streptococcus pneumoniae, as revealed by sequence analysis. J. Bacteriol. 174: 601-609). Specifically, the α-helical region in a PspA of the Rx1 strain is a domain that is identical to an α-helix-containing region (residues 1 to 288) predicted by a secondary structure prediction program but lacks the signal sequence (residues 1 to 31), and the α-helical region as used herein can be defined as a region having an amino acid sequence highly homologous to that of the above domain. The proline-rich region can be defined as a region that is located between the α-helical region and the choline-binding region and contains a high level of proline residues. The choline-binding region in a PspA of the Rx1 strain is a domain having 10 repeats of a relatively highly conserved 20-amino-acid sequence (based on TGWLQVNGSWYYLNANGAMA (SEQ ID NO: 24)), and the choline-binding region as used herein can be defined as a region having an amino acid sequence highly homologous to that of the above domain. The C-terminal tail can be defined as a region from the residue immediately following the final repeat in the choline-binding region to the C-terminal stop codon.

The length of the PspA fragment is not particularly limited as long as the length is sufficient for the induction of immune response in a living body. The PspA fragment preferably consists of at least 27 residues or more, more preferably 108 residues or more, and still more preferably 300 residues or more (Reference: Daniels C C, Coan P, King J, Hale J, Benton K A, Briles D E, Hollingshead S K. The Proline-Rich Region of Pneumococcal Surface Proteins A and C Contains Surface-Accessible Epitopes Common to All Pneumococci and Elicits Antibody-Mediated Protection against Sepsis. Infect. Immun. 2010. 78: 2163-2172).

Preferable examples of the family 1, clade 2 PspA include PspAs of pneumococcal strains D39, WU2, E134, EF10197, EF6796, BG9163, DBL5, etc. More preferred are PspAs of D39 and WU2. Preferable examples of the family 2, clade 3 PspA include PspAs of pneumococcal strains TIGR4, BG8090, AC122, etc. More preferred is a PspA of TIGR4. Preferable examples of the family 2, clade 4 PspA include PspAs of pneumococcal strains EF5668, BG7561, BG7817, BG11703, etc. More preferred is a PspA of EF5668. Preferable examples of the family 2, clade 5 PspA include PspAs of pneumococcal strains ATCC6303, KK910, etc. More preferred is a PspA of ATCC6303.

The fusion protein of the present invention is preferably composed of a combination of a D39 PspA and an EF5668 PspA, a combination of a D39 PspA and an ATCC6303 PspA, or a combination of a WU2 PspA and a TIGR4 PspA. Among them, more preferred is a combination of a WU2 PspA and a TIGR4 PspA, and still more preferred is a combination of a TIGR4 PspA at the N-terminal side and a WU2 PspA at the C-terminal side.

Furthermore, the fusion protein of the present invention preferably consists of an amino acid sequence which is identical or essentially identical to that represented by SEQ ID NO: 1, 3 or 5. Among them, more preferred is a fusion protein consisting of an amino acid sequence which is identical or essentially identical to that represented by SEQ ID NO: 5.

The amino acid sequence represented by SEQ ID NO: 1 constitutes a fusion protein of a D39 PspA and an EF5668 PspA, in which a vector-derived sequence containing a polyhistidine tag, a sequence of residues 32 to 401 of the amino acid sequence of the D39 PspA (GenBank Accession No. ABJ54172, 619aa), a sequence corresponding to an EcoRI recognition nucleotide sequence, and a sequence of residues 32 to 454 of the amino acid sequence of the EF5668 PspA (GenBank Accession No. AAC62252, 653aa) are connected in this order from the N-terminus.

The amino acid sequence represented by SEQ ID NO: 3 constitutes a fusion protein of a D39 PspA and an ATCC6303 PspA, in which a vector-derived sequence containing a polyhistidine tag, a sequence of residues 32 to 401 of the amino acid sequence of the D39 PspA (GenBank Accession No. ABJ54172, 619aa), a sequence corresponding to an EcoRI recognition nucleotide sequence, and a sequence of residues 32 to 461 of a partial amino acid sequence of the ATCC6303 PspA (GenBank Accession No. AF071820, 461aa) are connected in this order from the N-terminus.

The amino acid sequence represented by SEQ ID NO: 5 constitutes a fusion protein of a TIGR4 PspA and a WU2 PspA, in which a vector-derived sequence containing a polyhistidine tag, a sequence of residues 32 to 524 of the amino acid sequence of the TIGR4 PspA (Accession No. AAK74303, 744aa), a sequence corresponding to an EcoRI recognition nucleotide sequence, and a sequence of residues 32 to 409 of a partial amino acid sequence of the WU2 PspA (Accession No. AAF27710, 415aa) are connected in this order from the N-terminus.

The amino acid sequence essentially identical to that represented by SEQ ID NO: 1 is, for example, an amino acid sequence that is the same as SEQ ID NO: 1 except for having deletion, substitution or addition of one to several amino acids. As used herein, "deletion, substitution or addition of one to several amino acids" means deletion, substitution or addition of an amino acid (s) the number of which is practicable in a known method for preparing mutant peptides, such as site-directed mutagenesis (preferably 10 or less amino acids, more preferably 7 or less amino acids, and even more preferably 5 or less amino acids). Such a mutant protein is not limited to a protein artificially mutated by a known method for preparing mutant polypeptides, and may be a protein isolated and purified from nature. In addition, the amino acid sequence essentially identical to that represented by SEQ ID NO: 1 is, for example, an amino acid sequence which is at least 80% identical, more preferably at least 85%, 90%, 92%, 95%, 96%, 97%, 98% or 99% identical to that represented by SEQ ID NO: 1. The same holds for the amino acid sequence essentially identical to that represented by SEQ ID NO: 3 or 5.

The fusion protein consisting of the amino acid sequence essentially identical to that represented by SEQ ID NO: 1 is preferably a fusion protein having an activity of the essentially same nature as that of the fusion protein consisting of the amino acid sequence represented by SEQ ID NO: 1. The activity of the essentially same nature include the activity of inducing immune response against a wide range of pneumococcal strains, which is preferably at a level equivalent to (for example, about 0.5- to 20-fold, preferably about 0.5- to 2-fold) that of the fusion protein consisting of the amino acid sequence represented by SEQ ID NO: 1. The same holds for the fusion protein consisting of the amino acid sequence essentially identical to that represented by SEQ ID NO: 3 or 5.

The fusion protein of the present invention can be prepared using known genetic engineering techniques, specifically by constructing a recombinant expression vector having an expressible insert of a gene encoding the fusion protein of the present invention, transfecting the vector into appropriate host cells for expression of a recombinant protein, and purifying the recombinant protein. Alternatively, the preparation of the fusion protein of the present invention can be performed using a gene encoding the fusion protein of the present invention with a known in vitro coupled transcription-translation system (for example, a cell-free protein synthesis system derived from rabbit reticulocytes, wheat germ or *Escherichia coli*).

The vaccine of the present invention can induce immune response against pneumococci without any adjuvant and thus is highly useful. However, the vaccine of the present invention may comprise one or more kinds of adjuvants. In the case where the vaccine of the present invention comprises an adjuvant, the adjuvant can be selected as appropriate from well-known adjuvants. Specific examples of the well-known adjuvants include aluminum adjuvants (for example, aluminum salts such as aluminum hydroxide, aluminum phosphate and aluminum sulfate, or any combination thereof), complete or incomplete Freund's adjuvant, TLR ligands (for example, CpG, Poly(I:C), Pam3CSK4, etc.), BAY, DC-chol, pcpp, monophosphoryl lipid A, QS-21, cholera toxin and formylmethionyl peptides. Preferable adjuvants are aluminum adjuvants, TLR ligands and a combination of both.

In the case where the vaccine of the present invention comprises an adjuvant, the amount of the adjuvant is not particularly limited as long as the amount is sufficient to nonspecifically enhance immune response induced by the fusion protein of the present invention, and the amount can be selected as appropriate according to the kind of the adjuvant etc. For example, in the case where an aluminum adjuvant (aluminum hydroxide) and CpG are used in combination, it is preferable that the vaccine comprises an about 1- to 100-fold amount of the aluminum adjuvant and an about 1- to 50-fold amount of CpG relative to the amount of the fusion protein of the present invention on a mass basis.

The vaccine of the present invention may comprise a vaccine component against a pathogen other than pneumococci. That is, the present invention provides a combination vaccine comprising the above-described fusion protein of the present invention, which is a vaccine component against pneumococci, and a vaccine component against a pathogen other than pneumococci. The vaccine component against a pathogen other than pneumococci is not particularly limited, and for example, is a vaccine component which has been practically used in combination vaccines. Specific examples of such a vaccine component include diphtheria toxoid, pertussis toxoid, *Bordetella pertussis* antigen, tetanus toxoid, inactivated poliovirus, attenuated measles virus, attenuated rubella virus, attenuated mumps virus, *Haemophilus influenzae* type b polysaccharide antigen, hepatitis B virus surface (HBs) antigen and inactivated hepatitis A virus antigen.

Examples of currently available combination vaccines include diphtheria-pertussis-tetanus vaccine (DPT vaccine), diphtheria-pertussis-tetanus-inactivated poliovirus vaccine (DPT-IPV vaccine), measles-rubella vaccine (MR vaccine), measles-mumps-rubella vaccine (MMR), *Haemophilus influenzae* type b (Hib)-hepatitis B virus vaccine, hepatitis A and B virus vaccine, and diphtheria-pertussis-tetanus-hepatitis virus-inactivated poliovirus vaccine. It is preferable that any of these combination vaccines is supplemented with the fusion protein as a component of the pneumococcal vaccine of the present invention.

The vaccine of the present invention can be administered orally or parenterally. The parenteral administration includes intraperitoneal administration, subcutaneous administration, intracutaneous administration, intramuscular administration, intravenous administration, intranasal administration, transdermal administration and transmucosal administration. Preferred is parenteral administration and more preferred are intracutaneous administration, subcutaneous administration and intramuscular administration.

For the formulation of the vaccine of the present invention, the fusion protein of the present invention, a pharmaceutically acceptable carrier and if needed an additive are blended and formed into a dosage form. Specific examples of the dosage form include oral preparations such as tablets, coated tablets, pills, powders, granules, capsules, solutions, suspensions and emulsions; and parenteral preparations such as injections, infusions, suppositories, ointments and patches. The blending ratio of the carrier or the additive can be determined as appropriate based on the usual range in the pharmaceutical field. The carrier or the additive that can be blended is not particularly limited, and the examples include various carriers such as water, physiological saline, other aqueous solvents, and aqueous or oily bases; and various additives such as excipients, binders, pH adjusters, disintegrants, absorption enhancers, lubricants, colorants, corrigents and fragrances.

Examples of the additive used for solid oral preparations include excipients such as lactose, mannitol, glucose, microcrystalline cellulose and corn starch; binders such as hydroxypropyl cellulose, polyvinylpyrrolidone and magnesium aluminometasilicate; dispersants such as corn starch; disintegrants such as calcium carboxymethyl cellulose; lubricants such as magnesium stearate; solubilizing agents such as glutamic acid and aspartic acid; stabilizers; water soluble polymers including celluloses such as hydroxypropyl cellulose, hydroxypropylmethyl cellulose and methyl cellulose, and synthetic polymers such as polyethylene glycol, polyvinylpyrrolidone and polyvinyl alcohol; sweeteners such as white sugar, powder sugar, sucrose, fructose, glucose, lactose, reduced malt sugar syrup (maltitol syrup), reduced malt sugar syrup powder (maltitol syrup powder), high-glucose corn syrup, high-fructose corn syrup, honey, sorbitol, maltitol, mannitol, xylitol, erythritol, aspartame, saccharin and saccharin sodium; and coating agents such as white sugar, gelatin, hydroxypropyl cellulose and hydroxypropylmethyl cellulose phthalate.

The formulation of liquid oral preparations involves dissolution, suspension or emulsification in a generally used diluent. Examples of the diluent include purified water, ethanol and a mixture thereof. The liquid oral preparation may further contain a wetting agent, a suspending agent, an emulsifier, a sweetener, a flavoring agent, a fragrance, a preservative, a buffering agent and/or the like.

Examples of the additive used for injections for oral administration include isotonizing agents such as sodium chloride, potassium chloride, glycerin, mannitol, sorbitol, boric acid, borax, glucose and propylene glycol; buffering agents such as a phosphate buffer solution, an acetate buffer solution, a borate buffer solution, a carbonate buffer solution, a citrate buffer solution, a Tris buffer solution, a glutamate buffer solution and an ε-aminocaproate buffer solution; preservatives such as methyl parahydroxybenzoate, ethyl parahydroxybenzoate, propyl parahydroxybenzoate, butyl parahydroxybenzoate, chlorobutanol, benzyl alcohol, benzalkonium chloride, sodium dehydroacetate, disodium edetate, boric acid and borax; thickeners such as hydroxyethyl cellulose, hydroxypropyl cellulose, polyvinyl alcohol and polyethylene glycol; stabilizers such as sodium hydrogen sulfite, sodium thiosulfate, disodium edetate, sodium citrate, ascorbic acid and dibutylhydroxytoluene; and pH adjusters such as hydrochloric acid, sodium hydroxide, phosphoric acid and acetic acid. The injection may further contain an appropriate solubilizer. Examples of the solubilizer include alcohols such as ethanol; polyalcohols such as propylene glycol and polyethylene glycol; and nonionic surfactants such as polysorbate 80, polyoxyethylene hydrogenated castor oil 50, lysolecithin and Pluronic polyol. Liquid preparations such as injections can be directly preserved by freezing or preserved after removal of water by lyophilization etc. Lyophilized preparations can be reconstituted in distilled water for injection or the like just before use.

The vaccine of the present invention can be administered to any animal (a human or a non-human animal) that has an immune system. Examples of the animal include mammals such as humans, monkeys, cattle, horses, pigs, sheep, goats, dogs, cats, guinea pigs, rats and mice; and birds such as chickens, ducks and geese. Preferably, the vaccine of the present invention is administered to a human child or adult.

In the administration of the vaccine of the present invention, the dosing frequency and interval are not particularly limited. For example, the vaccine may be administered once, or multiple times at intervals of about two days to about eight weeks.

Although the dose of the vaccine varies with the administration subject, the administration method, etc., the dose per administration is preferably about 0.01 µg to about 10 mg, more preferably about 0.1 µg to about 1 mg, and still more preferably about 1 µg to about 0.1 mg.

The present invention includes a method for prevention or treatment of pneumococcal infections, and the method comprises administering an effective amount of the vaccine of the present invention to an animal.

The vaccine of the present invention has the following advantages over conventional pneumococcal vaccines which are conjugate vaccines using capsular polysaccharides as antigens.
1) The vaccine is effective against a wide variety of pneumococcal strains despite using a single fusion protein antigen.
2) Since the vaccine uses a protein antigen, the vaccine can be produced without the step of fusion with a carrier protein, and thus the production cost is low.
3) Since the vaccine uses a protein antigen, the vaccine does not require any carrier protein for induction of protective immunity in both children and adults.
4) The vaccine uses a single fusion protein and there is no need to mix a plurality of antigens.
5) The vaccine can be produced by a simple process involving purification of just one kind of fusion protein (vaccine antigen), and thus the production cost can be reduced.

The present invention include a pneumococcal vaccine at least comprising a full-length family 1, clade 2 PspA or a fragment thereof, and a full-length family 2 PspA selected from the group consisting of clade 3, 4 and 5 PspAs, or a fragment thereof. That is, the present invention include a pneumococcal vaccine at least comprising a clade 2 PspA and a clade 3 PspA, a pneumococcal vaccine at least comprising a clade 2 PspA and a clade 4 PspA, and a pneumococcal vaccine at least comprising a clade 2 PspA and a clade 5 PspA. In these embodiments of the pneumococcal vaccine, the PspAs in each of these three combinations may be present as separate proteins. Except for this point, these embodiments of the pneumococcal vaccine can be practiced in the same manner as the above-described pneumococcal vaccine comprising the fusion protein of the present invention.

In the case where the PspAs in each of the above-described three combinations are present as separate proteins in the pneumococcal vaccine, the PspAs are preferably any of the following (i) to (iii):
(i) a combination of only a family 1, clade 2 PspA and a family 2, clade 3 PspA,
(ii) a combination of only a family 1, clade 2 PspA and a family 2, clade 4 PspA, and
(iii) a combination of only a family 1, clade 2 PspA and a family 2, clade 5 PspA.

In the case where the PspAs in each of the above-described three combinations are present as separate proteins, the PspA fragment used preferably contains the same regions as those contained in the PspA fragment used for the above-described fusion protein. Preferable kinds of PspA-expressing pneumococcal strains are the same as those described for the fusion protein. Specifically, the clade 2 PspA is preferably a protein consisting of an amino acid sequence which is identical or essentially identical to that represented by SEQ ID NO: 25 or 26. The clade 3 PspA is preferably a protein consisting of an amino acid sequence which is identical or essentially identical to that represented by SEQ ID NO: 27. The clade 4 PspA is preferably a protein consisting of an amino acid sequence which is identical or essentially identical to that represented by SEQ ID NO: 28. The clade 5 PspA is preferably a protein consisting of an amino acid sequence which is identical or essentially identical to that represented by SEQ ID NO: 29.

The amino acid sequence represented by SEQ ID NO: 25 constitutes a protein consisting of the full-length α-helical region and the full-length proline-rich region of a D39 PspA (the amino acid sequence is shown in SEQ ID NO: 30, and the nucleotide sequence of the corresponding gene is shown in SEQ ID NO: 31), and corresponds to residues 32 to 401 of the amino acid sequence of the D39 PspA (SEQ ID NO: 30).

The amino acid sequence represented by SEQ ID NO: 26 constitutes a protein consisting of the full-length α-helical region and the full-length proline-rich region of a WU2 PspA (its partial amino acid sequence is shown in SEQ ID NO: 32, and the nucleotide sequence of the corresponding gene is shown in SEQ ID NO: 33), and corresponds to residues 32 to 409 of the partial amino acid sequence of the WU2 PspA (SEQ ID NO: 32).

The amino acid sequence represented by SEQ ID NO: 27 constitutes a protein consisting of the full-length α-helical region and the full-length proline-rich region of a TIGR4 PspA (the amino acid sequence is shown in SEQ ID NO: 34, and the nucleotide sequence of the corresponding gene is shown in SEQ ID NO: 35), and corresponds to residues 32 to 524 of the amino acid sequence of the TIGR4 PspA (SEQ ID NO: 34).

The amino acid sequence represented by SEQ ID NO: 28 constitutes a protein consisting of the full-length α-helical region and the full-length proline-rich region of an EF5668 PspA (the amino acid sequence is shown in SEQ ID NO: 36, and the nucleotide sequence of the corresponding gene is shown in SEQ ID NO: 37), and corresponds to residues 32 to 454 of the amino acid sequence of the EF5668 PspA (SEQ ID NO: 36).

The amino acid sequence represented by SEQ ID NO: 29 constitutes a protein consisting of the full-length α-helical region and the full-length proline-rich region of an ATCC6303 PspA (its partial amino acid sequence is shown in SEQ ID NO: 38, and the nucleotide sequence of the corresponding gene is shown in SEQ ID NO: 39), and corresponds to residues 32 to 461 of the amino acid sequence of the ATCC6303 PspA (SEQ ID NO: 38).

The protein consisting of an amino acid sequence essentially identical to that represented by any of SEQ ID NOS: 25 to 29 is defined in the same manner as set forth above regarding the protein consisting of the amino acid sequence essentially identical to the amino acid sequence represented by SEQ ID NO: 1.

<Polynucleotide>

The present invention provides a polynucleotide encoding the fusion protein of the present invention. The polynucleotide can be present in the form of RNA (for example, mRNA) or DNA (for example, cDNA or genomic DNA). The polynucleotide may be a double or single strand. The double strand may be a double-stranded DNA, a double-stranded RNA or a DNA-RNA hybrid. The single strand may be a coding strand (sense strand) or a non-coding strand (antisense strand). The polynucleotide of the present invention may be fused with a polynucleotide encoding a tag for labeling (a tag sequence or a marker sequence) at the 5'- or 3'-terminus. The polynucleotide of the present invention may further contain an untranslated region (UTR) sequence, a vector sequence (including an expression vector sequence), etc.

The polynucleotide of the present invention can be produced by obtaining two or more polynucleotides encoding different constituent PspAs of the fusion protein, and joining them. The polynucleotide encoding each constituent PspA of the fusion protein can be obtained by a well-known DNA synthesis method, PCR, etc. To be more specific, in one example, based on the amino acid sequence of each constituent PspA of the fusion protein of the present invention, the nucleotide sequence is designed by appropriate selection of a codon for each amino acid, and the designed nucleotide sequence is chemically synthesized on a commercial DNA synthesizer to give a desired polynucleotide. In another example, the information on the nucleotide sequence of the gene encoding a PspA of interest is obtained from a well-known database (GenBank etc.) (see the accession numbers in Tables 1 and 2), primers for amplifying a desired region of the PspA-encoding gene are designed based on the information, and using these primers, PCR amplification from the genomic DNA of a pneumococcus expressing the PspA of interest is performed to give a desired DNA fragment in a large amount. The thus-prepared separate polynucleotides encoding different constituent PspAs of the fusion protein are joined using a genetic engineering technique to give the polynucleotide of the present invention.

The polynucleotide encoding a fusion protein consisting of the amino acid sequence represented by SEQ ID NO: 1 is, for example, a polynucleotide consisting of the nucleotide sequence represented by SEQ ID NO: 2, but is not limited thereto. The polynucleotide encoding a fusion protein consisting of the amino acid sequence represented by SEQ ID NO: 3 is, for example, a polynucleotide consisting of the nucleotide sequence represented by SEQ ID NO: 4, but is not limited thereto. The polynucleotide encoding a fusion protein consisting of the amino acid sequence represented by SEQ ID NO: 5 is, for example, a polynucleotide consisting of the nucleotide sequence represented by SEQ ID NO: 6, but is not limited thereto.

<Expression Vector>

The present invention provides an expression vector used for the production of the fusion protein of the present invention. The expression vector of the present invention is not particularly limited as long as it contains a polynucleotide encoding the fusion protein of the present invention, but preferred are plasmid vectors carrying a recognition sequence for RNA polymerase (pSP64, pBluescript, etc.). The method for preparing the expression vector is not particularly limited, and the expression vector may be prepared with the use of a plasmid, a phage, a cosmid or the like. The kind of the vector is not particularly limited and any appropriate vector that can be expressed in host cells can be selected. For example, depending on the kind of the host cell, an appropriate promoter sequence to ensure the expression of the polynucleotide of the present invention is selected, and this promoter sequence and the polynucleotide of the present invention are inserted into a plasmid etc. to give a desired expression vector. After a host transformed with the expression vector of the present invention is cultured, cultivated or bred, the fusion protein of the present invention can be collected and purified from the culture products etc. by conventional methods (for example, filtration, centrifugation, cell disruption, gel filtration chromatography, ion exchange chromatography, affinity chromatography, etc.).

The expression vector preferably contains at least one selection marker. Examples of the marker include a dihydrofolate reductase gene and a neomycin resistance gene for eukaryote cell culture; and a tetracycline resistance gene, an ampicillin resistance gene and a kanamycin resistance gene for culture of *Escherichia coli* (*E. coli*) and other bacteria. Such a selection marker is useful for checking whether the polynucleotide of the present invention has been successfully transfected into host cells and is reliably expressed therein.

The host cell is not particularly limited and various known cells can preferably be used. Specific examples of the host cell include bacteria such as *E. coli*, yeasts (budding yeast *Saccharomyces cerevisiae* and fission yeast *Schizosaccharomyces pombe*), nematodes (*Caenorhabditis elegans*), *Xenopus laevis* oocytes and animal cells (for example, CHO cells, COS cells and Bowes melanoma cells). The method for transfecting the expression vector into host cells, i.e. the transformation method, is also not particularly limited and known methods such as electroporation, the calcium phosphate method, the liposome method and the DEAE dextran method can preferably be used.

<Transformant>

The present invention provides a transformant carrying the expression vector of the present invention. As used herein, the transformant encompasses a cell, a tissue and an organ as well as an individual organism. The kind of the organism to be transformed is not particularly limited, and the examples include various microorganisms, plants and animals listed above as examples of the host cell. The transformant of the present invention can preferably be used for the production of the fusion protein of the present invention. It is preferable that the transformant of the present invention stably expresses the fusion protein of the present invention, but a transformant transiently expressing the same can also be used.

The present invention also include the following.

[1] A fusion protein at least comprising a full-length family 1 PspA or a fragment thereof, and a full-length family 2 PspA or a fragment thereof.

[2] The fusion protein according to the above [1], being any one of the following (1) to (3):
(1) a fusion protein consisting of a family 1, clade 2 PspA and a family 2, clade 3 PspA,
(2) a fusion protein consisting of a family 1, clade 2 PspA and a family 2, clade 4 PspA, and
(3) a fusion protein consisting of a family 1, clade 2 PspA and a family 2, clade 5 PspA.

[3] The fusion protein according to the above [1] or [2], wherein the family 2 PspA is a clade 3 PspA.

[4] The fusion protein according to the above [1], wherein the PspA fragment at least contains the whole or part of a proline-rich region.

[5] The fusion protein according to the above [4], wherein the PspA fragment consists of the whole or part of the proline-rich region, and the whole or part of an α-helical region adjacent thereto.

[6] The fusion protein according to the above [1], consisting of an amino acid sequence which is identical or essentially identical to that represented by SEQ ID NO: 1, 3 or 5.

[7] A polynucleotide encoding the fusion protein according to any one of the above [1] to [6].

[8] An expression vector containing the polynucleotide according to the above [7].

[9] A transformant carrying the expression vector according to the above [8].
[10] Use of the fusion protein according to any one of the above [1] to [6] for production of a pneumococcal vaccine.
[11] A pneumococcal vaccine comprising the fusion protein according to any one of the above [1] to [6].
[12] The pneumococcal vaccine according to the above [11], further comprising an adjuvant.
[13] A method for prevention or treatment of pneumococcal infections, comprising administering an effective amount of the fusion protein according to any one of the above [1] to [6] to an animal.
[14] The fusion protein according to any one of the above [1] to [6] for use for prevention or treatment of pneumococcal infections.

EXAMPLES

Hereinafter, the present invention will be illustrated in detail by examples, but is not limited thereto.

Example 1: Preparation of PspA-Based Fusion Proteins

The three kinds of PspA-based fusion proteins shown in (A) (B) and (C) of FIG. 2 were prepared with the use of the PspAs of D39, TIGR4, EF5668, ATCC6303 and WU2 among the pneumococcal strains shown in Table 3. All gene cloning procedures were performed in *E. coli* DH5α. *E. coli* DH5α was cultured in LB medium (1% bacto tryptone, 0.5% yeast extract and 0.5% NaCl) and as needed, kanamycin was added at a final concentration of 30 μg/ml in the medium.

TABLE 3

| Strain | Serotype | PspA clade | Origin | GenBank Accession No. |
|---|---|---|---|---|
| BG9739 | 4 | 1 | UAB | AF071804 |
| D39 | 2 | 2 | UAB | CP000410.1 |
| WU2 | 3 | 2 | UAB | AF071814 |
| TIGR4 | 3 | 3 | UAB | AE005672.3 |
| EF5668 | 4 | 4 | UAB | U89711 |
| KK1162 | 11A | 4 | This study | |
| ATCC6303 | 3 | 5 | UAB | AF071820 |
| BG6380 | 37 | 6 | UAB | AF071823 |

UAB: University of Alabama at Birmingham, USA.

A DNA fragment encoding the N-terminal α-helical and proline-rich regions of the PspA of each strain was PCR-amplified from the genomic DNA of each strain with a specific set of primers shown in Table 4, and a desired pair of the PCR products were inserted into a pET28a(+) vector to give an expression vector for a PspA-based fusion protein. The specific procedure is described below.

TABLE 4

| Primer | Nucleotide Sequence (Bold letters indicate restriction enzyme recognition site) | SEQ ID NO. |
|---|---|---|
| P1 (NdeI-D39) | GGAATTCCATATGGAAGAATCTCCCGTAGCCAGT | 7 |
| P2 (D39-EcoRI) | GGAATTCTTTTGGTGCAGGAGCTGG | 8 |
| P3 (EcoRI-EF5668) | GGAATTCGAAGAATCTCCCGTAGCTAG | 9 |
| P4 (EF5668-XhoI) | CCGCTCGAGTTAGTGCAAGGAGCTGGTTTG | 10 |
| P5 (EcoRI-ATCC6303) | GGAATTCGAAGAATCTCCACAAGTTGTCG | 11 |
| P6 (ATCC6303-XhoI) | CCGCTCGAGTTATGGTGCAGGAACTGGTTG | 12 |
| P7 (NdeI-TIGR4) | GGAATTCCATATGGAAGAATCTCCACAAGTTGTC | 13 |
| P8 (TIGR4-EcoRI) | GGAATTCTGGAGTGGCTGGTTTTCTG | 14 |
| P9 (EcoRI-WU2) | GGAATTCGAAGAATCTCCCGTAGCTAG | 15 |
| P10 (WU2-XhoI) | CCGCTCGAGTTACTCTGGTTGTGGTGCAGGAGCTGGTTT | 16 |
| P11 (NdeI-BG9739) | GGAATTCCATATGGAAGAAGCCCCCGTAGCTAG | 19 |
| P12 (BG9739-XhoI) | CCGCTCGAGTTATTCTGGTTTAGGAGCTGGAG | 20 |
| P13 (D39-XhoI) | CCGCTCGAGTTATTTTGGTGCAGGAGCTGG | 21 |
| P14 (TIGR4-XhoI) | CCGCTCGAGTTATGGAGTGGCTGGTTTTCTG | 22 |
| P15 (NdeI-EF5668) | GGAATTCCATATGGAAGAATCTCCCGTAGCTAG | 23 |

PCR amplification of a pneumococcal strain D39 PspA gene (with primers P1 and P2) and PCR amplification of a pneumococcal strain TIGR4 PspA gene (with primers P7 and P8) gave products with 5'-end NdeI and 3'-end EcoRI restriction enzyme recognition sequences, and these PCR products were separately inserted into a pET28a(+) vector between the NdeI and EcoRI restriction sites. Next, PCR amplification of a pneumococcal strain EF5668 PspA gene (with primers P3 and P4) and PCR amplification of a pneumococcal strain ATCC6303 PspA gene (with primers P5 and P6) gave products with 5'-end EcoRI and 3'-end XhoI restriction enzyme recognition sequences, and these PCR products were separately inserted between the EcoRI and XhoI restriction sites of the above-prepared pET28a(+) vector having a D39 PspA gene insert, to give two kinds of expression vectors, i.e., expression vectors for D39- and EF5668-derived PspA-based fusion protein PspA2+4 and for D39- and ATCC6303-derived PspA-based fusion protein PspA2+5. In addition, PCR amplification of a pneumococcal strain WU2 PspA gene (with primers P9 and P10) gave a product with 5'-end EcoRI and 3'-end XhoI restriction enzyme recognition sequences, and this PCR product was inserted between the EcoRI and XhoI restriction sites of the above-prepared pET28a(+) vector having a PCR-amplified insert of the TIGR4 PspA gene, to give an expression vector for TIGR4- and WU2-derived PspA-based fusion protein PspA3+2. The nucleotide sequences of these three fusion genes (PspA2+4 gene, PspA2+5 gene and PspA3+2 gene) were verified with a DNA sequencer and identified as the nucleotide sequences represented by SEQ ID NOS: 2, 4 and 5, respectively.

The obtained PspA-based fusion protein expression vectors were separately used to transform *E. coli* BL21 (DE3), and the resulting three different transformants were cultured at 37° C. with shaking in an LB medium supplemented with 30 µg/ml kanamycin. For each transformant, when the absorbance at 600 nm (OD600) of the culture medium became about 0.8, IPTG (final concentration 0.5 mM) was added thereto, and then shaking culture was continued for another 3 hours to allow the expression of the PspA-based fusion protein in a large amount. After the cells were collected, the PspA-based fusion protein was extracted therefrom and purified by $Ni^{2+}$ affinity chromatography using a polyhistidine tag attached to the fusion protein at the N-terminus, followed by gel filtration. The purified fusion protein was subjected to SDS-PAGE (see FIG. 3A) and subsequent western blotting with an anti-PspA antibody (see FIG. 3B), and identified as a desired fusion protein.

Example 2: Capacities of PspA-Based Fusion Protein-Induced Antiserum IgG to Bind to the Surface of Pneumococcal Cells of Different PspA Clades (1) Immunization of Mice with PspA-Based Fusion Proteins
A given PspA-based fusion protein (0.1 µg of PspA2+4, PspA2+5 or PspA3+2) and an adjuvant (2.5 µg of CpGK3 and 5.0 µg of Alum) were mixed in LPS-free PBS, and subcutaneously injected into female 6-week-old C57/BL6j mice for vaccination. Each immunized group consists of 5 mice. The vaccination was performed every week, 3 times in total. One week after the final immunization (3rd vaccination), the blood was drawn from each mouse and the serum was separated.
(2) Measurement of Capacities of Antiserum IgG to Bind to the Surface of Pneumococcal Cells
Six pneumococcal strains corresponding to PspA clades 1 to 6 were used. Specifically, BG9739 was used as the strain of PspA clade 1, WU2 was used as the strain of PspA clade 2, TIGR4 was used as the strain of PspA clade 3, KK1162 was used as the strain of PspA clade 4, ATCC6303 was used as the strain of PspA clade 5, and BG6380 was used as the strain of PspA clade 6 (see Table 3). Each pneumococcal strain was cultured in THY medium (Todd-Hewitt broth supplemented with 0.5% yeast extract). During the logarithmic growth phase, glycerol was added at a final concentration of 25% in the culture medium and the strain was cryopreserved at −80° C. before use.

The pneumococcal strain was cultured on a blood agar medium overnight, subcultured on a fresh blood agar medium for 4 to 5 hours, and then collected in PBS. Ninety microliters of a pneumococcal suspension containing about $10^7$ CFU was reacted with 10 µl of an antiserum (a mixture of antisera from the animals in the same immunized group) at 37° C. for 30 minutes. The reaction mixture was further reacted with an FITC-labeled anti-mouse IgG goat antibody, subsequent washing and centrifugation were performed, and the fluorescence intensity on the cells was measured by flow cytometry.
(3) Results
The results are shown in FIG. 4. The binding level is expressed as a percentage of the number of antiserum IgG-bound pneumococcal cells in 10000 pneumococcal cells. The PspA3+2-induced antiserum showed high binding to any of the pneumococcal strains of PspA clades 1 to 5. The PspA2+4-induced antiserum and the PspA2+5-induced antiserum showed a slightly low binding to TIGR4, a pneumococcal strain of PspA clade 3, but showed high binding to the pneumococcal strains of the other PspA clades. Regarding the binding to BG6380, a pneumococcal strain of PspA clade 6, the PspA2+5-induced antiserum showed the highest value.

Example 3: Infection Protective Effect of Immunization with PspA-Based Fusion Proteins in Fatal Pneumonia Murine Model (1) Experimental Method
Mice were immunized with the PspA-based fusion proteins in the same manner as in Example 2. Mice injected with an adjuvant alone were assigned to a negative control. The below-mentioned pneumococcal strains expressing PspAs of clades 1 to 5 (see Table 3) were transnasally injected into the mice 2 weeks after the final immunization (3rd vaccination), to create fatal pneumonia murine models. The lethal infection doses per mouse were $2\times10^7$ CFU for BG9739 (clade 1), $2\times10^7$ CFU for WU2 (clade 2), $5\times10^6$ CFU for TIGR4 (clade 3), $1\times10^8$ CFU for KK1162 (clade 4), and $5\times10^5$ CFU for ATCC6303 (clade 5). The number of animals per group was 10, or in some cases, 8 (BG9739-infected PspA2+5-immunized group, KK1162-infected negative control group, KK1162-infected PspA3+2-immunized group, and ATCC6303-infected negative control group).

The survival rate was monitored over 2 weeks after the pneumococcal infection of the immunized mice. The differences in the survival rates among the groups were analyzed by the Kaplan-Meier log-rank test. When the P value was smaller than 0.05, the difference was regarded as statistically significant.
(2) Results
The results are shown in FIG. 5. In FIG. 5, the symbol * indicates significant difference at P<0.05 in the mouse survival rates between the vaccination group and the adjuvant injection group, and the symbol ** indicates significant difference at P<0.01 in the same comparison. (A) shows the results for BG9739 (clade 1), (B) shows the results for WU2 (clade 2), (C) shows the results for TIGR4 (clade 3), (D) shows the results for KK1162 (clade 4), and (E) shows the results for ATCC6303 (clade 5). In the PspA3+2-immunized mice, the survival rate after infection with any of the pneumococcal strains of PspA clades 1 to 5 was significantly improved. In both the PspA2+4-immunized mice and the PspA2+5-immunized mice, the survival rate after infection with the pneumococcal strain of PspA clade 2, 4 or 5 was significantly improved.

Example 4: Measurement of Binding Capacities of Antiserum IgG for Pneumococcal Clinical Isolates (1) Experimental Method Using the PspA-based fusion protein-induced antisera obtained in Example 2, the binding capacities of antiserum IgG for pneumococcal clinical isolates were measured. The procedure was the same as that in Example 2 except that the pneumococcal strains used were clinical isolates.

The PspA families and clades of the pneumococcal clinical isolates were identified as follows. PCR amplification from the genomic DNA of each pneumococcal clinical isolate was performed with the primers LSM12 and SKH2 shown below, and the PCR product was sequenced. An about 400-bp nucleotide sequence upstream of the proline-rich region in the sequenced gene was compared with the corresponding sequences in the PspA genes of which the families and clades were already identified, and thereby the family and clade of each pneumococcal clinical isolate were determined (Reference: Pimenta F C, Ribeiro-Dias F, Brandileone M C et al. 2006. Genetic diversity of PspA types among nasopharyngeal isolates collected during an ongoing surveillance study of children in Brazil. J Clin Microbiol. 44: 2838-43).

```
LSM12:
                                         (SEQ ID NO: 17)
CCGGATCCAGCGTCGCTATCTTAGGGGCTGGTT

SKH2:
                                         (SEQ ID NO: 18)
CCACATACCGTTTTCTTGTTTCCAGCC
```

(2) Evaluation Criterion and Results

Since the binding of antiserum IgG to PspA proteins on the pneumococcal cell surface is essential for infection protective effect as described above, the binding capacity of IgG for pneumococcal cells was measured and used for the evaluation of the coverage of pneumococcal clinical isolates by each PspA-based fusion protein.

Figure 6B:
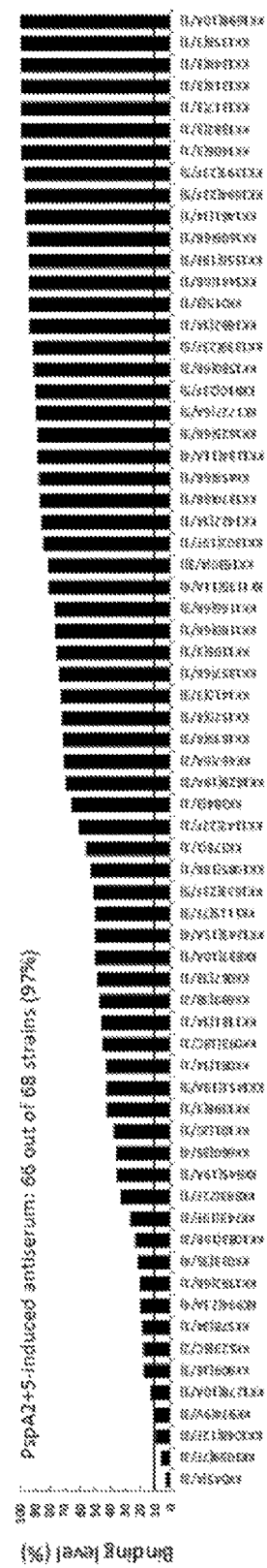
Figure 6C:
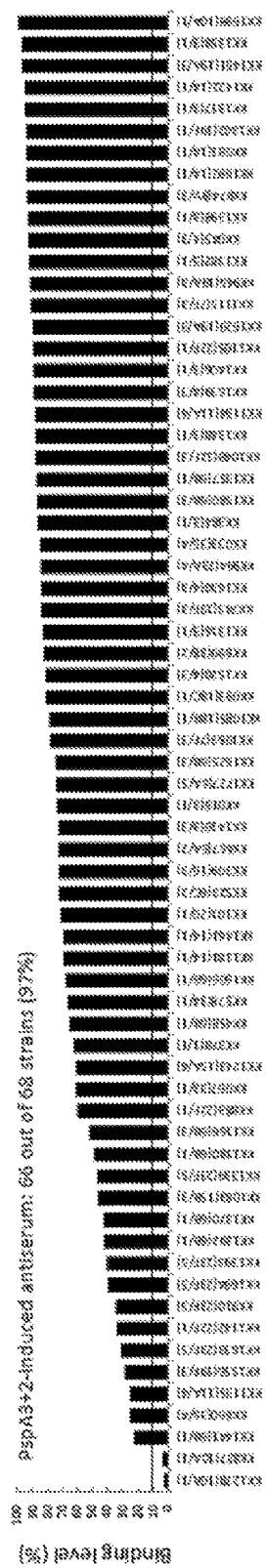

The results are shown in FIG. 6. In FIG. 6, the serotype and PspA clade of each pneumococcal clinical isolate are shown in the parentheses. In (A) PspA2+4-induced antiserum, (B) PspA2+5-induced antiserum and (C) PspA3+2-induced antiserum, the binding capacities of antiserum IgG for almost all the pneumococcal clinical isolates (97.0%) met the criterion (binding level of 10% or more).

Example 5: Measurement of Anti-PspA Antibody Titers of PspA Protein-Induced Antisera (1) Preparation of Antigen Proteins of Different PspA Clades For each of clades 1 to 5, a recombinant PspA consisting of an α-helical region and a proline-rich region was prepared and used as an antigen protein. The clade 1 PspA used was from BG9739, the clade 2 PspA used was from D39, the clade 3 PspA used was from TIGR4, the clade 4 PspA used was from EF5668, and the clade 5 PspA used was from ATCC6303. Expression vectors for the antigen proteins of different PspA clades were prepared as follows.

For each PspA, a DNA fragment encoding α-helical and proline-rich regions was PCR-amplified to give a product with 5'-end NdeI and 3'-end XhoI restriction enzyme recognition sequences. The PCR primers used were primers P11 and P12 for BG9739, primers P1 and P13 for D39, primers P7 and P14 for TIGR4, primers P15 and P4 for EF5668, and primers P7 and P6 for ATCC6303. The obtained PCR products were separately inserted into a pET28a(+) vector between the NdeI and XhoI restriction sites. The obtained expression vectors were separately used to transform E. coli BL21 (DE3), and the resulting five different transformants were cultured at 37° C. with shaking in an LB medium supplemented with 30 μg/ml kanamycin. For each transformant, when the OD600 of the culture medium became about 0.8, IPTG (final concentration 0.5 mM) was added thereto, and then shaking culture was continued for another 3 hours to allow the expression of the PspA-based antigen protein in a large amount. After the cells were collected, the PspA-based antigen protein was extracted therefrom and purified by $Ni^{2+}$ affinity chromatography using a polyhistidine tag attached to the antigen protein at the N-terminus, followed by gel filtration. The purified PspA-based antigen protein was subjected to SDS-PAGE and subsequent western blotting, and identified as a desired protein.

(2) Immunization of Mice with Antigens

The antigens used were the above-prepared clade 2 PspA-based antigen protein (PspA2) and clade 3 PspA-based antigen protein (PspA3), and a PspA-based fusion protein prepared in Example 1 (PspA3+2). Female 6-week-old C57/BL6j mice were divided into the following five groups each consisting of 5 mice.

PspA3+PspA2-immunized group (0.05 μg of PspA3, 0.05 μg of PspA2 and an adjuvant were injected)

PspA3+2-immunized group (0.1 μg of PspA3+2 and an adjuvant were injected)

PspA2-immunized group (0.1 μg of PspA2 and an adjuvant were injected)

PspA3-immunized group (0.1 μg of PspA3 and an adjuvant were injected)

PspA3+2-immunized group (4.0 μg of PspA3+2 was injected)

The adjuvant used was 2.5 μg of CpGK3 and 5.0 μg of Alum. An antigen solution was prepared in LPS-free PBS and subcutaneously injected into the mice for vaccination. The vaccination was performed every week, 3 times in total. One week after the final immunization (3rd vaccination), the blood was drawn from each mouse and the serum was separated.

(3) ELISA

The purified antigen protein of each PspA clade was prepared at 5 μg/ml, and added to 96-well plates at 100 μl/well. The plates were allowed to stand at 4° C. overnight to give antigen-coated plates. The plates were washed with PBST (PBS containing 0.05% Tween 20), serially diluted samples of each antiserum were added at 50 μl/well, and the plates were allowed to stand at 37° C. for 30 minutes. After this, each well was washed with PBST, a 2000-fold diluted alkaline phosphatase-labeled anti-mouse IgG goat antibody was added at 100 μl/well, and the plates were allowed to stand at room temperature with protection from light for 45 minutes. Subsequently, the absorbance at 405 nm (OD405) was measured. The anti-PspA antibody titer of each antiserum was expressed as the $Log_2$ of the reciprocal of the antiserum dilution at which the absorbance was 0.1 after subtraction of the absorbance of the negative control was 0.1.

(4) Results

The results are shown in FIG. 7. When PspA2 was used alone, the antibody titer against clade 3 PspA was low, and when PspA3 was used alone, the antibody titers against the PspAs of clades 1, 2, 4 and 5 were low. When PspA2 and PspA3 were used in combination, the antibody titers against all of the PspAs of clades 1 to 5 were high. When the PspA2-PspA3 fusion protein (PspA3+2) was used, the antibody titers against the PspAs of all the clades were equivalent to or higher than those in the combined use of PspA2 and PspA3. It was also shown that immunization with a high concentration of the PspA2-PspA3 fusion protein (PspA3+2), even in the absence of the adjuvant, provided high antibody titers against the PspAs of all the clades. These results show that the PspA-based fusion protein has a potential of providing antibody titers equivalent to or higher than those in a combined use of the two PspAs as separate proteins, does not require a combined use with the adjuvant to provide high antibody titers, and thus is very useful as an antigen of pneumococcal vaccines.

Example 6: Examination on Adjuvant (1)

The effect of CpG used in combination with Alum or used alone as an adjuvant was examined.
(1) Immunization of Mice
The antigens used were the three kinds of PspA-based fusion proteins prepared in Example 1 (PspA2+4, PspA2+5, PspA3+2), and the adjuvant used was a combination of CpG and Alum, or CpG alone. The following six groups were prepared.
   0.1 µg of PspA2+4+2.5 µg of CpGK3
   0.1 µg of PspA2+4+2.5 µg of CpGK3+5.0 µg of Alum
   0.1 µg of PspA2+5+2.5 µg of CpGK3
   0.1 µg of PspA2+5+2.5 µg of CpGK3+5.0 µg of Alum
   0.1 µg of PspA3+2+2.5 µg of CpGK3
   0.1 µg of PspA3+2+2.5 µg of CpGK3+5.0 µg of Alum
An antigen solution was prepared in LPS-free PBS and subcutaneously injected into the mice for vaccination. The vaccination was performed every week, 3 times in total. One week after the final immunization (3rd vaccination), the blood was drawn from each mouse and the serum was separated.
(2) ELISA
ELISA was performed in the same manner as in Example 5, and the anti-PspA antibody titers of the antisera were determined.
(3) Results
The results are shown in FIG. 8. In FIG. 8, the symbol * indicates that the antibody titer against the PspA-based antigen protein of a given clade in the Alum-addition group is significantly higher at $P<0.05$ than that in the Alum-free group, and the symbol ** indicates that the Alum-addition group has a significantly higher antibody titer at $P<0.01$ in the same comparison. In the PspA2+4 groups, under Alum-free conditions, the antibody titers against the PspAs of clades 2, 4 and 5 were high while the antibody titers against the PspAs of clades 1 and 3 were low, but under Alum-addition conditions, the antibody titers against the PspAs of clades 1 and 3 were increased. In the PspA2+5 groups, under Alum-free conditions, the antibody titers against the PspAs of clades 1 and 3 were particularly low, and even under Alum-addition conditions, the antibody titer against the clade 3 PspA was still low. In the PspA3+2 groups, under Alum-free conditions, the antibody titer against the clade 1 PspA was low, but under Alum-addition conditions, the antibody titers against the PspAs of all the clades were high. These results show that, under the conditions in these experiments, the addition of Alum increases the specific antibody titers against PspAs and that the fusion type PspAs induce high specific antibody titers against the PspAs of all the clades.

Example 7: Examination on Adjuvant (2)

The effect of Alum used alone, not in combination with CpG, as an adjuvant was examined.
(1) Immunization of Mice
The antigen used was a PspA-based fusion protein prepared in Example 1 (PspA3+2), and the adjuvant used was Alum. The following three groups were prepared.
   0.1 µg of PspA3+2+5.0 µg of Alum
   0.1 µg of PspA3+2+25.0 µg of Alum
   0.1 µg of PspA3+2+50.0 µg of Alum
An antigen solution was prepared in LPS-free PBS and subcutaneously injected into the mice for vaccination. The vaccination was performed every week, 3 times in total. One week after the final immunization (3rd vaccination), the blood was drawn from each mouse and the serum was separated.
(2) ELISA
ELISA was performed in the same manner as in Example 5, and the anti-PspA antibody titers of the antisera were determined.
(3) Results
The results are shown in FIG. 9. When Alum was used alone, the antibody titers against all of the PspAs of clades 1 to 5 were high. Even when the dose of Alum was as low as 5.0 which was the same amount as that in a combined use with CpG, the antibody titers were almost equivalent to those in the combined use.

Reference Example 1: PspA Family Distribution Among Pneumococcal Clinical Isolates in Japan The PspA family and clade distribution was examined among 73 adult invasive pneumococcal isolates collected in Japan. For the PspA family and clade identification, as is the case with Example 4, an about 400-bp nucleotide sequence upstream of the proline-rich region was compared with the corresponding sequences in the PspA genes of which the families and clades were already identified.

The results are shown in Table 5. All of the 145 strains were shown to bear a family 1 or 2 PspA. Among them, 126 isolates (86.9%) included the serotypes covered by the 23-valent pneumococcal polysaccharide vaccine (PPV23) for adults, 57 isolates (39.3%) included the serotypes covered by PCV7, and 108 isolates (74.5%) included the serotypes covered by PCV13.

TABLE 5

| Serotypes and PspA clades of pneumococcal clinical isolates in Japan | | | | | | | | | |
|---|---|---|---|---|---|---|---|---|---|
| | Coverage by current vaccines | | | Number of isolates | PspA family and Clade of each serotype (Number of isolates) | | | | |
| | | | | | Family 1 | | Family 2 | | Family 3 |
| Serotype | 23-valent | 7-valent | 13-valent | | Clade 1 | Clade 2 | Clade 3 | Clade 4 | Clade 5 | Clade 6 |
| 1 | + | | + | 1 | 1 | | | | | |
| 3 | + | | + | 42 | 37 | | 3 | 1 | 1 | |
| 4 | + | + | + | 12 | | | 11 | 1 | | |

TABLE 5-continued

Serotypes and PspA clades of pneumococcal clinical isolates in Japan

| Sero-type | Coverage by current vaccines | | | Number. of isolates | PspA family and Clade of each serotype (Number of isolates) | | | | | |
| --- | --- | --- | --- | --- | --- | --- | --- | --- | --- | --- |
| | 23-valent | 7-valent | 13-valent | | Family 1 | | Family 2 | | | Family 3 |
| | | | | | Clade 1 | Clade 2 | Clade 3 | Clade 4 | Clade 5 | Clade 6 |
| 6A | | | + | 3 | | 1 | 1 | | 1 | |
| 6B | + | + | + | 14 | 9 | | 5 | | | |
| 6C | | | | 4 | 1 | 3 | | | | |
| 7F | + | | + | 4 | | | 4 | | | |
| 9V | + | + | + | 4 | | | 4 | | | |
| 10A | + | | | 3 | 3 | | | | | |
| 11A | + | | | 2 | | | 1 | 1 | | |
| 12F | + | | | 2 | | | 2 | | | |
| 14 | + | + | + | 14 | 12 | 1 | | 1 | | |
| 15A | | | | 3 | 1 | | | 2 | | |
| 15B | + | | | 1 | | | 1 | | | |
| 16 | | | | 1 | | | 1 | | | |
| 18B | + | + | + | 1 | 1 | | | | | |
| 18C | + | | + | 1 | 1 | | | | | |
| 19A | + | + | + | 7 | | | 7 | | | |
| 19F | + | | | 5 | 2 | | 2 | | 1 | |
| 20 | + | | | 1 | 1 | | | | | |
| 22F | | | | 5 | 5 | | | | | |
| 23A | + | + | + | 2 | 1 | | | 1 | | |
| 23F | + | | | 7 | 1 | | | | 6 | |
| 33 | | | | 1 | 1 | | | | | |
| 34 | | | | 1 | 1 | | | | | |
| 35 | | | | 3 | | | | | 3 | |
| 38 | | | | 1 | | 1 | | | | |
| Total | | | | 145 | 78 (53.8%) | 6 (4.1%) | 42 (29%) | 10 (6.9%) | 9 (6.2%) | 0 |

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A pneumococcal vaccine for parenteral administration comprising a fusion protein comprising a full-length family 1, clade 2 pneumococcal surface protein A (PspA) or a fragment thereof, and a full-length family 2 PspA or a fragment thereof, wherein the full-length family 1, clade 2 PspA or a fragment thereof and the full-length family 2 PspA or a fragment thereof each comprises the whole of a proline-rich region and the whole or part of an α-helical region adjacent thereto, the fragment consists of 108 amino acid residues or more, and the fusion protein possesses the ability to induce protective immunity against pneumococcal infections in a living body, the fusion protein being any one of the following (1) to (3):

(1) a fusion protein at least comprising a full-length family 1, clade 2 PspA or a fragment thereof, and a full-length family 2, clade 3 PspA or a fragment thereof,
(2) a fusion protein at least comprising a full-length family 1, clade 2 PspA or a fragment thereof, and a full-length family 2, clade 4 PspA or a fragment thereof, and
(3) a fusion protein at least comprising a full-length family 1, clade 2 PspA or a fragment thereof, and a full-length family 2, clade 5 PspA or a fragment thereof.

2. The pneumococcal vaccine according to claim 1, wherein the fusion protein is any one of the following (4) to (6):

(4) a fusion protein consisting of a fragment of family 1, clade 2 PspA, and fragment of family 2, clade 3 PspA, wherein the fragment consists of the whole of a proline-rich region and the whole or part of an α-helical region adjacent thereto,
(5) a fusion protein consisting of a fragment of family 1, clade 2 PspA, and a fragment of family 2, clade 4 PspA, wherein the fragment consists of the whole of a proline-rich region and the whole or part of an α-helical region adjacent thereto, and
(6) a fusion protein consisting of a fragment of family 1, clade 2 PspA, and a fragment of family 2, clade 5 PspA, wherein the fragment consists of the whole of a proline-rich region and the whole or part of an α-helical region adjacent thereto.

3. The pneumococcal vaccine according to claim 1, wherein the family 1, clade 2 PspA is from a pneumococcal strain selected from the group consisting of D39, WU2, E134, EF10197, EF6796, BG9163 and DBL5.

4. The pneumococcal vaccine according to claim 1, wherein the family 2, clade 3 PspA is from a pneumococcal strain TIGR4, BG8090 or AC122, the family 2, clade 4 PspA is from a pneumococcal strain EF5668, BG7561, BG7817 or BG11703, and the family 2, clade 5 PspA is from a pneumococcal strain ATCC6303 or KK910.

5. The pneumococcal vaccine according to claim 1, wherein the fusion protein consists of an amino acid sequence at least 90% identical to SEQ ID NO: 1, 3 or 5.

6. A pneumococcal vaccine for parenteral administration comprising any one of the following (i) to (iii):

(i) a combination of only a fragment of family 1, clade 2 PspA and a fragment of family 2, clade 3 PspA, wherein the fragment consists of the whole of a proline-rich region and the whole or part of an α-helical region adjacent thereto,
(ii) a combination of only a fragment of family 1, clade 2 PspA and a fragment of family 2, clade 4 PspA, wherein the fragment consists of the whole of a proline-rich region and the whole or part of an α-helical region adjacent thereto, and
(iii) a combination of only a fragment of family 1, clade 2 PspA and a fragment of family 2, clade 5 PspA, wherein the fragment consists of the whole of a proline-rich region and the whole or part of an α-helical region adjacent thereto.

7. The pneumococcal vaccine according to claim 1, wherein the fusion protein is any one of the following (4) to (6):

(4) a fusion protein composed of a fragment consisting of the whole of α-helical and proline-rich regions of a D39 PspA, and a fragment consisting of the whole of α-helical and proline-rich regions of an EF5668 PspA,
(5) a fusion protein composed of a fragment consisting of the whole of α-helical and proline-rich regions of a D39 PspA, and a fragment consisting of the whole of α-helical and proline-rich regions of an ATCC6303 PspA, and
(6) a fusion protein composed of a fragment consisting of the whole of α-helical and proline-rich regions of a WU2 PspA, and a fragment consisting of the whole of α-helical and proline-rich regions of a TIGR4 PspA.

8. The pneumococcal vaccine according to claim 7, wherein the fusion protein is that described in the above (6).

9. The pneumococcal vaccine according to claim 5, wherein the fusion protein consists of an amino acid sequence at least 90% identical to SEQ ID NO: 5.

10. A method for prevention or treatment of pneumococcal disease, comprising parenterally administering, to an animal, an effective amount of a fusion protein comprising a full-length family 1, clade 2 PspA or a fragment thereof, and a full-length family 2 PspA or a fragment thereof, wherein the full-length family 1, clade 2 PspA or a fragment thereof and the full-length family 2 PspA or a fragment thereof each comprises the whole of a proline-rich region and the whole or part of an α-helical region adjacent thereto, the fragment consists of 108 amino acid residues or more, and the fusion protein possesses the ability to induce protective immunity against pneumococcal infections in a living body, the fusion protein being any one of the following (1) to (3):

(1) a fusion protein at least comprising a full-length family 1, clade 2 PspA or a fragment thereof, and a full-length family 2, clade 3 PspA or a fragment thereof,
(2) a fusion protein at least comprising a full-length family 1, clade 2 PspA or a fragment thereof, and a full-length family 2, clade 4 PspA or a fragment thereof, and
(3) a fusion protein at least comprising a full-length family 1, clade 2 PspA or a fragment thereof, and a full-length family 2, clade 5 PspA or a fragment thereof.

11. A method for prevention or treatment of pneumococcal disease, comprising parenterally administering, to an animal, effective amounts of at least the following components: a full-length family 1, clade 2 PspA or a fragment thereof, and a full-length family 2 PspA selected from the group consisting of clade 3, 4 and 5 PspAs, or a fragment thereof, wherein the full-length family 1, clade 2 PspA or a fragment thereof, and the full-length family 2 PspA selected from the group consisting of clade 3, 4 and 5 PspAs, or a fragment thereof each comprises the whole of a proline-rich region and the whole or part of an α-helical region adjacent thereto, the fragment consists of 108 amino acid residues or more, and the components possess the ability to induce protective immunity against pneumococcal infections in a living body.

12. The pneumococcal vaccine according to claim 1, further comprising an adjuvant.

13. The pneumococcal vaccine according to claim 1, further comprising a vaccine component against a pathogen other than pneumococci.

14. The method according to claim 10, wherein the fusion protein is any one of the following (4) to (6):
   (4) a fusion protein consisting of a fragment of family 1, clade 2 PspA, and a fragment of family 2, clade 3 PspA, wherein the fragment consists of the whole of a proline-rich region and the whole or part of an α-helical region adjacent thereto,
   (5) a fusion protein consisting of a fragment of family 1, clade 2 PspA, and h a fragment of family 2, clade 4 PspA, wherein the fragment consists of the whole of a proline-rich region and the whole or part of an α-helical region adjacent thereto, and
   (6) a fusion protein consisting of a fragment of family 1, clade 2 PspA, and a fragment of family 2, clade 5 PspA, wherein the fragment consists of the whole of a proline-rich region and the whole or part of an α-helical region adjacent thereto.

15. The method according to claim 10, wherein the fusion protein consists of an amino acid sequence at least 90% identical to SEQ ID NO: 1, 3 or 5.

16. The method according to claim 10, wherein the fusion protein is any one of the following (4) to (6):
   (4) a fusion protein composed of a fragment consisting of the whole of α-helical and proline-rich regions of a D39 PspA, and a fragment consisting of the whole of α-helical and proline-rich regions of an EF5668 PspA,
   (5) a fusion protein composed of a fragment consisting of the whole of α-helical and proline-rich regions of a D39 PspA, and a fragment consisting of the whole of α-helical and proline-rich regions of an ATCC6303 PspA, and
   (6) a fusion protein composed of a fragment consisting of the whole of α-helical and proline-rich regions of a WU2 PspA, and a fragment consisting of the whole of α-helical and proline-rich regions of a TIGR4 PspA.

17. The method according to claim 11, wherein the fragment of family 1, clade 2 PspA consists of an amino acid sequence at least 90% identical to SEQ ID NO: 25 or 26, the fragment of family 2, clade 3 PspA consists of an amino acid sequence at least 90% identical to SEQ ID NO: 27, the fragment of family 2, clade 4 PspA consists of an amino acid sequence at least 90% identical to SEQ ID NO: 28, and the fragment of family 2, clade 5 PspA consists of an amino acid sequence at least 90% identical to SEQ ID NO: 29.

* * * * *

```
                    SEQUENCE LISTING

<160> NUMBER OF SEQ ID NOS: 39

<210> SEQ ID NO 1
<211> LENGTH: 816
<212> TYPE: PRT
<213> ORGANISM: Artificial Sequence
<220> FEATURE:
<223> OTHER INFORMATION: Fusion type PspA

<400> SEQUENCE: 1

Met Gly Ser Ser His His His His His His Ser Ser Gly Leu Val Pro
1               5                   10                  15

Arg Gly Ser His Met Glu Glu Ser Pro Val Ala Ser Gln Ser Lys Ala
            20                  25                  30

Glu Lys Asp Tyr Asp Ala Ala Lys Lys Asp Ala Lys Asn Ala Lys Lys
        35                  40                  45

Ala Val Glu Asp Ala Gln Lys Ala Leu Asp Asp Ala Lys Ala Ala Gln
    50                  55                  60

Lys Lys Tyr Asp Glu Asp Gln Lys Lys Thr Glu Glu Lys Ala Ala Leu
65                  70                  75                  80

Glu Lys Ala Ala Ser Glu Glu Met Asp Lys Ala Val Ala Ala Val Gln
                85                  90                  95

Gln Ala Tyr Leu Ala Tyr Gln Gln Ala Thr Asp Lys Ala Ala Lys Asp
```

```
            100                 105                 110
Ala Ala Asp Lys Met Ile Asp Glu Ala Lys Lys Arg Glu Glu Glu Ala
            115                 120                 125

Lys Thr Lys Phe Asn Thr Val Arg Ala Met Val Val Pro Glu Pro Glu
            130                 135                 140

Gln Leu Ala Glu Thr Lys Lys Ser Glu Glu Ala Lys Gln Lys Ala
145                 150                 155                 160

Pro Glu Leu Thr Lys Lys Leu Glu Glu Ala Lys Ala Lys Leu Glu Glu
            165                 170                 175

Ala Glu Lys Lys Ala Thr Glu Ala Lys Gln Lys Val Asp Ala Glu Glu
            180                 185                 190

Val Ala Pro Gln Ala Lys Ile Ala Glu Leu Glu Asn Gln Val His Arg
            195                 200                 205

Leu Glu Gln Glu Leu Lys Glu Ile Asp Glu Ser Glu Ser Glu Asp Tyr
            210                 215                 220

Ala Lys Glu Gly Phe Arg Ala Pro Leu Gln Ser Lys Leu Asp Ala Lys
225                 230                 235                 240

Lys Ala Lys Leu Ser Lys Leu Glu Glu Leu Ser Asp Lys Ile Asp Glu
            245                 250                 255

Leu Asp Ala Glu Ile Ala Lys Leu Glu Asp Gln Leu Lys Ala Ala Glu
            260                 265                 270

Glu Asn Asn Asn Val Glu Asp Tyr Phe Lys Glu Gly Leu Glu Lys Thr
            275                 280                 285

Ile Ala Ala Lys Lys Ala Glu Leu Glu Lys Thr Glu Ala Asp Leu Lys
            290                 295                 300

Lys Ala Val Asn Glu Pro Glu Lys Pro Ala Pro Ala Pro Glu Thr Pro
305                 310                 315                 320

Ala Pro Glu Ala Pro Ala Glu Gln Pro Lys Pro Ala Pro Ala Pro Gln
            325                 330                 335

Pro Ala Pro Ala Pro Lys Pro Glu Lys Pro Ala Glu Gln Pro Lys Pro
            340                 345                 350

Glu Lys Thr Asp Asp Gln Gln Ala Glu Glu Asp Tyr Ala Arg Arg Ser
            355                 360                 365

Glu Glu Glu Tyr Asn Arg Leu Thr Gln Gln Gln Pro Pro Lys Ala Glu
            370                 375                 380

Lys Pro Ala Pro Ala Pro Lys Glu Phe Glu Glu Ala Pro Val Ala Asn
385                 390                 395                 400

Gln Ser Lys Ala Glu Lys Asp Tyr Asp Ala Ala Val Lys Lys Ser Glu
            405                 410                 415

Ala Ala Lys Lys Asp Tyr Glu Thr Ala Lys Lys Ala Glu Asp Ala
            420                 425                 430

Gln Lys Lys Tyr Asp Glu Asp Gln Lys Lys Thr Glu Ala Lys Ala Glu
            435                 440                 445

Lys Glu Arg Lys Ala Ser Glu Lys Ile Ala Glu Ala Thr Lys Glu Val
            450                 455                 460

Gln Gln Ala Tyr Leu Ala Tyr Leu Gln Ala Ser Asn Glu Ser Gln Arg
465                 470                 475                 480

Lys Glu Ala Asp Lys Lys Ile Lys Glu Ala Thr Gln Arg Lys Asp Glu
            485                 490                 495

Ala Glu Ala Ala Phe Ala Thr Ile Arg Thr Thr Ile Val Val Pro Glu
            500                 505                 510

Pro Ser Glu Leu Ala Glu Thr Lys Lys Lys Ala Glu Glu Ala Thr Lys
            515                 520                 525
```

Glu Ala Glu Val Ala Lys Lys Ser Glu Glu Ala Lys Glu Val
    530                 535                 540
Glu Val Glu Lys Asn Lys Ile Leu Glu Gln Asp Ala Glu Asn Glu Lys
545                 550                 555                 560
Lys Ile Asp Val Leu Gln Asn Lys Val Ala Asp Leu Glu Lys Gly Ile
                565                 570                 575
Ala Pro Tyr Gln Asn Glu Val Ala Glu Leu Asn Lys Glu Ile Ala Arg
            580                 585                 590
Leu Gln Ser Asp Leu Lys Asp Ala Glu Glu Asn Asn Val Glu Asp Tyr
        595                 600                 605
Ile Lys Glu Gly Leu Glu Gln Ala Ile Thr Asn Lys Lys Ala Glu Leu
    610                 615                 620
Ala Thr Thr Gln Gln Asn Ile Asp Lys Thr Gln Lys Asp Leu Glu Asp
625                 630                 635                 640
Ala Glu Leu Glu Leu Glu Lys Val Leu Ala Thr Leu Asp Pro Glu Gly
                645                 650                 655
Lys Thr Gln Asp Glu Leu Asp Lys Glu Ala Ala Glu Ala Glu Leu Asn
            660                 665                 670
Glu Lys Val Glu Ala Leu Gln Asn Gln Val Ala Glu Leu Glu Glu Glu
        675                 680                 685
Leu Ser Lys Leu Glu Asp Asn Leu Lys Asp Ala Glu Thr Asn Asn Val
    690                 695                 700
Glu Asp Tyr Ile Lys Glu Gly Leu Glu Ala Ile Ala Thr Lys Lys
705                 710                 715                 720
Ala Glu Leu Glu Lys Thr Gln Lys Glu Leu Asp Ala Ala Leu Asn Glu
                725                 730                 735
Leu Gly Pro Asp Gly Asp Glu Glu Thr Pro Ala Pro Ala Pro Gln
            740                 745                 750
Pro Glu Lys Pro Ala Glu Pro Glu Asn Pro Ala Pro Ala Pro Lys
        755                 760                 765
Pro Glu Lys Ser Ala Asp Gln Gln Ala Glu Glu Asp Tyr Ala Arg Arg
    770                 775                 780
Ser Glu Glu Glu Tyr Asn Arg Leu Thr Gln Gln Pro Pro Lys Ala
785                 790                 795                 800
Glu Lys Pro Ala Pro Ala Pro Gln Pro Glu Gln Pro Ala Pro Ala Pro
                805                 810                 815

<210> SEQ ID NO 2
<211> LENGTH: 2451
<212> TYPE: DNA
<213> ORGANISM: Artificial Sequence
<220> FEATURE:
<223> OTHER INFORMATION: Fusion type PspA

<400> SEQUENCE: 2
atgggcagca gccatcatca tcatcatcac agcagcggcc tggtgccgcg cggcagccat      60
atggaagaat ctcccgtagc cagtcagtct aaagctgaga agactatga tgcagcgaag     120 aaagatgcta agaatgcgaa aaaagcagta gaagatgctc aaaaggcttt agatgatgca     180
aaagctgctc agaaaaaata tgacgaggat cagaagaaaa ctgaggagaa agccgcgcta     240
gaaaaagcag cgtctgaaga gatggataag gcagtggcag cagttcaaca agcgtatcta     300
gcctatcaac aagctacaga caaagccgca aagacgcag cagataagat gatagatgaa     360
gctaagaaac gcgaagaaga ggcaaaaact aaatttaata ctgttcgagc aatggtagtt     420

```
cctgagccag agcagttggc tgagactaag aaaaaatcag aagaagctaa acaaaaagca      480
ccagaactta ctaaaaaact agaagaagct aaagcaaaat tagaagaggc tgagaaaaaa      540
gctactgaag ccaaacaaaa agtggatgct gaagaagtcg ctcctcaagc taaaatcgct      600
gaattggaaa atcaagttca tagactagaa caagagctca aagagattga tgagtctgaa      660
tcagaagatt atgctaaaga aggtttccgt gctcctcttc aatctaaatt ggatgccaaa      720
aaagctaaac tatcaaaact tgaagagtta agtgataaga ttgatgagtt agacgctgaa      780
attgcaaaac ttgaagatca acttaaagct gctgaagaaa acaataatgt agaagactac      840
tttaaagaag gtttagagaa aactattgct gctaaaaaag ctgaattaga aaaaactgaa      900
gctgacctta agaaagcagt taatgagcca gaaaaaccag ctccagctcc agaaactcca      960
gccccagaag caccagctga acaaccaaaa ccagcgccgg ctcctcaacc agctcccgca     1020
ccaaaaccag agaagccagc tgaacaacca aaaccagaaa aaacagatga tcaacaagct     1080
gaagaagact atgctcgtag atcagaagaa gaatataatc gcttgactca acagcaaccg     1140
ccaaaagctg aaaaaccagc tcctgcacca aaagaattcg aagaagctcc tgtagctaac     1200
cagtctaaag ctgagaaaga ctatgatgca gcagtgaaaa aatctgaagc tgctaagaaa     1260
gattacgaaa cggctaaaaa agaaagcaga gacgctcaga gaaatatga tgaggatcag      1320 aagaaaactg aggcaaaagc ggaaaaagaa agaaaagctt ctgaaaagat agctgaggca     1380
acaaaagaag ttcaacaagc gtacctagct tatctacaag ctagcaacga aagtcagaga     1440
aaagaggcag ataagaagat aaaagaagct acgcaacgca aagatgaggc ggaagctgca     1500
tttgctacta ttcgaacaac aattgtagtt cctgaaccaa gtgagttagc tgagactaag     1560
aaaaaagcag aagaggcaac aaaagaagca gaagtagcta gaaaaaaatc tgaagaggca     1620 gctaagagg tagaagtaga gaaaaataaa atacttgaac aagatgctga aaacgaaaag      1680
aaaattgacg tacttcaaaa caagtcgct gatttagaaa aggaattgc tccttatcaa       1740 aacgaagtcg ctgaattaaa taagaaatt gctagacttc aaagcgattt aaaagatgct     1800
gaagaaaata atgtagaaga ctacattaaa gaaggtttag agcaagctat cactaataaa     1860
aaagctgaat tagctacaac tcaacaaaac atagataaaa ctcaaaaaga tttagaggat     1920
gctgaattag aacttgaaaa agtattagct acattagacc ctgaaggtaa aactcaagat     1980
gaattagata agaagctgc tgaagctgag ttgaatgaaa aagttgaagc tcttcaaaac      2040
caagttgctg aattagaaga gaactttca aaacttgaag ataatcttaa agatgctgaa      2100
acaaacaacg ttgaagacta cattaaagaa ggtttagaag aagctatcgc gactaaaaaa     2160
gctgaattgg aaaaaactca aaaagaatta gatgcagctc ttaatgagtt aggccctgat     2220
ggagatgaag aagagactcc agcgccggct cctcaaccag aaaaaccagc tgaagagcct     2280
gagaatccag ctccagcacc aaaaccagag aagtcagcag atcaacaagc tgaagaagac     2340
tatgctcgta gatcagaaga agaatataat cgcttgaccc aacagcaacc gccaaaagca     2400
gaaaaaccag ctcctgcacc acaaccagag caaccagctc ctgcaccata a              2451
```

<210> SEQ ID NO 3
<211> LENGTH: 823
<212> TYPE: PRT
<213> ORGANISM: Artificial Sequence
<220> FEATURE:
<223> OTHER INFORMATION: Fusion type PspA

<400> SEQUENCE: 3

Met Gly Ser Ser His His His His His His Ser Ser Gly Leu Val Pro

-continued

```
1               5                   10                  15
Arg Gly Ser His Met Glu Glu Ser Pro Val Ala Ser Gln Ser Lys Ala
                20                  25                  30
Glu Lys Asp Tyr Asp Ala Ala Lys Lys Asp Ala Lys Asn Ala Lys Lys
                35                  40                  45
Ala Val Glu Asp Ala Gln Lys Ala Leu Asp Asp Ala Lys Ala Ala Gln
     50                  55                  60
Lys Lys Tyr Asp Glu Asp Gln Lys Lys Thr Glu Lys Ala Ala Leu
 65                  70                  75                  80
Glu Lys Ala Ala Ser Glu Glu Met Asp Lys Ala Val Ala Ala Val Gln
                 85                  90                  95
Gln Ala Tyr Leu Ala Tyr Gln Gln Ala Thr Asp Lys Ala Ala Lys Asp
                100                 105                 110
Ala Ala Asp Lys Met Ile Asp Glu Ala Lys Lys Arg Glu Glu Glu Ala
                115                 120                 125
Lys Thr Lys Phe Asn Thr Val Arg Ala Met Val Val Pro Glu Pro Glu
                130                 135                 140
Gln Leu Ala Glu Thr Lys Lys Ser Glu Glu Ala Lys Gln Lys Ala
145                 150                 155                 160
Pro Glu Leu Thr Lys Lys Leu Glu Glu Ala Lys Ala Lys Leu Glu Glu
                165                 170                 175
Ala Glu Lys Lys Ala Thr Glu Ala Lys Gln Lys Val Asp Ala Glu Glu
                180                 185                 190
Val Ala Pro Gln Ala Lys Ile Ala Glu Leu Glu Asn Gln Val His Arg
                195                 200                 205
Leu Glu Gln Glu Leu Lys Glu Ile Asp Glu Ser Glu Ser Glu Asp Tyr
    210                 215                 220
Ala Lys Glu Gly Phe Arg Ala Pro Leu Gln Ser Lys Leu Asp Ala Lys
225                 230                 235                 240
Lys Ala Lys Leu Ser Lys Leu Glu Glu Leu Ser Asp Lys Ile Asp Glu
                245                 250                 255
Leu Asp Ala Glu Ile Ala Lys Leu Glu Asp Gln Leu Lys Ala Ala Glu
                260                 265                 270
Glu Asn Asn Asn Val Glu Asp Tyr Phe Lys Glu Gly Leu Glu Lys Thr
                275                 280                 285
Ile Ala Ala Lys Lys Ala Glu Leu Glu Lys Thr Glu Ala Asp Leu Lys
                290                 295                 300
Lys Ala Val Asn Glu Pro Glu Lys Pro Ala Pro Ala Pro Glu Thr Pro
305                 310                 315                 320
Ala Pro Glu Ala Pro Ala Glu Gln Pro Lys Pro Ala Pro Ala Pro Gln
                325                 330                 335
Pro Ala Pro Ala Pro Lys Pro Glu Lys Pro Ala Glu Gln Pro Lys Pro
                340                 345                 350
Glu Lys Thr Asp Asp Gln Gln Ala Glu Glu Asp Tyr Ala Arg Arg Ser
                355                 360                 365
Glu Glu Glu Tyr Asn Arg Leu Thr Gln Gln Gln Pro Pro Lys Ala Glu
                370                 375                 380
Lys Pro Ala Pro Ala Pro Lys Glu Phe Glu Glu Ser Pro Gln Val Val
385                 390                 395                 400
Glu Lys Ser Ser Leu Glu Lys Lys Tyr Glu Glu Ala Lys Ala Lys Ala
                405                 410                 415
Asp Thr Ala Lys Lys Asp Tyr Glu Thr Ala Lys Lys Ala Glu Asp
                420                 425                 430
```

```
Ala Gln Lys Lys Tyr Asp Glu Asp Gln Lys Lys Thr Glu Asp Lys Ala
        435                 440                 445
Lys Ala Val Lys Lys Val Asp Glu Glu Arg Gln Lys Ala Asn Leu Ala
    450                 455                 460
Val Gln Lys Ala Tyr Val Glu Tyr Arg Glu Ala Lys Asp Lys Ala Ser
465                 470                 475                 480
Ala Glu Lys Lys Ile Glu Ala Lys Arg Lys Gln Lys Glu Ala Asn
                485                 490                 495
Lys Lys Phe Asn Glu Glu Gln Ala Lys Val Val Pro Glu Ala Lys Glu
            500                 505                 510
Leu Ala Ala Thr Lys Gln Lys Ala Glu Lys Ala Lys Asp Ala Glu
            515                 520                 525
Val Ala Lys Glu Lys Tyr Asp Lys Ala Val Gln Glu Val Glu Val Glu
    530                 535                 540
Lys Asn Lys Ile Leu Glu Gln Asp Ala Glu Asn Glu Lys Lys Ile Asp
545                 550                 555                 560
Val Leu Gln Asn Lys Val Ala Asp Leu Glu Lys Gly Ile Ala Pro Tyr
                565                 570                 575
Gln Asn Lys Val Ala Glu Leu Asn Lys Glu Ile Ala Arg Leu Gln Ser
            580                 585                 590
Asp Leu Lys Asp Ala Glu Glu Asn Asn Val Glu Asp Tyr Ile Lys Glu
            595                 600                 605
Gly Leu Glu Gln Ala Ile Ala Asp Lys Lys Ala Glu Leu Ala Thr Thr
    610                 615                 620
Gln Gln Asn Ile Asp Lys Thr Gln Lys Asp Leu Glu Asp Ala Glu Leu
625                 630                 635                 640
Glu Leu Glu Lys Val Leu Ala Thr Leu Asp Pro Glu Gly Lys Thr Gln
                645                 650                 655
Asp Glu Leu Asp Lys Glu Ala Ala Glu Asp Ala Asn Ile Glu Ala Leu
            660                 665                 670
Gln Asn Lys Val Ala Asp Leu Glu Asn Lys Val Ala Glu Leu Asp Lys
            675                 680                 685
Glu Val Thr Arg Leu Gln Ser Asp Leu Lys Asp Ala Glu Glu Asn Asn
    690                 695                 700
Val Glu Asp Tyr Val Lys Glu Gly Leu Glu Lys Ala Leu Thr Asp Lys
705                 710                 715                 720
Lys Val Glu Leu Asn Asn Thr Gln Lys Ala Leu Asp Thr Ala Gln Lys
                725                 730                 735
Ala Leu Asp Thr Ala Leu Asn Glu Leu Gly Pro Asp Gly Asp Glu Glu
            740                 745                 750
Glu Thr Pro Ala Pro Ala Pro Lys Pro Glu Gln Pro Ala Glu Gln Pro
            755                 760                 765
Lys Pro Ala Pro Ala Pro Lys Pro Glu Lys Thr Asp Asp Gln Gln Ala
    770                 775                 780
Glu Glu Asp Tyr Ala Arg Arg Ser Glu Glu Tyr Asn Arg Leu Pro
785                 790                 795                 800
Gln Gln Gln Pro Pro Lys Ala Glu Lys Pro Ala Pro Ala Pro Lys Pro
                805                 810                 815
Glu Gln Pro Val Pro Ala Pro
            820

<210> SEQ ID NO 4
<211> LENGTH: 2472
```

<212> TYPE: DNA
<213> ORGANISM: Artificial Sequence
<220> FEATURE:
<223> OTHER INFORMATION: Fusion type PspA

<400> SEQUENCE: 4

| | | | | | | |
|---|---|---|---|---|---|---|
| atgggcagca | gccatcatca | tcatcatcac | agcagcggcc | tggtgccgcg | cggcagccat | 60 |
| atggaagaat | ctcccgtagc | cagtcagtct | aaagctgaga | agactatga | tgcagcgaag | 120 |
| aaagatgcta | agaatgcgaa | aaaagcagta | gaagatgctc | aaaaggcttt | agatgatgca | 180 |
| aaagctgctc | agaaaaaata | tgacgaggat | cagaagaaaa | ctgaggagaa | agccgcgcta | 240 |
| gaaaaagcag | cgtctgaaga | gatggataag | gcagtggcag | cagttcaaca | agcgtatcta | 300 |
| gcctatcaac | aagctacaga | caaagccgca | aaagacgcag | cagataagat | gatagatgaa | 360 |
| gctaagaaac | gcgaagaaga | ggcaaaaact | aaatttaata | ctgttcgagc | aatggtagtt | 420 |
| cctgagccag | agcagttggc | tgagactaag | aaaaaatcag | aagaagctaa | caaaaagca | 480 |
| ccagaactta | ctaaaaaact | agaagaagct | aaagcaaaat | tagaagaggc | tgagaaaaaa | 540 |
| gctactgaag | ccaaacaaaa | agtggatgct | gaagaagtcg | ctcctcaagc | taaaatcgct | 600 |
| gaattggaaa | atcaagttca | tagactagaa | caagagctca | aagagattga | tgagtctgaa | 660 |
| tcagaagatt | atgctaaaga | aggtttccgt | gctcctcttc | aatctaaatt | ggatgccaaa | 720 |
| aaagctaaac | tatcaaaact | tgaagagtta | agtgataaga | ttgatgagtt | agacgctgaa | 780 |
| attgcaaaac | ttgaagatca | acttaaagct | gctgaagaaa | acaataatgt | agaagactac | 840 |
| tttaaagaag | gtttagagaa | aactattgct | gctaaaaaag | ctgaattaga | aaaaactgaa | 900 |
| gctgacctta | agaaagcagt | taatgagcca | gaaaaaccag | ctccagctcc | agaaactcca | 960 |
| gccccagaag | caccagctga | caaccaaaa | ccagcgccgg | ctcctcaacc | agctcccgca | 1020 |
| ccaaaaccag | agaagccagc | tgaacaacca | aaaccagaaa | aaacagatga | tcaacaagct | 1080 |
| gaagaagact | atgctcgtag | atcagaagaa | gaatataatc | gcttgactca | acagcaaccg | 1140 |
| ccaaaagctg | aaaaaccagc | tcctgcacca | aaagaattcg | aagaatctcc | acaagttgtc | 1200 |
| gaaaaatctt | cattagagaa | gaaatatgag | gaagcaaaag | caaaagctga | tactgccaag | 1260 |
| aaagattacg | aaacggctaa | aaagaaagca | gaagacgctc | agaagaaata | tgatgaggat | 1320 |
| cagaagaaaa | ctgaggataa | ggcaaaagcg | gttaagaaag | ttgatgaaga | acgtcaaaaa | 1380 |
| gcgaatttgg | cagttcaaaa | ggcgtatgta | gaatatagag | aagcgaaaga | taagctagc | 1440 |
| gctgagaaaa | agattgaaga | agcaaaacga | aacaaaaag | aagcgaacaa | aaaatttaat | 1500 |
| gaggagcaag | caaagtagt | tcctgaagca | aaggagttag | ctgctactaa | acaaaaagcg | 1560 |
| gaaaaagcta | aaaagacgc | cgaagtagct | aaggaaaaat | atgataaggc | agttcaagag | 1620 |
| gtagaagtag | agaaaaataa | aatacttgaa | caagatgctg | aaaacgaaaa | gaaaattgac | 1680 |
| gtacttcaaa | acaagtcgc | tgatttagaa | aaggaattg | ctccttatca | aaacaaagtc | 1740 |
| gctgaattaa | ataagaaat | tgctagactt | caaagcgatt | taaaagatgc | tgaagaaat | 1800 |
| aatgtagaag | actatattaa | agaaggttta | gagcaagcta | tcgctgataa | aaagctgaa | 1860 |
| ttagctacaa | ctcaacaaaa | catagataaa | actcaaaaag | atttagagga | tgctgaatta | 1920 |
| gaacttgaaa | aagtattagc | tacattagac | cctgaaggta | aactcaaga | tgaattagat | 1980 |
| aagaagctg | cagaagatgc | taatattgaa | gctcttcaaa | acaaagttgc | tgatctagaa | 2040 |
| aacaaggttg | ctgaattaga | taaagaagtt | actagacttc | aaagcgattt | aaagatgct | 2100 |
| gaagaaaaca | atgtagaaga | ctacgttaaa | gaaggcttag | agaaagctct | tactgataaa | 2160 |

-continued

```
aaagttgaat taaataatac tcaaaaagca ttagatactg ctcaaaaagc attagatact    2220
gctcttaatg aattaggtcc tgacggtgat gaagaagaaa ctccagctcc agcaccaaaa    2280
ccagagcaac cagctgaaca accaaaacca gctccagcac caaaaccaga aaaacagat     2340 gatcaacaag ctgaagaaga ctatgctcgt agatcagaag aagaatataa ccgcttgccc    2400
caacagcaac cgccaaaagc agaaaaacca gctccagcac caaaaccaga gcaaccagtt    2460
cctgcaccat aa                                                        2472
```

<210> SEQ ID NO 5
<211> LENGTH: 894
<212> TYPE: PRT
<213> ORGANISM: Artificial Sequence
<220> FEATURE:
<223> OTHER INFORMATION: Fusion type PspA

<400> SEQUENCE: 5

```
Met Gly Ser Ser His His His His His His Ser Ser Gly Leu Val Pro
1               5                   10                  15

Arg Gly Ser His Met Glu Glu Ser Pro Gln Val Val Glu Lys Ser Ser
            20                  25                  30

Leu Glu Lys Lys Tyr Glu Glu Ala Lys Ala Lys Ala Asp Thr Ala Lys
        35                  40                  45

Lys Asp Tyr Glu Thr Ala Lys Lys Ala Glu Asp Ala Gln Lys Lys
    50                  55                  60

Tyr Glu Asp Asp Gln Lys Arg Thr Glu Glu Lys Ala Arg Lys Glu Ala
65                  70                  75                  80

Glu Ala Ser Gln Lys Leu Asn Asp Val Ala Leu Val Val Gln Asn Ala
                85                  90                  95

Tyr Lys Glu Tyr Arg Glu Val Gln Asn Gln Arg Ser Lys Tyr Lys Ser
            100                 105                 110

Asp Ala Glu Tyr Gln Lys Lys Leu Thr Glu Val Asp Ser Lys Ile Glu
        115                 120                 125

Lys Ala Arg Lys Glu Gln Gln Asp Leu Gln Asn Lys Phe Asn Glu Val
    130                 135                 140

Arg Ala Val Val Val Pro Glu Pro Asn Ala Leu Ala Glu Thr Lys Lys
145                 150                 155                 160

Lys Ala Glu Glu Ala Lys Ala Glu Glu Lys Val Ala Lys Arg Lys Tyr
                165                 170                 175

Asp Tyr Ala Thr Leu Lys Val Ala Leu Ala Lys Lys Glu Val Glu Ala
            180                 185                 190

Lys Glu Leu Glu Ile Glu Lys Leu Gln Tyr Glu Ile Ser Thr Leu Glu
        195                 200                 205

Gln Glu Val Ala Thr Ala Gln His Gln Val Asp Asn Leu Lys Lys Leu
    210                 215                 220

Leu Ala Gly Ala Asp Pro Asp Asp Gly Thr Glu Val Ile Glu Ala Lys
225                 230                 235                 240

Leu Lys Lys Gly Glu Ala Glu Leu Asn Ala Lys Gln Ala Glu Leu Ala
                245                 250                 255

Lys Lys Gln Thr Glu Leu Glu Lys Leu Leu Asp Ser Leu Asp Pro Glu
            260                 265                 270

Gly Lys Thr Gln Asp Glu Leu Asp Lys Glu Ala Glu Ala Glu Leu
        275                 280                 285

Asp Lys Lys Ala Asp Glu Leu Gln Asn Lys Val Ala Asp Leu Glu Lys
    290                 295                 300
```

-continued

```
Glu Ile Ser Asn Leu Glu Ile Leu Leu Gly Gly Ala Asp Pro Glu Asp
305                 310                 315                 320
Asp Thr Ala Ala Leu Gln Asn Lys Leu Ala Ala Lys Lys Ala Glu Leu
                325                 330                 335
Ala Lys Lys Gln Thr Glu Leu Glu Lys Leu Leu Asp Ser Leu Asp Pro
            340                 345                 350
Glu Gly Lys Thr Gln Asp Glu Leu Asp Lys Glu Ala Glu Glu Ala Glu
        355                 360                 365
Leu Asp Lys Lys Ala Asp Glu Leu Gln Asn Lys Val Ala Asp Leu Glu
    370                 375                 380
Lys Glu Ile Ser Asn Leu Glu Ile Leu Leu Gly Gly Ala Asp Ser Glu
385                 390                 395                 400
Asp Asp Thr Ala Ala Leu Gln Asn Lys Leu Ala Thr Lys Lys Ala Glu
                405                 410                 415
Leu Glu Lys Thr Gln Lys Glu Leu Asp Ala Ala Leu Asn Glu Leu Gly
            420                 425                 430
Pro Asp Gly Asp Glu Glu Thr Pro Ala Pro Ala Gln Pro Glu
        435                 440                 445
Gln Pro Ala Pro Ala Pro Lys Pro Glu Gln Pro Ala Pro Ala Pro Lys
450                 455                 460
Pro Glu Gln Pro Ala Pro Ala Pro Lys Pro Glu Gln Pro Ala Pro Ala
465                 470                 475                 480
Pro Lys Pro Glu Gln Pro Ala Pro Ala Pro Lys Pro Glu Gln Pro Ala
                485                 490                 495
Lys Pro Glu Lys Pro Ala Glu Glu Pro Thr Gln Pro Glu Lys Pro Ala
            500                 505                 510
Thr Pro Glu Phe Glu Glu Ser Pro Val Ala Ser Gln Ser Lys Ala Glu
            515                 520                 525
Lys Asp Tyr Asp Ala Ala Val Lys Lys Ser Glu Ala Ala Lys Lys Ala
        530                 535                 540
Tyr Glu Glu Ala Lys Lys Ala Leu Glu Glu Ala Lys Val Ala Gln Lys
545                 550                 555                 560
Lys Tyr Glu Asp Asp Gln Lys Lys Thr Glu Glu Lys Ala Glu Leu Glu
                565                 570                 575
Lys Glu Ala Ser Glu Ala Ile Ala Lys Ala Thr Glu Glu Val Gln Gln
            580                 585                 590
Ala Tyr Leu Ala Tyr Gln Arg Ala Ser Asn Lys Ala Glu Ala Ala Lys
        595                 600                 605
Met Ile Glu Glu Ala Gln Arg Arg Glu Asn Glu Ala Arg Ala Lys Phe
610                 615                 620
Thr Thr Ile Arg Thr Thr Met Val Val Pro Glu Pro Glu Gln Leu Ala
625                 630                 635                 640
Glu Thr Lys Lys Lys Ala Glu Glu Ala Lys Ala Lys Glu Pro Lys Leu
                645                 650                 655
Ala Lys Lys Ala Ala Glu Ala Lys Ala Lys Leu Glu Glu Ala Glu Lys
            660                 665                 670
Lys Ala Thr Glu Ala Lys Gln Lys Val Asp Ala Glu Glu Val Ala Pro
        675                 680                 685
Gln Ala Lys Ile Ala Glu Glu Leu Glu Asn Gln Val His Arg Leu Glu Gln
    690                 695                 700
Glu Leu Lys Glu Ile Asp Glu Ser Glu Ser Glu Asp Tyr Ala Lys Glu
705                 710                 715                 720
Gly Phe Arg Ala Pro Leu Gln Ser Lys Leu Asp Ala Lys Lys Ala Lys
```

```
                725                 730                 735
Leu Ser Lys Leu Glu Glu Leu Ser Asp Lys Ile Asp Glu Leu Asp Ala
            740                 745                 750

Glu Ile Ala Lys Leu Glu Asp Gln Leu Lys Ala Ala Glu Glu Asn Asn
        755                 760                 765

Asn Val Glu Asp Tyr Phe Lys Glu Gly Leu Glu Lys Thr Ile Ala Ala
    770                 775                 780

Lys Lys Ala Glu Leu Glu Lys Thr Glu Ala Asp Leu Lys Lys Ala Val
785                 790                 795                 800

Asn Glu Pro Glu Lys Ser Ala Glu Glu Pro Ser Gln Pro Glu Lys Pro
                805                 810                 815

Ala Glu Glu Ala Pro Ala Pro Glu Gln Pro Thr Glu Pro Thr Gln Pro
            820                 825                 830

Glu Lys Pro Ala Glu Glu Thr Pro Ala Pro Lys Pro Glu Lys Pro Ala
        835                 840                 845

Glu Gln Pro Lys Ala Glu Lys Thr Asp Asp Gln Gln Ala Glu Glu Asp
    850                 855                 860

Tyr Ala Arg Arg Ser Glu Glu Glu Tyr Asn Arg Leu Thr Gln Gln Gln
865                 870                 875                 880

Pro Pro Lys Ala Glu Lys Pro Ala Pro Ala Pro Gln Pro Glu
                885                 890

<210> SEQ ID NO 6
<211> LENGTH: 2685
<212> TYPE: DNA
<213> ORGANISM: Artificial Sequence
<220> FEATURE:
<223> OTHER INFORMATION: Fusion type PspA

<400> SEQUENCE: 6
atgggcagca gccatcatca tcatcatcac agcagcggcc tggtgccgcg cggcagccat      60
atggaagaat ctccacaagt tgtcgaaaaa tcttcattag agaagaaata tgaggaagca     120
aaagcaaaag ctgatactgc caagaaagat tacgaaacgg ctaaaagaa agcagaagac      180 gctcagaaaa agtatgaaga tgatcagaag agaactgagg agaaagctcg aaaagaagca     240
gaagcatctc aaaaattgaa tgatgtggcg cttgttgttc aaaatgcata taaagagtac     300
cgagaagttc aaaatcaacg tagtaaatat aaatctgacg ctgaatatca gaaaaaatta     360
acagaggtcg actctaaaat agagaaggct aggaagagc aacaggactt gcaaaataaa     420
tttaatgaag taagagcagt tgtagttcct gaaccaaatg cgttggctga gactaagaaa     480
aaagcagaag aagctaaagc agaagaaaaa gtagctaaga gaaaatatga ttatgcaact     540
ctaaaggtag cactagcgaa gaagaagta gaggctaagg aacttgaaat tgaaaaactt     600
caatatgaaa tttctacttt ggaacaagaa gttgctactg ctcaacatca gtagataat     660 ttgaaaaaac ttcttgctgg tgcggatcct gatgatggca cagaagttat agaagctaaa     720
ttaaaaaaag gagaagctga gctaaacgct aaacaagctg agttagcaaa aaacaaaca     780 gaacttgaaa acttcttga cagccttgat cctgaaggta agactcagga tgaattagat     840
aaagaagcag aagaagctga gttggataaa aaagctgatg aacttcaaaa taaagttgct     900
gatttagaaa agaaattag taaccttgaa atattacttg aggggctga tcctgaagat     960 gatactgctg ctcttcaaaa taaattagct gctaaaaaag ctgagttagc aaaaaaacaa    1020
acagaacttg aaaaacttct tgacagccct tgatcctgaag gtaagactca ggatgaatta    1080
gataaagaag cagaagaagc tgagttggat aaaaaagctg atgaacttca aaataaagtt    1140
```

```
gctgatttag aaaaagaaat tagtaacctt gaaatattac ttggaggggc tgattctgaa   1200
gatgatactg ctgctcttca aaataaatta gctactaaaa aagctgaatt ggaaaaaact   1260
caaaaagaat tagatgcagc tcttaatgag ttaggccctg atggagatga agaagaaact   1320
ccagcgccgg ctcctcaacc agagcaacca gctcctgcac caaaaccaga gcaaccagct   1380
ccagctccaa aaccagagca accagctcct gcaccaaaac cagagcaacc agctccagct   1440
ccaaaaccag agcaaccagc tccagctcca aaaccagagc aaccagctaa gccggagaaa   1500
ccagctgaag agcctactca accagaaaaa ccagccactc agaattcga agaatctccc    1560 gtagctagtc agtctaaagc tgagaaagac tatgatgcag cagtgaaaaa atctgaagct   1620
gctaagaagg cttacgaaga agctaaaaaa gctttagagg aagcaaaagt tgcgcaaaaa   1680
aaatatgaag acgatcaaaa gaaaactgaa gagaaagcag agctagaaaa agaagcttct   1740
gaagcgatag ctaaggcaac agaagaagtt caacaagcgt acctagctta tcaacgagct   1800
agcaacaaag ccgaagcagc taagatgata gaagaggctc agagacgcga aaatgaggcg   1860
agagctaaat ttactactat tcgaacaaca atggtagttc ctgaaccaga acagttagct   1920
gagactaaga aaaaagcaga agaagctaaa gcaaaagaac caaaacttgc taaaaaagca   1980
gcagaagcta aagcaaaatt agaagaggct gagaaaaaag ctactgaagc caaacaaaaa   2040
gtggatgctg aagaagtcgc tcctcaagct aaaatcgctg aattggaaaa tcaagttcat   2100
agactagaac aagagctcaa agagattgat gagtctgaat cagaagatta tgctaaagaa   2160
ggtttccgtg ctcctcttca atctaaattg gatgccaaaa aagctaaact atcaaaactt   2220
gaagagttaa gtgataagat tgatgagtta gacgctgaaa ttgcaaaact tgaagatcaa   2280
cttaaagctg ctgaagaaaa caataatgta gaagactact ttaaagaagg tttagagaaa   2340
actattgctg ctaaaaaagc tgaattagaa aaaactgaag ctgaccttaa gaaagcagtt   2400
aatgagccag aaaaatcagc tgaagagcca tcgcaaccag agaagccagc tgaagaagct   2460
ccagccccag agcaaccaac tgagccaact caaccagaaa aaccagctga agaaactcca   2520
gcaccaaaac cagagaagcc agctgaacaa ccaaaagcag aaaaaacaga tgatcaacaa   2580
gctgaagaag actatgctcg tagatcagaa gaagaatata atcgcttgac tcaacagcaa   2640
ccgccaaaag cagaaaaacc agctcctgca ccacaaccag agtaa                  2685
```

```
<210> SEQ ID NO 7
<211> LENGTH: 34
<212> TYPE: DNA
<213> ORGANISM: Artificial Sequence
<220> FEATURE:
<223> OTHER INFORMATION: Primer

<400> SEQUENCE: 7
ggaattccat atggaagaat ctcccgtagc cagt                              34

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
ggaattcttt tggtgcagga gctgg                                        25

<210> SEQ ID NO 9
```

```
<211> LENGTH: 27
<212> TYPE: DNA
<213> ORGANISM: Artificial Sequence
<220> FEATURE:
<223> OTHER INFORMATION: Primer

<400> SEQUENCE: 9
ggaattcgaa gaatctcccg tagctag                                             27

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
ccgctcgagt tagtgcaagg agctggtttg                                          30

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
ggaattcgaa gaatctccac aagttgtcg                                           29

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
ccgctcgagt tatggtgcag gaactggttg                                          30

<210> SEQ ID NO 13
<211> LENGTH: 34
<212> TYPE: DNA
<213> ORGANISM: Artificial Sequence
<220> FEATURE:
<223> OTHER INFORMATION: Primer

<400> SEQUENCE: 13
ggaattccat atggaagaat ctccacaagt tgtc                                     34

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14
ggaattctgg agtggctggt ttttctg                                             27

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
```
ggaattcgaa gaatctcccg tagctag                                          27

<210> SEQ ID NO 16
<211> LENGTH: 39
<212> TYPE: DNA
<213> ORGANISM: Artificial Sequence
<220> FEATURE:
<223> OTHER INFORMATION: Primer

<400> SEQUENCE: 16
ccgctcgagt tactctggtt gtggtgcagg agctggttt                             39

<210> SEQ ID NO 17
<211> LENGTH: 33
<212> TYPE: DNA
<213> ORGANISM: Artificial Sequence
<220> FEATURE:
<223> OTHER INFORMATION: Primer

<400> SEQUENCE: 17
ccggatccag cgtcgctatc ttagggggctg gtt                                  33

<210> SEQ ID NO 18
<211> LENGTH: 27
<212> TYPE: DNA
<213> ORGANISM: Artificial Sequence
<220> FEATURE:
<223> OTHER INFORMATION: Primer

<400> SEQUENCE: 18
ccacataccg ttttcttgtt tccagcc                                          27

<210> SEQ ID NO 19
<211> LENGTH: 33
<212> TYPE: DNA
<213> ORGANISM: Artificial Sequence
<220> FEATURE:
<223> OTHER INFORMATION: Primer

<400> SEQUENCE: 19
ggaattccat atggaagaag cccccgtagc tag                                   33

<210> SEQ ID NO 20
<211> LENGTH: 32
<212> TYPE: DNA
<213> ORGANISM: Artificial Sequence
<220> FEATURE:
<223> OTHER INFORMATION: Primer

<400> SEQUENCE: 20
ccgctcgagt tattctggtt taggagctgg ag                                    32

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
ccgctcgagt tattttggtg caggagctgg                                       30

<210> SEQ ID NO 22
<211> LENGTH: 32
<212> TYPE: DNA

<213> ORGANISM: Artificial Sequence
<220> FEATURE:
<223> OTHER INFORMATION: Primer

<400> SEQUENCE: 22
ccgctcgagt tatggagtgg ctggttttc tg                                    32

<210> SEQ ID NO 23
<211> LENGTH: 33
<212> TYPE: DNA
<213> ORGANISM: Artificial Sequence
<220> FEATURE:
<223> OTHER INFORMATION: Primer

<400> SEQUENCE: 23
ggaattccat atggaagaat ctcccgtagc tag                                  33

<210> SEQ ID NO 24
<211> LENGTH: 20
<212> TYPE: PRT
<213> ORGANISM: Artificial Sequence
<220> FEATURE:
<223> OTHER INFORMATION: Prolin-rich motif

<400> SEQUENCE: 24

Thr Gly Trp Leu Gln Val Asn Gly Ser Trp Tyr Tyr Leu Asn Ala Asn
1               5                   10                  15

Gly Ala Met Ala
            20

<210> SEQ ID NO 25
<211> LENGTH: 370
<212> TYPE: PRT
<213> ORGANISM: Artificial Sequence
<220> FEATURE:
<223> OTHER INFORMATION: Fragment of PspA

<400> SEQUENCE: 25

Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
                20                  25                  30

Gln Lys Ala Leu Asp Asp Ala Lys Ala Ala Gln Lys Lys Tyr Asp Glu
        35                  40                  45

Asp Gln Lys Lys Thr Glu Glu Lys Ala Ala Leu Glu Lys Ala Ala Ser
    50                  55                  60

Glu Glu Met Asp Lys Ala Val Ala Ala Val Gln Gln Ala Tyr Leu Ala
65                  70                  75                  80

Tyr Gln Gln Ala Thr Asp Lys Ala Ala Lys Asp Ala Ala Asp Lys Met
                85                  90                  95

Ile Asp Glu Ala Lys Lys Arg Glu Glu Glu Ala Lys Thr Lys Phe Asn
            100                 105                 110

Thr Val Arg Ala Met Val Val Pro Glu Pro Glu Gln Leu Ala Glu Thr
        115                 120                 125

Lys Lys Lys Ser Glu Glu Ala Lys Gln Lys Ala Pro Glu Leu Thr Lys
    130                 135                 140

Lys Leu Glu Glu Ala Lys Ala Lys Leu Glu Glu Ala Glu Lys Lys Ala
145                 150                 155                 160

Thr Glu Ala Lys Gln Lys Val Asp Ala Glu Glu Val Ala Pro Gln Ala
                165                 170                 175

Lys Ile Ala Glu Leu Glu Asn Gln Val His Arg Leu Glu Gln Glu Leu
                180                 185                 190

Lys Glu Ile Asp Glu Ser Glu Ser Glu Asp Tyr Ala Lys Glu Gly Phe
            195                 200                 205

Arg Ala Pro Leu Gln Ser Lys Leu Asp Ala Lys Lys Ala Lys Leu Ser
        210                 215                 220

Lys Leu Glu Glu Leu Ser Asp Lys Ile Asp Glu Leu Asp Ala Glu Ile
225                 230                 235                 240

Ala Lys Leu Glu Asp Gln Leu Lys Ala Ala Glu Asn Asn Asn Val
                245                 250                 255

Glu Asp Tyr Phe Lys Glu Gly Leu Glu Lys Thr Ile Ala Ala Lys Lys
            260                 265                 270

Ala Glu Leu Glu Lys Thr Glu Ala Asp Leu Lys Lys Ala Val Asn Glu
        275                 280                 285

Pro Glu Lys Pro Ala Pro Ala Pro Glu Thr Pro Ala Pro Glu Ala Pro
        290                 295                 300

Ala Glu Gln Pro Lys Pro Ala Pro Ala Pro Gln Pro Ala Pro Ala Pro
305                 310                 315                 320

Lys Pro Glu Lys Pro Ala Glu Gln Pro Lys Pro Glu Lys Thr Asp Asp
                325                 330                 335

Gln Gln Ala Glu Glu Asp Tyr Ala Arg Arg Ser Glu Glu Tyr Asn
            340                 345                 350

Arg Leu Thr Gln Gln Gln Pro Pro Lys Ala Glu Lys Pro Ala Pro Ala
        355                 360                 365

Pro Lys
    370

<210> SEQ ID NO 26
<211> LENGTH: 378
<212> TYPE: PRT
<213> ORGANISM: Artificial Sequence
<220> FEATURE:
<223> OTHER INFORMATION: Fragment of PspA

<400> SEQUENCE: 26

Glu Glu Ser Pro Val Ala Ser Gln Ser Lys Ala Glu Lys Asp Tyr Asp
1               5                   10                  15

Ala Ala Val Lys Lys Ser Glu Ala Ala Lys Lys Ala Tyr Glu Glu Ala
            20                  25                  30

Lys Lys Ala Leu Glu Glu Ala Lys Val Ala Gln Lys Lys Tyr Glu Asp
        35                  40                  45

Asp Gln Lys Lys Thr Glu Glu Lys Ala Glu Leu Glu Lys Glu Ala Ser
    50                  55                  60

Glu Ala Ile Ala Lys Ala Thr Glu Glu Val Gln Gln Ala Tyr Leu Ala
65                  70                  75                  80

Tyr Gln Arg Ala Ser Asn Lys Ala Glu Ala Ala Lys Met Ile Glu Glu
                85                  90                  95

Ala Gln Arg Arg Glu Asn Glu Ala Arg Ala Lys Phe Thr Thr Ile Arg
            100                 105                 110

Thr Thr Met Val Val Pro Glu Pro Glu Gln Leu Ala Glu Thr Lys Lys
        115                 120                 125

Lys Ala Glu Glu Ala Lys Ala Lys Glu Pro Lys Leu Ala Lys Lys Ala
    130                 135                 140

Ala Glu Ala Lys Ala Lys Leu Glu Glu Ala Glu Lys Lys Ala Thr Glu
145                 150                 155                 160

Ala Lys Gln Lys Val Asp Ala Glu Glu Val Ala Pro Gln Ala Lys Ile
                165                 170                 175

Ala Glu Leu Glu Asn Gln Val His Arg Leu Glu Gln Glu Leu Lys Glu
            180                 185                 190

Ile Asp Glu Ser Glu Ser Glu Asp Tyr Ala Lys Glu Gly Phe Arg Ala
        195                 200                 205

Pro Leu Gln Ser Lys Leu Asp Ala Lys Lys Ala Lys Leu Ser Lys Leu
    210                 215                 220

Glu Glu Leu Ser Asp Lys Ile Asp Glu Leu Asp Ala Glu Ile Ala Lys
225                 230                 235                 240

Leu Glu Asp Gln Leu Lys Ala Ala Glu Glu Asn Asn Asn Val Glu Asp
                245                 250                 255

Tyr Phe Lys Glu Gly Leu Glu Lys Thr Ile Ala Ala Lys Lys Ala Glu
            260                 265                 270

Leu Glu Lys Thr Glu Ala Asp Leu Lys Lys Ala Val Asn Glu Pro Glu
        275                 280                 285

Lys Ser Ala Glu Glu Pro Ser Gln Pro Glu Lys Pro Ala Glu Glu Ala
    290                 295                 300

Pro Ala Pro Glu Gln Pro Thr Glu Pro Thr Gln Pro Glu Lys Pro Ala
305                 310                 315                 320

Glu Glu Thr Pro Ala Pro Lys Pro Glu Lys Pro Ala Glu Gln Pro Lys
                325                 330                 335

Ala Glu Lys Thr Asp Asp Gln Gln Ala Glu Glu Asp Tyr Ala Arg Arg
            340                 345                 350

Ser Glu Glu Glu Tyr Asn Arg Leu Thr Gln Gln Pro Pro Lys Ala
        355                 360                 365

Glu Lys Pro Ala Pro Ala Pro Gln Pro Glu
    370                 375

<210> SEQ ID NO 27
<211> LENGTH: 493
<212> TYPE: PRT
<213> ORGANISM: Artificial Sequence
<220> FEATURE:
<223> OTHER INFORMATION: Fragment of PspA

<400> SEQUENCE: 27

Glu Glu Ser Pro Gln Val Val Glu Lys Ser Ser Leu Glu Lys Lys Tyr
1               5                   10                  15

Glu Glu Ala Lys Ala Lys Ala Asp Thr Ala Lys Lys Asp Tyr Glu Thr
            20                  25                  30

Ala Lys Lys Lys Ala Glu Asp Ala Gln Lys Lys Tyr Glu Asp Asp Gln
        35                  40                  45

Lys Arg Thr Glu Glu Lys Ala Arg Lys Glu Ala Glu Ala Ser Gln Lys
    50                  55                  60

Leu Asn Asp Val Ala Leu Val Val Gln Asn Ala Tyr Lys Glu Tyr Arg
65                  70                  75                  80

Glu Val Gln Asn Gln Arg Ser Lys Tyr Lys Ser Asp Ala Glu Tyr Gln
                85                  90                  95

Lys Lys Leu Thr Glu Val Asp Ser Lys Ile Glu Lys Ala Arg Lys Glu
            100                 105                 110

Gln Gln Asp Leu Gln Asn Lys Phe Asn Glu Val Arg Ala Val Val Val
        115                 120                 125

Pro Glu Pro Asn Ala Leu Ala Glu Thr Lys Lys Lys Ala Glu Glu Ala
    130                 135                 140

```
Lys Ala Glu Glu Lys Val Ala Lys Arg Lys Tyr Asp Tyr Ala Thr Leu
145                 150                 155                 160

Lys Val Ala Leu Ala Lys Lys Glu Val Glu Ala Lys Glu Leu Glu Ile
            165                 170                 175

Glu Lys Leu Gln Tyr Glu Ile Ser Thr Leu Glu Gln Glu Val Ala Thr
        180                 185                 190

Ala Gln His Gln Val Asp Asn Leu Lys Lys Leu Leu Ala Gly Ala Asp
    195                 200                 205

Pro Asp Asp Gly Thr Glu Val Ile Glu Ala Lys Leu Lys Lys Gly Glu
210                 215                 220

Ala Glu Leu Asn Ala Lys Gln Ala Glu Leu Ala Lys Lys Gln Thr Glu
225                 230                 235                 240

Leu Glu Lys Leu Leu Asp Ser Leu Asp Pro Glu Gly Lys Thr Gln Asp
                245                 250                 255

Glu Leu Asp Lys Glu Ala Glu Ala Glu Leu Asp Lys Lys Ala Asp
        260                 265                 270

Glu Leu Gln Asn Lys Val Ala Asp Leu Glu Lys Glu Ile Ser Asn Leu
    275                 280                 285

Glu Ile Leu Leu Gly Gly Ala Asp Pro Glu Asp Asp Thr Ala Ala Leu
290                 295                 300

Gln Asn Lys Leu Ala Ala Lys Lys Ala Glu Leu Ala Lys Lys Gln Thr
305                 310                 315                 320

Glu Leu Glu Lys Leu Leu Asp Ser Leu Asp Pro Glu Gly Lys Thr Gln
                325                 330                 335

Asp Glu Leu Asp Lys Glu Ala Glu Glu Ala Glu Leu Asp Lys Lys Ala
            340                 345                 350

Asp Glu Leu Gln Asn Lys Val Ala Asp Leu Lys Glu Ile Ser Asn
            355                 360                 365

Leu Glu Ile Leu Leu Gly Gly Ala Asp Ser Glu Asp Asp Thr Ala Ala
        370                 375                 380

Leu Gln Asn Lys Leu Ala Thr Lys Lys Ala Glu Leu Glu Lys Thr Gln
385                 390                 395                 400

Lys Glu Leu Asp Ala Ala Leu Asn Glu Leu Gly Pro Asp Gly Asp Glu
                405                 410                 415

Glu Glu Thr Pro Ala Pro Ala Pro Gln Pro Glu Gln Pro Ala Pro Ala
            420                 425                 430

Pro Lys Pro Glu Gln Pro Ala Pro Ala Pro Lys Pro Glu Gln Pro Ala
        435                 440                 445

Pro Ala Pro Lys Pro Glu Gln Pro Ala Pro Ala Pro Lys Pro Glu Gln
    450                 455                 460

Pro Ala Pro Ala Pro Lys Pro Glu Gln Pro Ala Lys Pro Glu Lys Pro
465                 470                 475                 480

Ala Glu Glu Pro Thr Gln Pro Glu Lys Pro Ala Thr Pro
            485                 490

<210> SEQ ID NO 28
<211> LENGTH: 423
<212> TYPE: PRT
<213> ORGANISM: Artificial Sequence
<220> FEATURE:
<223> OTHER INFORMATION: Fragment of PspA

<400> SEQUENCE: 28

Glu Glu Ala Pro Val Ala Asn Gln Ser Lys Ala Glu Lys Asp Tyr Asp
1               5                   10                  15
```

```
Ala Ala Val Lys Lys Ser Glu Ala Ala Lys Lys Asp Tyr Glu Thr Ala
            20                  25                  30
Lys Lys Lys Ala Glu Asp Ala Gln Lys Lys Tyr Asp Glu Asp Gln Lys
        35                  40                  45
Lys Thr Glu Ala Lys Ala Glu Lys Arg Lys Ala Ser Glu Lys Ile
    50                  55                  60
Ala Glu Ala Thr Lys Glu Val Gln Gln Ala Tyr Leu Ala Tyr Leu Gln
65                  70                  75                  80
Ala Ser Asn Glu Ser Gln Arg Lys Glu Ala Asp Lys Lys Ile Lys Glu
                85                  90                  95
Ala Thr Gln Arg Lys Asp Glu Ala Glu Ala Phe Ala Thr Ile Arg
            100                 105                 110
Thr Thr Ile Val Val Pro Glu Pro Ser Glu Leu Ala Glu Thr Lys Lys
            115                 120                 125
Lys Ala Glu Glu Ala Thr Lys Glu Ala Glu Val Ala Lys Lys Lys Ser
    130                 135                 140
Glu Glu Ala Ala Lys Glu Val Glu Val Gly Lys Asn Lys Ile Leu Glu
145                 150                 155                 160
Gln Asp Ala Glu Asn Glu Lys Lys Ile Asp Val Leu Gln Asn Lys Val
                165                 170                 175
Ala Asp Leu Glu Lys Gly Ile Ala Pro Tyr Gln Asn Glu Val Ala Glu
            180                 185                 190
Leu Asn Lys Glu Ile Ala Arg Leu Gln Ser Asp Leu Lys Asp Ala Glu
        195                 200                 205
Glu Asn Asn Val Glu Asp Tyr Ile Lys Glu Gly Leu Glu Gln Ala Ile
210                 215                 220
Thr Asn Lys Lys Ala Glu Leu Ala Thr Thr Gln Gln Asn Ile Asp Lys
225                 230                 235                 240
Thr Gln Lys Asp Leu Glu Asp Ala Glu Leu Glu Leu Glu Lys Val Leu
                245                 250                 255
Ala Thr Leu Asp Pro Glu Gly Lys Thr Gln Asp Glu Leu Asp Lys Glu
            260                 265                 270
Ala Ala Glu Ala Glu Leu Asn Glu Lys Val Glu Ala Leu Gln Asn Gln
        275                 280                 285
Val Ala Glu Leu Glu Glu Glu Leu Ser Lys Leu Glu Asp Asn Leu Lys
290                 295                 300
Asp Ala Glu Thr Asn Asn Val Glu Asp Tyr Ile Lys Glu Gly Leu Glu
305                 310                 315                 320
Glu Ala Ile Ala Thr Lys Lys Ala Glu Leu Glu Lys Thr Gln Lys Glu
            325                 330                 335
Leu Asp Ala Ala Leu Asn Glu Leu Gly Pro Asp Gly Asp Glu Glu Glu
        340                 345                 350
Thr Pro Ala Pro Ala Pro Gln Pro Glu Lys Pro Ala Glu Glu Pro Glu
        355                 360                 365
Asn Pro Ala Pro Ala Pro Lys Pro Glu Lys Ser Ala Asp Gln Gln Ala
        370                 375                 380
Glu Glu Asp Tyr Ala Arg Arg Ser Glu Glu Tyr Asn Arg Leu Thr
385                 390                 395                 400
Gln Gln Gln Pro Pro Lys Ala Glu Lys Pro Ala Pro Ala Pro Gln Pro
                405                 410                 415
Glu Gln Pro Ala Pro Ala Pro
            420
```

-continued

```
<210> SEQ ID NO 29
<211> LENGTH: 430
<212> TYPE: PRT
<213> ORGANISM: Artificial Sequence
<220> FEATURE:
<223> OTHER INFORMATION: Fragment of PspA

<400> SEQUENCE: 29
```

| Glu | Glu | Ser | Pro | Gln | Val | Val | Glu | Lys | Ser | Leu | Glu | Lys | Tyr |
|---|---|---|---|---|---|---|---|---|---|---|---|---|---|
| 1 | | | | 5 | | | | | 10 | | | | 15 |

Glu Glu Ala Lys Ala Lys Ala Asp Thr Ala Lys Lys Asp Tyr Glu Thr
                20                  25                  30

Ala Lys Lys Lys Ala Glu Asp Ala Gln Lys Lys Tyr Asp Glu Asp Gln
            35                  40                  45

Lys Lys Thr Glu Asp Lys Ala Lys Ala Val Lys Lys Val Asp Glu Glu
        50                  55                  60

Arg Gln Lys Ala Asn Leu Ala Val Gln Lys Ala Tyr Val Glu Tyr Arg
65                  70                  75                  80

Glu Ala Lys Asp Lys Ala Ser Ala Glu Lys Lys Ile Glu Glu Ala Lys
                85                  90                  95

Arg Lys Gln Lys Glu Ala Asn Lys Lys Phe Asn Glu Glu Gln Ala Lys
            100                 105                 110

Val Val Pro Glu Ala Lys Glu Leu Ala Ala Thr Lys Gln Lys Ala Glu
        115                 120                 125

Lys Ala Lys Lys Asp Ala Glu Val Ala Lys Glu Lys Tyr Asp Lys Ala
    130                 135                 140

Val Gln Glu Val Glu Val Glu Lys Asn Lys Ile Leu Glu Gln Asp Ala
145                 150                 155                 160

Glu Asn Glu Lys Lys Ile Asp Val Leu Gln Asn Lys Val Ala Asp Leu
                165                 170                 175

Glu Lys Gly Ile Ala Pro Tyr Gln Asn Lys Val Ala Glu Leu Asn Lys
            180                 185                 190

Glu Ile Ala Arg Leu Gln Ser Asp Leu Lys Asp Ala Glu Glu Asn Asn
        195                 200                 205

Val Glu Asp Tyr Ile Lys Glu Gly Leu Glu Gln Ala Ile Ala Asp Lys
    210                 215                 220

Lys Ala Glu Leu Ala Thr Thr Gln Gln Asn Ile Asp Lys Thr Gln Lys
225                 230                 235                 240

Asp Leu Glu Asp Ala Glu Leu Glu Leu Glu Lys Val Leu Ala Thr Leu
                245                 250                 255

Asp Pro Glu Gly Lys Thr Gln Asp Glu Leu Asp Lys Glu Ala Ala Glu
            260                 265                 270

Asp Ala Asn Ile Glu Ala Leu Gln Asn Lys Val Ala Asp Leu Glu Asn
        275                 280                 285

Lys Val Ala Glu Leu Asp Lys Glu Val Thr Arg Leu Gln Ser Asp Leu
    290                 295                 300

Lys Asp Ala Glu Glu Asn Asn Val Glu Asp Tyr Val Lys Glu Gly Leu
305                 310                 315                 320

Glu Lys Ala Leu Thr Asp Lys Lys Val Glu Leu Asn Asn Thr Gln Lys
                325                 330                 335

Ala Leu Asp Thr Ala Pro Lys Ala Leu Asp Thr Ala Leu Asn Glu Leu
            340                 345                 350

Gly Pro Asp Gly Asp Glu Glu Thr Pro Ala Pro Ala Pro Lys Pro
        355                 360                 365

Glu Gln Pro Ala Glu Gln Pro Lys Pro Ala Pro Ala Pro Lys Pro Glu

```
                370                 375                 380
Lys Thr Asp Asp Gln Gln Ala Glu Glu Asp Tyr Ala Arg Arg Ser Glu
385                 390                 395                 400

Glu Glu Tyr Asn Arg Leu Pro Gln Gln Pro Pro Lys Ala Glu Lys
                405                 410                 415

Pro Ala Pro Ala Pro Lys Pro Glu Gln Pro Val Pro Ala Pro
                420                 425                 430

<210> SEQ ID NO 30
<211> LENGTH: 619
<212> TYPE: PRT
<213> ORGANISM: Streptococcus pneumoniae

<400> SEQUENCE: 30

Met Asn Lys Lys Lys Met Ile Leu Thr Ser Leu Ala Ser Val Ala Ile
1               5                   10                  15

Leu Gly Ala Gly Phe Val Ala Ser Gln Pro Thr Val Val Arg Ala Glu
                20                  25                  30

Glu Ser Pro Val Ala Ser Gln Ser Lys Ala Glu Lys Asp Tyr Asp Ala
            35                  40                  45

Ala Lys Lys Asp Ala Lys Asn Ala Lys Lys Ala Val Glu Asp Ala Gln
50                  55                  60

Lys Ala Leu Asp Asp Ala Lys Ala Ala Gln Lys Lys Tyr Asp Glu Asp
65                  70                  75                  80

Gln Lys Lys Thr Glu Glu Lys Ala Ala Leu Glu Lys Ala Ala Ser Glu
                85                  90                  95

Glu Met Asp Lys Ala Val Ala Ala Val Gln Gln Ala Tyr Leu Ala Tyr
            100                 105                 110

Gln Gln Ala Thr Asp Lys Ala Ala Lys Asp Ala Ala Asp Lys Met Ile
        115                 120                 125

Asp Glu Ala Lys Lys Arg Glu Glu Ala Lys Thr Lys Phe Asn Thr
130                 135                 140

Val Arg Ala Met Val Val Pro Glu Pro Glu Gln Leu Ala Glu Thr Lys
145                 150                 155                 160

Lys Lys Ser Glu Glu Ala Lys Gln Lys Ala Pro Glu Leu Thr Lys Lys
                165                 170                 175

Leu Glu Glu Ala Lys Ala Lys Leu Glu Glu Ala Glu Lys Lys Ala Thr
            180                 185                 190

Glu Ala Lys Gln Lys Val Asp Ala Glu Glu Val Ala Pro Gln Ala Lys
        195                 200                 205

Ile Ala Glu Leu Glu Asn Gln Val His Arg Leu Glu Gln Glu Leu Lys
210                 215                 220

Glu Ile Asp Glu Ser Glu Ser Glu Asp Tyr Ala Lys Glu Gly Phe Arg
225                 230                 235                 240

Ala Pro Leu Gln Ser Lys Leu Asp Ala Lys Lys Ala Lys Leu Ser Lys
                245                 250                 255

Leu Glu Glu Leu Ser Asp Lys Ile Asp Glu Leu Asp Ala Glu Ile Ala
            260                 265                 270

Lys Leu Glu Asp Gln Leu Lys Ala Ala Glu Glu Asn Asn Val Glu
        275                 280                 285

Asp Tyr Phe Lys Glu Gly Leu Glu Lys Thr Ile Ala Ala Lys Lys Ala
            290                 295                 300

Glu Leu Glu Lys Thr Glu Ala Asp Leu Lys Lys Ala Val Asn Glu Pro
305                 310                 315                 320
```

```
Glu Lys Pro Ala Pro Ala Pro Glu Thr Pro Ala Pro Glu Ala Pro Ala
                325                 330                 335

Glu Gln Pro Lys Pro Ala Pro Ala Pro Gln Pro Ala Pro Ala Pro Lys
            340                 345                 350

Pro Glu Lys Pro Ala Glu Gln Pro Lys Pro Glu Lys Thr Asp Asp Gln
        355                 360                 365

Gln Ala Glu Glu Asp Tyr Ala Arg Arg Ser Glu Glu Tyr Asn Arg
    370                 375                 380

Leu Thr Gln Gln Gln Pro Lys Ala Glu Lys Pro Ala Pro Ala Pro
385                 390                 395                 400

Lys Thr Gly Trp Lys Gln Glu Asn Gly Met Trp Tyr Phe Tyr Asn Thr
                405                 410                 415

Asp Gly Ser Met Ala Thr Gly Trp Leu Gln Asn Asn Gly Ser Trp Tyr
            420                 425                 430

Tyr Leu Asn Ser Asn Gly Ala Met Ala Thr Gly Trp Leu Gln Tyr Asn
        435                 440                 445

Gly Ser Trp Tyr Tyr Leu Asn Ala Asn Gly Ala Met Ala Thr Gly Trp
    450                 455                 460

Ala Lys Val Asn Gly Ser Trp Tyr Tyr Leu Asn Ala Asn Gly Ala Met
465                 470                 475                 480

Ala Thr Gly Trp Leu Gln Tyr Asn Gly Ser Trp Tyr Tyr Leu Asn Ala
                485                 490                 495

Asn Gly Ala Met Ala Thr Gly Trp Ala Lys Val Asn Gly Ser Trp Tyr
            500                 505                 510

Tyr Leu Asn Ala Asn Gly Ala Met Ala Thr Gly Trp Leu Gln Tyr Asn
        515                 520                 525

Gly Ser Trp Tyr Tyr Leu Asn Ala Asn Gly Ala Met Ala Thr Gly Trp
    530                 535                 540

Ala Lys Val Asn Gly Ser Trp Tyr Tyr Leu Asn Ala Asn Gly Ala Met
545                 550                 555                 560

Ala Thr Gly Trp Val Lys Asp Gly Asp Thr Trp Tyr Tyr Leu Glu Ala
                565                 570                 575

Ser Gly Ala Met Lys Ala Ser Gln Trp Phe Lys Val Ser Asp Lys Trp
            580                 585                 590

Tyr Tyr Val Asn Gly Leu Gly Ala Leu Ala Val Asn Thr Thr Val Asp
        595                 600                 605

Gly Tyr Lys Val Asn Ala Asn Gly Glu Trp Val
    610                 615

<210> SEQ ID NO 31
<211> LENGTH: 1860
<212> TYPE: DNA
<213> ORGANISM: Streptococcus pneumoniae

<400> SEQUENCE: 31
atgaataaga aaaaaatgat tttaacaagt ctagccagcg tcgctatctt aggggctggt      60
tttgttgcgt ctcagcctac tgttgtaaga gcagaagaat ctcccgtagc cagtcagtct     120
aaagctgaga agactatga tgcagcgaag aaagatgcta agaatgcgaa aaaagcagta     180
gaagatgctc aaaggcttt agatgatgca aaagctgctc agaaaaaata tgacgaggat     240
cagaagaaaa ctgaggagaa agccgcgcta gaaaagcag cgtctgaaga gatggataag     300
gcagtggcag cagttcaaca agcgtatcta gcctatcaac aagctacaga caaagccgca     360
aaagacgcag cagataagat gatagatgaa gctaagaaac gcgaagaaga ggcaaaaact     420
```

```
aaatttaata ctgttcgagc aatggtagtt cctgagccag agcagttggc tgagactaag    480
aaaaaatcag aagaagctaa acaaaaagca ccagaactta ctaaaaaact agaagaagct    540
aaagcaaaat tagaagaggc tgagaaaaaa gctactgaag ccaaacaaaa agtggatgct    600
gaagaagtcg ctcctcaagc taaaatcgct gaattggaaa atcaagttca tagactagaa    660
caagagctca aagagattga tgagtctgaa tcagaagatt atgctaaaga aggtttccgt    720
gctcctcttc aatctaaatt ggatgccaaa aaagctaaac tatcaaaact tgaagagtta    780
agtgataaga ttgatgagtt agacgctgaa attgcaaaac ttgaagatca acttaaagct    840
gctgaagaaa acaataatgt agaagactac tttaaagaag gtttagagaa aactattgct    900
gctaaaaaag ctgaattaga aaaaactgaa gctgaccttt agaaaagcagt taatgagcca    960 gaaaaaccag ctccagctcc agaaactcca gccccagaag caccagctga acaaccaaaa   1020
ccagcgccgg ctcctcaacc agctcccgca ccaaaaccag agaagccagc tgaacaacca   1080
aaaccagaaa aaacagatga tcaacaagct gaagaagact atgctcgtag atcagaagaa   1140
gaatataatc gcttgactca acagcaaccg ccaaaagctg aaaaaccagc tcctgcacca   1200
aaaacaggct ggaaacaaga aaacggtatg tggtacttct acaatactga tggttcaatg   1260
gcgacaggat ggctccaaaa caacggttca tggtactacc tcaacagcaa tggtgctatg   1320
gctacaggtt ggctccaata caatggttca tggtattacc tcaacgctaa cggcgctatg   1380
gcaacaggtt gggctaaagt caacggttca tggtactacc tcaacgctaa tggtgctatg   1440
gctacaggtt ggctccaata caatggttca tggtattacc tcaacgctaa cggcgctatg   1500
gcaacaggtt gggctaaagt caacggttca tggtactacc tcaacgctaa tggtgctatg   1560
gctacaggtt ggctccaata caacggttca tggtactacc tcaacgctaa cggtgctatg   1620
gctacaggtt gggctaaagt caacggttca tggtactacc tcaacgctaa tggtgctatg   1680
gcaacaggtt gggtgaaaga tggagatacc tggtactatc ttgaagcatc aggtgctatg   1740
aaagcaagcc aatggttcaa agtatcagat aaatggtact atgtcaatgg tttaggtgcc   1800
cttgcagtca acacaactgt agatggctat aaagtcaatg ccaatggtga atgggtttaa   1860
```

<210> SEQ ID NO 32
<211> LENGTH: 415
<212> TYPE: PRT
<213> ORGANISM: Streptococcus pneumoniae

<400> SEQUENCE: 32

```
Met Asn Lys Lys Met Ile Leu Thr Ser Leu Ala Ser Val Ala Ile
1               5                   10                  15

Leu Gly Ala Gly Leu Val Ala Ser Gln Pro Thr Leu Val Arg Ala Glu
                20                  25                  30

Glu Ser Pro Val Ala Ser Gln Ser Lys Ala Glu Lys Asp Tyr Asp Ala
            35                  40                  45

Ala Val Lys Lys Ser Glu Ala Ala Lys Lys Ala Tyr Glu Glu Ala Lys
        50                  55                  60

Lys Ala Leu Glu Glu Ala Lys Val Ala Gln Lys Lys Tyr Glu Asp Asp
65                  70                  75                  80

Gln Lys Lys Thr Glu Glu Lys Ala Glu Leu Glu Lys Glu Ala Ser Glu
                85                  90                  95

Ala Ile Ala Lys Ala Thr Glu Glu Val Gln Gln Ala Tyr Leu Ala Tyr
            100                 105                 110

Gln Arg Ala Ser Asn Lys Ala Glu Ala Ala Lys Met Ile Glu Glu Ala
        115                 120                 125
```

```
Gln Arg Arg Glu Asn Glu Ala Arg Ala Lys Phe Thr Thr Ile Arg Thr
        130                 135                 140

Thr Met Val Val Pro Glu Pro Glu Gln Leu Ala Glu Thr Lys Lys Lys
145                 150                 155                 160

Ala Glu Glu Ala Lys Ala Lys Glu Pro Lys Leu Ala Lys Lys Ala Ala
                165                 170                 175

Glu Ala Lys Ala Lys Leu Glu Glu Ala Glu Lys Lys Ala Thr Glu Ala
            180                 185                 190

Lys Gln Lys Val Asp Ala Glu Glu Val Ala Pro Gln Ala Lys Ile Ala
        195                 200                 205

Glu Leu Glu Asn Gln Val His Arg Leu Glu Gln Glu Leu Lys Glu Ile
210                 215                 220

Asp Glu Ser Glu Ser Glu Asp Tyr Ala Lys Glu Gly Phe Arg Ala Pro
225                 230                 235                 240

Leu Gln Ser Lys Leu Asp Ala Lys Ala Lys Leu Ser Lys Leu Glu
                245                 250                 255

Glu Leu Ser Asp Lys Ile Asp Glu Leu Asp Ala Glu Ile Ala Lys Leu
            260                 265                 270

Glu Asp Gln Leu Lys Ala Ala Glu Glu Asn Asn Asn Val Glu Asp Tyr
        275                 280                 285

Phe Lys Glu Gly Leu Glu Lys Thr Ile Ala Ala Lys Lys Ala Glu Leu
290                 295                 300

Glu Lys Thr Glu Ala Asp Leu Lys Lys Ala Val Asn Glu Pro Glu Lys
305                 310                 315                 320

Ser Ala Glu Glu Pro Ser Gln Pro Glu Lys Pro Ala Glu Glu Ala Pro
                325                 330                 335

Ala Pro Glu Gln Pro Thr Glu Pro Thr Gln Pro Glu Lys Pro Ala Glu
            340                 345                 350

Glu Thr Pro Ala Pro Lys Pro Glu Lys Pro Ala Glu Gln Pro Lys Ala
        355                 360                 365

Glu Lys Thr Asp Asp Gln Gln Ala Glu Glu Asp Tyr Ala Arg Arg Ser
370                 375                 380

Glu Glu Glu Tyr Asn Arg Leu Thr Gln Gln Pro Pro Lys Ala Glu
385                 390                 395                 400

Lys Pro Ala Pro Ala Pro Gln Pro Glu Gln Thr Ser Ser Leu His
                405                 410                 415

<210> SEQ ID NO 33
<211> LENGTH: 1319
<212> TYPE: DNA
<213> ORGANISM: Streptococcus pneumoniae

<400> SEQUENCE: 33
aatatttacg gggggagtat acttaatata agtatagtct aaaaatgact atcagaaaag      60
aggtaaattt agatgaataa gaaaaaaatg attttaacaa gtctagccag cgtcgctatc     120
ttaggggctg gtttggttgc gtctcagcct actttggtaa gagcagaaga atctcccgta     180
gctagtcagt ctaaagctga gaaagactat gatgcagcag tgaaaaaatc tgaagctgct     240
aagaaggctt acgaagaagc taaaaaagct ttagaggaag caaagttgc gcaaaaaaaa      300 tatgaagacg atcaaaagaa aactgaagag aaagcagagc tagaaaaaga agcttctgaa     360
gcgatagcta aggcaacaga agaagttcaa caagcgtacc tagcttatca acgagctagc     420
aacaaagccg aagcagctaa gatgatagaa gaggctcaga gacgcgaaaa tgaggcgaga     480
```

-continued

```
gctaaattta ctactattcg aacaacaatg gtagttcctg aaccagaaca gttagctgag    540
actaagaaaa aagcagaaga agctaaagca aaagaaccaa aacttgctaa aaaagcagca    600
gaagctaaag caaaattaga agaggctgag aaaaaagcta ctgaagccaa acaaaaagtg    660
gatgctgaag aagtcgctcc tcaagctaaa atcgctgaat tggaaaatca agttcataga    720
ctagaacaag agctcaaaga gattgatgag tctgaatcag aagattatgc taaagaaggt    780
ttccgtgctc ctcttcaatc taaattggat gccaaaaaag ctaaactatc aaaacttgag    840
gagttaagtg ataagattga tgagttagac gctgaaattg caaaacttga agatcaactt    900
aaagctgctg aagaaaacaa taatgtgaaa gactacttta agaaggtttt agagaaaact    960
attgctgcta aaaagctgaa attagaaaaa actgaagctg accttaagaa agcagttaat   1020
gagccagaaa aatcagctga agagccatcg caaccagaga agccagctga agaagctcca   1080
gccccagagc aaccaactga gccaactcaa ccagaaaaac cagctgaaga aactccagca   1140
ccaaaaccag agaagccagc tgaacaacca aaagcagaaa aaacagatga tcaacaagct   1200
gaagaagact atgctcgtag atcagaagaa gaatataatc gcttgactca acagcaaccg   1260
ccaaaagcag aaaaaccagc tcctgcacca caaccagagc aaaccagctc cttgcacca    1319
```

<210> SEQ ID NO 34
<211> LENGTH: 744
<212> TYPE: PRT
<213> ORGANISM: Streptococcus pneumoniae

<400> SEQUENCE: 34

Met Asn Lys Lys Met Ile Leu Thr Ser Leu Ala Ser Val Ala Ile
1               5                   10                  15

Leu Gly Ala Gly Phe Val Thr Ser Gln Pro Thr Phe Val Arg Ala Glu
            20                  25                  30

Glu Ser Pro Gln Val Val Glu Lys Ser Leu Glu Lys Lys Tyr Glu
        35                  40                  45

Glu Ala Lys Ala Lys Ala Asp Thr Ala Lys Lys Asp Tyr Glu Thr Ala
    50                  55                  60

Lys Lys Lys Ala Glu Asp Ala Gln Lys Lys Tyr Glu Asp Asp Gln Lys
65                  70                  75                  80

Arg Thr Glu Glu Lys Ala Arg Lys Glu Ala Glu Ala Ser Gln Lys Leu
                85                  90                  95

Asn Asp Val Ala Leu Val Val Gln Asn Ala Tyr Lys Glu Tyr Arg Glu
            100                 105                 110

Val Gln Asn Gln Arg Ser Lys Tyr Lys Ser Asp Ala Glu Tyr Gln Lys
        115                 120                 125

Lys Leu Thr Glu Val Asp Ser Lys Ile Glu Lys Ala Arg Lys Glu Gln
    130                 135                 140

Gln Asp Leu Gln Asn Lys Phe Asn Glu Val Arg Ala Val Val Pro
145                 150                 155                 160

Glu Pro Asn Ala Leu Ala Glu Thr Lys Lys Ala Glu Glu Ala Lys
                165                 170                 175

Ala Glu Glu Lys Val Ala Lys Arg Lys Tyr Asp Tyr Ala Thr Leu Lys
            180                 185                 190

Val Ala Leu Ala Lys Lys Glu Val Glu Ala Lys Glu Leu Glu Ile Glu
        195                 200                 205

Lys Leu Gln Tyr Glu Ile Ser Thr Leu Glu Gln Glu Val Ala Thr Ala
    210                 215                 220

Gln His Gln Val Asp Asn Leu Lys Lys Leu Leu Ala Gly Ala Asp Pro

```
                    225                 230                 235                 240

Asp Asp Gly Thr Glu Val Ile Glu Ala Lys Leu Lys Gly Glu Ala
                245                 250                 255

Glu Leu Asn Ala Lys Gln Ala Glu Leu Ala Lys Lys Gln Thr Glu Leu
            260                 265                 270

Glu Lys Leu Leu Asp Ser Leu Asp Pro Glu Gly Lys Thr Gln Asp Glu
        275                 280                 285

Leu Asp Lys Glu Ala Glu Ala Glu Leu Asp Lys Lys Ala Asp Glu
    290                 295                 300

Leu Gln Asn Lys Val Ala Asp Leu Glu Lys Glu Ile Ser Asn Leu Glu
305                 310                 315                 320

Ile Leu Leu Gly Gly Ala Asp Pro Glu Asp Thr Ala Ala Leu Gln
                325                 330                 335

Asn Lys Leu Ala Ala Lys Ala Glu Leu Ala Lys Lys Gln Thr Glu
            340                 345                 350

Leu Glu Lys Leu Leu Asp Ser Leu Asp Pro Glu Gly Lys Thr Gln Asp
        355                 360                 365

Glu Leu Asp Lys Glu Ala Glu Glu Ala Glu Leu Asp Lys Lys Ala Asp
    370                 375                 380

Glu Leu Gln Asn Lys Val Ala Asp Leu Glu Lys Glu Ile Ser Asn Leu
385                 390                 395                 400

Glu Ile Leu Leu Gly Gly Ala Asp Ser Glu Asp Asp Thr Ala Ala Leu
                405                 410                 415

Gln Asn Lys Leu Ala Thr Lys Lys Ala Glu Leu Glu Lys Thr Gln Lys
            420                 425                 430

Glu Leu Asp Ala Ala Leu Asn Glu Leu Gly Pro Asp Gly Asp Glu Glu
        435                 440                 445

Glu Thr Pro Ala Pro Ala Pro Gln Pro Glu Gln Pro Ala Pro Ala Pro
    450                 455                 460

Lys Pro Glu Gln Pro Ala Pro Ala Pro Lys Pro Glu Gln Pro Ala Pro
465                 470                 475                 480

Ala Pro Lys Pro Glu Gln Pro Ala Pro Ala Pro Lys Pro Glu Gln Pro
                485                 490                 495

Ala Pro Ala Pro Lys Pro Glu Gln Pro Ala Pro Lys Pro Glu Lys Pro Ala
            500                 505                 510

Glu Glu Pro Thr Gln Pro Glu Lys Pro Ala Thr Pro Lys Thr Gly Trp
        515                 520                 525

Lys Gln Glu Asn Gly Met Trp Tyr Phe Tyr Asn Thr Asp Gly Ser Met
    530                 535                 540

Ala Ile Gly Trp Leu Gln Asn Asn Gly Ser Trp Tyr Tyr Leu Asn Ala
545                 550                 555                 560

Asn Gly Ala Met Ala Thr Gly Trp Val Lys Asp Gly Asp Thr Trp Tyr
                565                 570                 575

Tyr Leu Glu Ala Ser Gly Ala Met Lys Ala Ser Gln Trp Phe Lys Val
            580                 585                 590

Ser Asp Lys Trp Tyr Tyr Val Asn Ser Asn Gly Ala Met Ala Thr Gly
        595                 600                 605

Trp Leu Gln Tyr Asn Gly Ser Trp Tyr Tyr Leu Asn Ala Asn Gly Asp
    610                 615                 620

Met Ala Thr Gly Trp Leu Gln Tyr Asn Gly Ser Trp Tyr Tyr Leu Asn
625                 630                 635                 640

Ala Asn Gly Asp Met Ala Thr Gly Trp Ala Lys Val Asn Gly Ser Trp
                645                 650                 655
```

```
Tyr Tyr Leu Asn Ala Asn Gly Ala Met Ala Thr Gly Trp Ala Lys Val
            660                 665                 670

Asn Gly Ser Trp Tyr Tyr Leu Asn Ala Asn Gly Ser Met Ala Thr Gly
        675                 680                 685

Trp Val Lys Asp Gly Asp Thr Trp Tyr Tyr Leu Glu Ala Ser Gly Ala
    690                 695                 700

Met Lys Ala Ser Gln Trp Phe Lys Val Ser Asp Lys Trp Tyr Tyr Val
705                 710                 715                 720

Asn Gly Leu Gly Ala Leu Ala Val Asn Thr Thr Val Asp Gly Tyr Lys
            725                 730                 735

Val Asn Ala Asn Gly Glu Trp Val
            740

<210> SEQ ID NO 35
<211> LENGTH: 2235
<212> TYPE: DNA
<213> ORGANISM: Streptococcus pneumoniae

<400> SEQUENCE: 35
```

| | | | | |
|---|---|---|---|---|
| atgaataaga aaaaaatgat tttaacaagt ctagccagcg tcgctatctt aggggctggt | 60 |
| tttgttacgt ctcagcctac ttttgtaaga gcagaagaat ctccacaagt tgtcgaaaaa | 120 |
| tcttcattag agaagaaata tgaggaagca aaagcaaaag ctgatactgc aagaaagat | 180 |
| tacgaaacgg ctaaaagaa agcagaagac gctcagaaaa agtatgaaga tgatcagaag | 240 |
| agaactgagg agaaagctcg aaagaagca gaagcatctc aaaaattgaa tgatgtggcg | 300 |
| cttgttgttc aaaatgcata taagagtac cgagaagttc aaaatcaacg tagtaaatat | 360 |
| aaatctgacg ctgaatatca gaaaaaatta acagaggtcg actctaaaat agagaaggct | 420 |
| aggaaagagc aacaggactt gcaaaataaa tttaatgaag taagagcagt tgtagttcct | 480 |
| gaaccaaatg cgttggctga gactaagaaa aaagcagaag aagctaaagc agaagaaaaa | 540 |
| gtagctaaga gaaatatga ttatgcaact ctaaaggtag cactagcgaa gaaagaagta | 600 |
| gaggctaagg aacttgaaat tgaaaaactt caatatgaaa tttctacttt ggaacaagaa | 660 |
| gttgctactg ctcaacatca agtagataat ttgaaaaaac ttcttgctgg tgcggatcct | 720 |
| gatgatggca cagaagttat agaagctaaa ttaaaaaag gagaagctga gctaaacgct | 780 |
| aaacaagctg agttagcaaa aaacaaaca gaacttgaaa aacttcttga cagccttgat | 840 |
| cctgaaggta agactcagga tgaattagat aaagaagcag aagaagctga gttggataaa | 900 |
| aaagctgatg aacttcaaaa taagttgct gatttagaaa agaaattag taaccttgaa | 960 |
| atattacttg gaggggctga tcctgaagat gatactgctg ctcttcaaaa taaattagct | 1020 |
| gctaaaaaag ctgagttagc aaaaaaacaa acagaacttg aaaaacttct tgacagcctt | 1080 |
| gatcctgaag gtaagactca ggatgaatta gataaagaag cagaagaagc tgagttggat | 1140 |
| aaaaaagctg atgaacttca aaataagtt gctgatttag aaaagaaat tagtaacctt | 1200 |
| gaaatattac ttggagggc tgattctgaa gatgatactg ctgctcttca aaataaatta | 1260 |
| gctactaaaa aagctgaatt ggaaaaaact caaaagaat tagatgcagc tcttaatgag | 1320 |
| ttaggccctg atggagatga agaagaaact ccagcgccgg ctcctcaacc agagcaacca | 1380 |
| gctcctgcac caaaaccaga gcaaccagct ccagctccaa aaccagagca accagctcct | 1440 |
| gcaccaaaac cagagcaacc agctccagct ccaaaaccag agcaaccagc tccagctcca | 1500 |
| aaaccagagc aaccagctaa gccggagaaa ccagctgaag agcctactca accagaaaaa | 1560 |

-continued

```
ccagccactc caaaaacagg ctggaaacaa gaaaacggta tgtggtattt ctacaatact    1620
gatggttcaa tggcaatagg ttggctccaa acaacggtt catggtacta cctaaacgct    1680
aacggcgcta tggcaacagg ttgggtgaaa gatggagata cctggtacta tcttgaagca    1740
tcaggtgcta tgaaagcaag ccaatggttc aaagtatcag ataaatggta ctatgtcaac    1800
agcaatggcg ctatggcgac aggctggctc aatacaatg gctcatggta ctacctcaac    1860
gctaatggtg atatggcgac aggatggctc aatacaacg ttcatggta ttacctcaac    1920 gctaatggtg atatggcgac aggatgggct aaagtcaacg ttcatggta ctacctaaac    1980 gctaacggtc tatggctac aggttgggct aaagtcaacg ttcatggta ctacctaaac    2040 gctaacggtt caatggcaac aggttgggtg aaagatggag atacctggta ctatcttgaa    2100
gcatcaggtg ctatgaaagc aagccaatgg ttcaaagtat cagataaatg gtactatgtc    2160
aatggcttag gtgcccttgc agtcaacaca actgtagatg ctataaagt caatgccaat    2220 ggtgaatggg tttaa                                                    2235
```

<210> SEQ ID NO 36
<211> LENGTH: 653
<212> TYPE: PRT
<213> ORGANISM: Streptococcus pneumoniae

<400> SEQUENCE: 36

```
Met Asn Lys Lys Met Ile Leu Thr Ser Leu Ala Ser Val Ala Ile
1               5                   10                  15

Leu Gly Ala Gly Phe Val Ala Ser Ser Pro Thr Phe Val Arg Ala Glu
            20                  25                  30

Glu Ala Pro Val Ala Asn Gln Ser Lys Ala Glu Lys Asp Tyr Asp Ala
        35                  40                  45

Ala Val Lys Lys Ser Glu Ala Ala Lys Lys Asp Tyr Glu Thr Ala Lys
    50                  55                  60

Lys Lys Ala Glu Asp Ala Gln Lys Lys Tyr Asp Glu Asp Gln Lys Lys
65                  70                  75                  80

Thr Glu Ala Lys Ala Glu Lys Glu Arg Lys Ala Ser Glu Lys Ile Ala
                85                  90                  95

Glu Ala Thr Lys Glu Val Gln Gln Ala Tyr Leu Ala Tyr Leu Gln Ala
            100                 105                 110

Ser Asn Glu Ser Gln Arg Lys Glu Ala Asp Lys Lys Ile Lys Glu Ala
        115                 120                 125

Thr Gln Arg Lys Asp Glu Ala Glu Ala Ala Phe Ala Thr Ile Arg Thr
    130                 135                 140

Thr Ile Val Val Pro Glu Pro Ser Glu Leu Ala Glu Thr Lys Lys Lys
145                 150                 155                 160

Ala Glu Glu Ala Thr Lys Glu Ala Glu Val Ala Lys Lys Lys Ser Glu
                165                 170                 175

Glu Ala Ala Lys Glu Val Glu Val Glu Lys Asn Lys Ile Leu Glu Gln
            180                 185                 190

Asp Ala Glu Asn Glu Lys Lys Ile Asp Val Leu Gln Asn Lys Val Ala
        195                 200                 205

Asp Leu Glu Lys Gly Ile Ala Pro Tyr Gln Asn Glu Val Ala Glu Leu
    210                 215                 220
```

```
Asn Lys Glu Ile Ala Arg Leu Gln Ser Asp Leu Lys Asp Ala Glu Glu
225                 230                 235                 240

Asn Asn Val Glu Asp Tyr Ile Lys Glu Gly Leu Glu Gln Ala Ile Thr
                245                 250                 255

Asn Lys Lys Ala Glu Leu Ala Thr Thr Gln Gln Asn Ile Asp Lys Thr
            260                 265                 270

Gln Lys Asp Leu Glu Asp Ala Glu Leu Glu Leu Glu Lys Val Leu Ala
        275                 280                 285

Thr Leu Asp Pro Glu Gly Lys Thr Gln Asp Glu Leu Asp Lys Glu Ala
290                 295                 300

Ala Glu Ala Glu Leu Asn Glu Lys Val Glu Ala Leu Gln Asn Gln Val
305                 310                 315                 320

Ala Glu Leu Glu Glu Glu Leu Ser Lys Leu Glu Asp Asn Leu Lys Asp
                325                 330                 335

Ala Glu Thr Asn Asn Val Glu Asp Tyr Ile Lys Glu Gly Leu Glu Glu
                340                 345                 350

Ala Ile Ala Thr Lys Lys Ala Glu Leu Glu Lys Thr Gln Lys Glu Leu
            355                 360                 365

Asp Ala Ala Leu Asn Glu Leu Gly Pro Asp Gly Asp Glu Glu Glu Thr
        370                 375                 380

Pro Ala Pro Ala Pro Gln Pro Glu Lys Pro Ala Glu Glu Pro Glu Asn
385                 390                 395                 400

Pro Ala Pro Ala Pro Lys Pro Glu Lys Ser Ala Asp Gln Gln Ala Glu
                405                 410                 415

Glu Asp Tyr Ala Arg Arg Ser Glu Glu Tyr Asn Arg Leu Thr Gln
                420                 425                 430

Gln Gln Pro Pro Lys Ala Glu Lys Pro Ala Pro Ala Pro Gln Pro Glu
            435                 440                 445

Gln Pro Ala Pro Ala Pro Lys Ile Gly Trp Lys Gln Glu Asn Gly Met
        450                 455                 460

Trp Tyr Phe Tyr Asn Thr Asp Gly Ser Met Ala Thr Gly Trp Leu Gln
465                 470                 475                 480

Asn Asn Gly Ser Trp Tyr Tyr Leu Asn Ser Asn Gly Ala Met Ala Thr
                485                 490                 495

Gly Trp Leu Gln Tyr Asn Gly Ser Trp Tyr Tyr Leu Asn Ala Asn Gly
                500                 505                 510

Ala Met Ala Thr Gly Trp Leu Gln Tyr Asn Gly Ser Trp Tyr Tyr Leu
            515                 520                 525

Asn Ala Asn Gly Ala Met Ala Thr Gly Trp Leu Gln Tyr Asn Gly Ser
        530                 535                 540

Trp Tyr Tyr Leu Asn Ala Asn Gly Asp Met Ala Thr Gly Trp Leu Gln
545                 550                 555                 560

Tyr Asn Gly Ser Trp Tyr Tyr Leu Asn Ala Asn Gly Asp Met Ala Thr
                565                 570                 575

Gly Trp Ala Lys Val His Gly Ser Trp Tyr Tyr Leu Asn Ala Asn Gly
            580                 585                 590

Ser Met Ala Thr Gly Trp Val Lys Asp Gly Glu Thr Trp Tyr Tyr Leu
        595                 600                 605

Glu Ala Ser Gly Ser Met Lys Ala Asn Gln Trp Phe Gln Val Ser Asp
610                 615                 620

Lys Trp Tyr Tyr Val Asn Gly Leu Gly Ser Leu Ser Val Asn Thr Thr
625                 630                 635                 640
```

Val Asp Gly Tyr Lys Val Asn Ala Asn Gly Glu Trp Val
            645                 650

<210> SEQ ID NO 37
<211> LENGTH: 2046
<212> TYPE: DNA
<213> ORGANISM: Streptococcus pneumoniae

<400> SEQUENCE: 37

| | | | | |
|---|---|---|---|---|
| ttgacaaata | tttacggagg | aggcttatgc | ttaatataag | tataggctaa | aaatgattat | 60 |
| cagaaaagag | gtaaatttag | atgaataaga | aaaaaatgat | tttaacaagc | ctagccagcg | 120 |
| tcgctatctt | aggggctggt | tttgttgcgt | cttcgcctac | ttttgtaaga | gcagaagaag | 180 |
| ctcctgtagc | taaccagtct | aaagctgaga | agactatga | tgcagcagtg | aaaaaatctg | 240 |
| aagctgctaa | gaaagattac | gaaacggcta | aaagaaagc | agaagacgct | cagaagaaat | 300 |
| atgatgagga | tcagaagaaa | actgaggcaa | agcggaaaa | agaaagaaaa | gcttctgaaa | 360 |
| agatagctga | ggcaacaaaa | gaagttcaac | aagcgtacct | agcttatcta | caagctagca | 420 |
| acgaaagtca | gagaaaagag | gcagataaga | agataaaaga | agctacgcaa | cgcaaagatg | 480 |
| aggcggaagc | tgcatttgct | actattcgaa | caacaattgt | agttcctgaa | ccaagtgagt | 540 |
| tagctgagac | taagaaaaaa | gcagaagagg | caacaaaaga | agcagaagta | gctaagaaaa | 600 |
| aatctgaaga | ggcagctaaa | gaggtagaag | tagagaaaaa | taaatactt | gaacaagatg | 660 |
| ctgaaaacga | aagaaaatt | gacgtacttc | aaaacaagt | cgctgattta | gaaaaaggaa | 720 |
| ttgctcctta | tcaaaacgaa | gtcgctgaat | taaataaaga | aattgctaga | cttcaaagcg | 780 |
| atttaaaaga | tgctgaagaa | ataatgtag | aagactacat | taaagaaggt | ttagagcaag | 840 |
| ctatcactaa | taaaaaagct | gaattagcta | caactcaaca | aaacatagat | aaaactcaaa | 900 |
| aagatttaga | ggatgctgaa | ttgaacttg | aaaagtatt | agctacatta | gaccctgaag | 960 |
| gtaaaactca | agatgaatta | gataaagaag | ctgctgaagc | tgagttgaat | gaaaaagttg | 1020 |
| aagctcttca | aaaccaagtt | gctgaattag | aagaagaact | ttcaaaactt | gaagataatc | 1080 |
| ttaaagatgc | tgaaacaaac | aacgttgaag | actacattaa | agaaggtta | gaagaagcta | 1140 |
| tcgcgactaa | aaaagctgaa | ttggaaaaaa | ctcaaaaga | attagatgca | gctcttaatg | 1200 |
| agttaggccc | tgatggagat | gaagaagaga | ctccagcgcc | ggctcctcaa | ccagaaaaac | 1260 |
| cagctgaaga | gcctgagaat | ccagctccag | caccaaaacc | agaagtca | gcagatcaac | 1320 |
| aagctgaaga | agactatgct | cgtagatcag | aagaagaata | taatcgcttg | acccaacagc | 1380 |
| aaccgccaaa | agcagaaaaa | ccagctcctg | caccacaacc | agagcaacca | gctcctgcac | 1440 |
| caaaaatagg | ttggaaacaa | gaaaacggta | tgtggtactt | ctacaatact | gatggttcaa | 1500 |
| tggcgacagg | ttggctacaa | aacaacggtt | catggtacta | cctcaacagc | aatggcgcta | 1560 |
| tggctacagg | ttggctccaa | tacaatggtt | catggtatta | cctaaacgct | aacggcgcta | 1620 |
| tggcgacagg | ctggctccaa | tacaatggct | catggtacta | cctcaacgct | aacggcgcta | 1680 |
| tggcgacagg | ctggctccaa | tacaatggct | catggtacta | cctcaacgct | aatggtgata | 1740 |
| tggcgacagg | atggctccaa | tacaacggtt | catggtatta | cctcaacgct | aatggtgata | 1800 |
| tggctacagg | ttgggctaaa | gtccacggtt | catggtacta | cctcaacgct | aacggttcaa | 1860 |
| tggcaacagg | ttgggtgaaa | gatggagaaa | cctggtacta | tcttgaagca | tcaggttcta | 1920 |
| tgaaagcaaa | ccaatggttc | caagtatcag | ataatggta | ctatgtcaat | ggtttaggtt | 1980 |
| cccctttcagt | caacacaact | gtagatggct | ataaagtcaa | tgccaatggt | gaatgggttt | 2040 | aagccg 2046

<210> SEQ ID NO 38
<211> LENGTH: 461
<212> TYPE: PRT
<213> ORGANISM: Streptococcus pneumoniae

<400> SEQUENCE: 38

Met Asn Lys Lys Met Ile Leu Thr Ser Leu Ala Ser Val Ala Ile
1               5                   10                  15

Leu Gly Thr Gly Phe Val Ala Ser Ser Pro Thr Phe Val Arg Ala Glu
                20                  25                  30

Glu Ser Pro Gln Val Val Glu Lys Ser Ser Leu Glu Lys Lys Tyr Glu
                35                  40                  45

Glu Ala Lys Ala Lys Ala Asp Thr Ala Lys Lys Asp Tyr Glu Thr Ala
            50                  55                  60

Lys Lys Lys Ala Glu Asp Ala Gln Lys Lys Tyr Asp Glu Asp Gln Lys
65                  70                  75                  80

Lys Thr Glu Asp Lys Ala Lys Ala Val Lys Val Asp Glu Glu Arg
                85                  90                  95

Gln Lys Ala Asn Leu Ala Val Gln Lys Ala Tyr Val Glu Tyr Arg Glu
                100                 105                 110

Ala Lys Asp Lys Ala Ser Ala Glu Lys Lys Ile Glu Glu Ala Lys Arg
            115                 120                 125

Lys Gln Lys Glu Ala Asn Lys Lys Phe Asn Glu Glu Gln Ala Lys Val
130                 135                 140

Val Pro Glu Ala Lys Glu Leu Ala Ala Thr Lys Gln Lys Ala Glu Lys
145                 150                 155                 160

Ala Lys Lys Asp Ala Glu Val Ala Lys Glu Lys Tyr Asp Lys Ala Val
                165                 170                 175

Gln Glu Val Glu Val Glu Lys Asn Lys Ile Leu Glu Gln Asp Ala Glu
            180                 185                 190

Asn Glu Lys Lys Ile Asp Val Leu Gln Asn Lys Val Ala Asp Leu Glu
            195                 200                 205

Lys Gly Ile Ala Pro Tyr Gln Asn Lys Val Ala Glu Leu Asn Lys Glu
        210                 215                 220

Ile Ala Arg Leu Gln Ser Asp Leu Lys Asp Ala Glu Glu Asn Val
225                 230                 235                 240

Glu Asp Tyr Ile Lys Glu Gly Leu Glu Gln Ala Ile Ala Asp Lys Lys
                245                 250                 255

Ala Glu Leu Ala Thr Thr Gln Gln Asn Ile Asp Lys Thr Gln Lys Asp
            260                 265                 270

Leu Glu Asp Ala Glu Leu Glu Leu Glu Lys Val Leu Ala Thr Leu Asp
        275                 280                 285

Pro Glu Gly Lys Thr Gln Asp Glu Leu Asp Lys Glu Ala Ala Glu Asp
    290                 295                 300

Ala Asn Ile Glu Ala Leu Gln Asn Lys Val Ala Asp Leu Glu Asn Lys
305                 310                 315                 320

Val Ala Glu Leu Asp Lys Glu Val Thr Arg Leu Gln Ser Asp Leu Lys
                325                 330                 335

Asp Ala Glu Glu Asn Asn Val Glu Asp Tyr Val Lys Glu Gly Leu Glu
            340                 345                 350

Lys Ala Leu Thr Asp Lys Lys Val Glu Leu Asn Asn Thr Gln Lys Ala
        355                 360                 365

Leu Asp Thr Ala Pro Lys Ala Leu Asp Thr Ala Leu Asn Glu Leu Gly
370                 375                 380

Pro Asp Gly Asp Glu Glu Thr Pro Ala Pro Ala Pro Lys Pro Glu
385                 390                 395                 400

Gln Pro Ala Glu Gln Pro Lys Pro Ala Pro Ala Pro Lys Pro Glu Lys
                405                 410                 415

Thr Asp Asp Gln Gln Ala Glu Glu Asp Tyr Ala Arg Arg Ser Glu Glu
                420                 425                 430

Glu Tyr Asn Arg Leu Pro Gln Gln Pro Pro Lys Ala Glu Lys Pro
                435                 440                 445

Ala Pro Ala Pro Lys Pro Glu Gln Pro Val Pro Ala Pro
450                 455                 460

<210> SEQ ID NO 39
<211> LENGTH: 1457
<212> TYPE: DNA
<213> ORGANISM: Streptococcus pneumoniae

<400> SEQUENCE: 39

| | | | | |
|---|---|---|---|---|
| aatatttacg gggggagtat acttaatata agtatagtct aaaaatgatt atcagaaaag | 60 |
| aggtaaattt agatgaataa gaaaaaaatg attttaacaa gtctagccag cgtcgctatc | 120 |
| ttagggactg gttttgttgc gtcttcgcct acttttgtaa gagcagaaga atctccacaa | 180 |
| gttgtcgaaa atcttcatt agagaagaaa tatgaggaag caaaagcaaa agctgatact | 240 |
| gccaagaaag attacgaaac ggctaaaaag aaagcagaag acgctcagaa gaaatatgat | 300 |
| gaggatcaga gaaaaactga ggataaggca aaagcggtta agaaagttga tgaagaacgt | 360 |
| caaaaagcga atttggcagt tcaaaaggcg tatgtagaat atagagaagc gaaagataaa | 420 |
| gctagcgctg agaaaaagat tgaagaagca aaacgaaaac aaaaagaagc gaacaaaaaa | 480 |
| tttaatgagg agcaagcaaa agtagttcct gaagcaaagg agttagctgc tactaaacaa | 540 |
| aaagcggaaa aagctaaaaa agacgccgaa gtagctaagg aaaaatatga taaggcagtt | 600 |
| caagaggtag aagtagagaa aaataaaata cttgaacaag atgctgaaaa cgaaaagaaa | 660 |
| attgacgtac ttcaaaacaa agtcgctgat ttagaaaaag gaattgctcc ttatcaaaac | 720 |
| aaagtcgctg aattaaataa agaaattgct agacttcaaa gcgatttaaa agatgctgaa | 780 |
| gaaaataatg tagaagacta tattaaagaa ggtttagagc aagctatcgc tgataaaaaa | 840 |
| gctgaattag ctacaactca acaaaacata gataaaactc aaaaagattt agaggatgct | 900 |
| gaattagaac ttgaaaaagt attagctaca ttagaccctg aaggtaaaac tcaagatgaa | 960 |
| ttagataaag aagctgcaga agatgctaat attgaagctc ttcaaaacaa agttgctgat | 1020 |
| ctagaaaaca aggttgctga attagataaa gaagttacta gacttcaaag cgatttaaaa | 1080 |
| gatgctgaag aaaacaatgt agaagactac gttaaagaag cttagagaa agctcttact | 1140 |
| gataaaaaag ttgaattaaa taatactcaa aaagcattag atactgctcc aaaagcatta | 1200 |
| gatactgctc ttaatgaatt aggtcctgac ggtgatgaag aagaaactcc agctccagca | 1260 |
| cccaaaccag agcaaccagc tgaacaaccc aaaccagctc cagcacccaa accagaaaaa | 1320 |
| acagatgatc aacaagctga agaagactat gctcgtagat cagaagaaga atataaccgc | 1380 |
| ttgccccaac agcaaccgcc aaaagcagaa aaaccagctc cagcaccaaa accagagcaa | 1440 |
| ccagttcctg caccaaa | 1457 |